US007960439B1

(12) United States Patent
Zhao

(10) Patent No.: US 7,960,439 B1
(45) Date of Patent: Jun. 14, 2011

(54) ENVIRONMENTALLY SENSITIVE FOLDABLE OLIGOMERS

(75) Inventor: Yan Zhao, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 83 days.

(21) Appl. No.: 11/811,905

(22) Filed: Jun. 12, 2007

Related U.S. Application Data

(60) Provisional application No. 60/804,503, filed on Jun. 12, 2006.

(51) Int. Cl.
| | |
|---|---|
| *A61K 47/30* | (2006.01) |
| *C08G 73/00* | (2006.01) |
| *G01N 21/00* | (2006.01) |
| *G01N 21/64* | (2006.01) |
| *G01N 24/08* | (2006.01) |

(52) U.S. Cl. ............... 514/772.3; 436/164; 436/172; 436/173; 528/374; 528/391; 528/399; 528/421; 528/422

(58) Field of Classification Search .............. 540/47, 540/106; 552/509, 515; 514/182
See application file for complete search history.

(56) References Cited

U.S. PATENT DOCUMENTS

| | | | |
|---|---|---|---|
| 5,250,524 | A | 10/1993 | Kramer et al. |
| 5,466,815 | A | 11/1995 | Enhsen et al. |

FOREIGN PATENT DOCUMENTS

| | | |
|---|---|---|
| EP | 0551844 A2 | 7/1993 |
| WO | WO-2006034369 | 3/2006 |

OTHER PUBLICATIONS

Feigel et al. Synthesis and Structure of Macrolactams of 3α-Aminodeoxycholanic Acid (Eur. J. Org. Chem. 2006 (2), 371-77, published online Aug. 26, 2005).*
Anaspec Inc. Overview of peptide synthesis (http://www.anaspec.com/resources/peptide.asp), Published online Mar. 3, 2005 Date verified at http://web.archive.org Accessed online Feb. 3, 2010.*
Baringhaus, K. H., et al., "Substrate specificity of the ileal and the hepatic Na(+)/bile acid cotransporters of the rabit. II. A reliable 3D QSAR pharmacophore model for the ileal Na(+)/bile acid cotransporter.", *J Lipid Res.*, 40(12), (Dec. 1999),2158-68.
Kramer, W. , et al., "Topological photoaffinity labeling of the rabbit ileal Na+/bile-salt-cotransport system.", *Eur J Biochem.*, 249(2), (Oct. 15, 1997),456-64.
Zhao, Y. , et al., "From Switchable Supramolecular Hosts to Foldamers with Large Internal Hydrophilic Cavities", *Proceedings of the Gordon Research Conference*, presentation slides,(Jun. 12, 2005),15 p.
Zhao, Y. , et al., "Oligomeric Cholates: Amphiphilic Foldamers with Nanometer-Sized Hydorphilic Cavities", *J. Am. Chem. Soc.*, 127, (2005),17894-17901.
Zhong, Z. , et al., "Cholic acid-derived facial amphiphiles with different ionic characteristics.", *Langmuir*, 21(14), (Jul. 5, 2005),6235-9.
Zhu, X.-X. , et al., "Polymeric Materials Containing Bile Acids", *Acc. Chem. Res.*, 35, (2002),539-546.
"Acyclic Hydrocarbons", [online]. [retrieved Apr. 22, 2009]. Retrieved from the Internet: <URL: http://www.acdlabls.com/iupac/nomenclature/79/r79_78.htm>, (3 pgs.).
Dluzniewski, A., et al., "Influence of N-3-pyridoyltryptamine (tryptamide) on fetal development in rats and mice.", *Pol J Pharmacol Pharm.*, 39(6), (Nov.-Dec. 1987), 779-86.
"Structure Search—Oligocholate Amides References", (Jan. 7, 2009), 11 pgs.
"Structure Search—Oligocholate Amides Structures", (Jan. 7, 2009), 78 pgs.
"Structure Search—Oligocholate Esters Structures", (Jan. 7, 2009), 95 pgs.
Ryu, E.-H., et al., "Environmentally Responsive Molecular Baskets: Unimolecular Mimics of Both Micelles and Reversed Micelles", *Organic Letters*, 6(18), (2004), 3187-3189.
Hoyle, C. E., et al., "Thiol-Enes: Chemistry of the Past with Promise for the Future", *Journal of Polymer Science: Part A: Polymer Chemistry*, vol. 42, (2004), 5301-5338.
Luo, J., et al., "Invertible Amphiphilic Molecular Pockets Made of Cholic Acid", *Langmuir*, 25(18), (2009), 10913-10917.
Pan, X., et al., "Efficient Construction of Oligocholate Foldamers via "Click" Chemistry and Their Tolerance of Structural Heterogeneity", *Organic Letters*, 11(1), 2009), 69-72.
Sun, K.-H., et al., "Thermogelling Poly(ethylene oxide-b-propylene oxide-b-ethylene oxide) Disulfide Multiblock Copolymer as a Thio-Sensitive Degradable Polymer", *Biomacromolecules*, 7, (2006), 2871-2877.

\* cited by examiner

*Primary Examiner* — Barbara P Badio
*Assistant Examiner* — Sara E Townsley
(74) *Attorney, Agent, or Firm* — Schwegman, Lundberg & Woessner, P.A.

(57) ABSTRACT

The invention relates to oligomers of cholic acid, cholate derivatives and amino acids called "foldamers" that undergo conformational changes in response to changes in temperature, solvent polarity, small molecules, metal ions, and pH. The foldamers can be used in self-assembling monolayers, or as environmental probes to detect changes in the environment, or as protective agents useful for protecting labile materials from the environment, or as a controlled delivery system for delivering drugs and other useful agents to specific in vivo or in vitro sites.

31 Claims, 24 Drawing Sheets

ENVIRONMENTALLY SENSITIVE FOLDABLE OLIGOMERS

RELATED APPLICATIONS

This application claims the benefit of U.S. Provisional Ser. No. 60/804,503, filed Jun. 12, 2006, which application is incorporated herein by reference.

FIELD OF THE INVENTION

The invention relates to environmentally sensitive oligomers that predictably fold under defined conditions and are particularly useful as drug-delivery devices, molecular sensors, or smart materials in general.

BACKGROUND OF THE INVENTION

Conformational control is at the heart of biology. The binding and catalytic functions of many protein receptors and enzymes are regulated through their controlled conformational changes. Biological systems rely on these conformationally responsive molecules to sense and react to constantly fluctuating environmental conditions. The conformational behavior of such biological molecules therefore controls the function and activity of biological molecules.

However, traditional conformationally responsive polymers are very large macromolecules. Their use in applications that require small dimensions such as in nanometer-sized spaces is therefore limited.

The conformations of many molecules are dependent on environmental conditions such as solvent, temperature, pH, ionic strength, light, or specific molecules. Thus, a multitude of variables could be employed to control stimuli-responsive materials. However, while chemists have devoted significant effort to the design and synthesis of foldable oligomers ("foldamers"), synthetic molecules that can adopt predictable, biomolecule-like, ordered conformations under defined conditions are difficult to make. While synthetic polymers have been made to respond to certain environmental stimuli, few of them display the well-controlled conformational changes that are seen under certain conditions with biopolymers such as proteins. Learning to create responsive materials that can be conformationally controlled therefore remains a difficult challenge in the chemical and materials sciences.

SUMMARY OF THE INVENTION

In contrast to the deficiencies of previously available molecules, the molecules of the invention provide highly controlled conformational changes in response to defined stimuli. The molecules of the invention are referred to herein as foldamers, and they have nanometer-sized dimensions. The foldamers of the invention can respond much faster to environmental stimuli than do large macromolecules. Moreover, the conformational changes of the present foldamers are well-behaved and respond to very specific stimuli in highly predictable ways. Stimuli to which the present foldamers can respond include, for example, temperature, solvent polarity, solvent composition, small molecules, metal ions, and pH. These foldamers can readily be used for a variety of applications including thermal, molecular, metal and ion sensing, controlled release, drug delivery, and manipulation of surface properties.

One aspect of the invention is a cholic acid analog of the following formula:

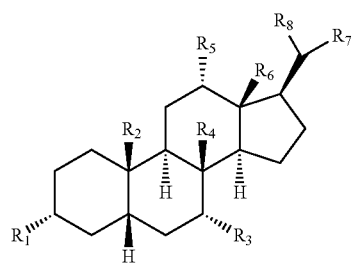

wherein:
$R_1$, $R_3$, and $R_5$ are independently hydrogen, hydroxy (OH), alkoxy, alkoxyalkyl, amine, azide, boronate, mercapto, sulfide, sulfone, sulfoxide, sulfoninium, phosphine, phosphate, phosphate, a heterocycle, a solid support, a linker or a label, wherein each alkoxy and/or alkoxyalkyl can independently be substituted with one or more hydroxy, alkyl, alkenyl, alkynyl, amine, ammonium, sulfate, phosphate, caroboxy, mercapto, sulfide, sulfone, sulfoxide, sulfoninium, phosphine, heteroaromatic cycle, or epoxy groups;
$R_2$, $R_6$ and $R_8$ are independently lower alkyl;
$R_4$ is hydrogen or lower alkyl; and
$R_7$ is carboxylate, alkylenecarboxylate, alkylenecarboxyl, lower alkyl alkylenecarboxylate ester, alkyleneamide, alkyleneamine, alkylenethiol, a solid support, a linker or a label.

Another aspect of the invention is an oligomer of the above cholic acid analog, wherein the monomers are linked by covalent bonds formed between $R_1$ and $R_7$ groups and wherein the oligomer has a hydrophilic face and a hydrophobic face. For example, to form a covalent linkage between $R_1$ and $R_7$, the $R_1$ can be an amine, the $R_7$ can be an alkylenecarboxyl and the $R_1$ amine and $R_7$ alkylcarboxyl groups form an amide covalently linking the cholic acid analogs in the oligomer. The cholate oligomers may also be linked by one or more covalent bonds such as amide, carbamate, urea, ether, sulfide, disulfide, amine, cyclic heteroaromatic ring, or combinations thereof.

Another aspect of the invention is an oligomer comprising the following formula:

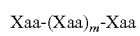

Xaa-(Xaa)$_m$-Xaa wherein:
m is an integer of 2-1000;
each Xaa is independently CHO or an amino acid;
wherein each CHO has the following formula:

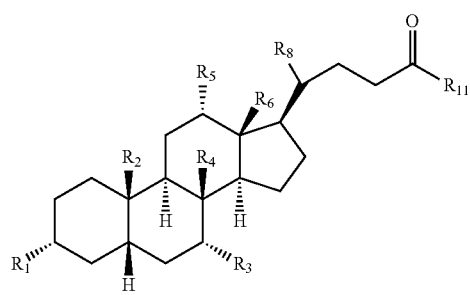

wherein:
$R_1$ is a hydroxy, amine, a solid support, a linker or a label;
$R_2$, $R_6$ and $R_8$ are independently lower alkyl;

$R_3$ and $R_5$ are independently hydrogen, hydroxy (OH), alkoxy, alkoxyalkyl, amine, azide, boronate, mercapto, sulfide, sulfone, sulfoxide, sulfoninium, phosphine, phosphate, phosphate, a heterocycle, a solid support, a linker or a label, wherein each alkoxy and/or alkoxyalkyl can independently be substituted with one or more hydroxy, alkyl, alkenyl, alkynyl, amine, ammonium, sulfate, phosphate, caroboxy, mercapto, sulfide, sulfone, sulfoxide, sulfoninium, phosphine, heteroaromatic cycle, or epoxy groups;

$R_4$ is hydrogen or lower alkyl; and $R_1$, is a hydroxy, a solid support, a linker, a label or a covalent bond to an $R_1$ amine of a Xaa residue;

wherein at least one segment of the oligomer has a hydrophilic face and a hydrophobic face that includes one or more CHO residues. One or more segments of such oligomers can fold into a helix or corkscrew configuration(s).

In some embodiments, a substantially all or a substantial portion of the entire oligomer can fold into a helix or corkscrew configuration. Many types of covalent bonds can link the Xaa subunits. For example, the covalent bonds between the Xaa subunits can be amide, carbamate, urea, ether, sulfide, disulfide, amine, cyclic heteroaromatic ring linkages, or combinations thereof.

In some embodiments, each amino acid of the oligomer is flanked by two CHO residues unless the amino acid is at the terminus of the oligomer. While these oligomers can have any amino acid as well as different CHO residues, in some embodiments, the oligomer has cholic acid residues and at least one Glu, Asp, Lys, Arg, Trp, Met, or Cys.

The CHO-containing oligomers of the invention can be attached to or inserted into a polymer. Such a polymer can be any natural or synthetic polymer such as a polypeptide, polysaccharide, poly(alkylene glycol), poly(N-isopropylacrylamide), poly(acrylamide) or a combination thereof. The CHO-containing oligomers of the invention can also be attached to or inserted into a branched polymer or dendrimer. Such a branched polymer can be a branched polypeptide, polysaccharide, poly(alkylene glycol), poly(N-isopropylacrylamide), poly(acrylamide) or combination thereof. As used herein, a dendrimer is a repeatedly branched molecule. Thus, a dendrimer can be a highly branched polypeptide, polysaccharide, poly(alkylene glycol), poly(N-isopropylacrylamide), poly(acrylamide) or a combination thereof.

The oligomers of the invention can be attached to a solid support. The solid support can be any useful solid support or solid surface, however, in some embodiments the solid support is gold, titanium, chromium, quartz, aluminum, silicon or mixtures and/or layers thereof. The solid support can also be a bead or a column matrix. In some embodiments the solid support is a silicon chip or a gold surface.

The oligomers of the invention can enfold, envelop or encapsulate useful agents. Thus, in some embodiments the oligomer further includes a therapeutic agent.

Due to the hydrophobicity of cholic acid and its derivatives, the folded oligomers of the invention tend to have a hydrophobic exterior surface. Thus, oligomers of the invention can readily be incorporated into liposomes.

Another aspect of the invention is an oligomer comprising the following formula:

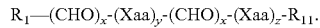

wherein: x, y and z are integers, separately selected from 0-10;

CHO is as described above;
each Xaa is an amino acid;

$R_1$ is a hydroxy, amine, a solid support, a linker or a label;

$R_{11}$ is a hydroxy, a solid support, a linker, a label or a covalent bond to an $R_1$ amine of a Xaa residue.

One aspect of the invention is therefore an oligomer of the invention associated or enclosed within a liposome. In some embodiments, the oligomers are associated or embedded within the lipid bilayer of the liposome. The oligomers associated with liposomes can form pores within the liposome membranes. The liposome-associated oligomers can further include an agent of interest such as a pharmaceutical agent, a mineral, a buffer, a fertilizer, a pesticide, an herbicide and the like. Under selected conditions the oligomers within liposome-associated oligomers of the invention form pores permitting release of agents within the liposomes.

Another aspect of the invention is a composition that includes an agent of interest and an oligomer of the invention. Such compositions can be formulated to include liposome-associated oligomers along with the agents of interest. A further aspect of the invention is a pharmaceutical composition that includes a therapeutically effective amount of a therapeutic agent and the oligomer of the invention. The oligomers of such a pharmaceutical composition can be encapsulated within liposomes. The oligomer is sometimes present in an amount sufficient to bind substantially all of the agent of interest. In some embodiments, the oligomer forms a pore in the liposome to facilitate sustained release of the agent.

Another aspect of the invention is a method of detecting a change in a solution comprising contacting the solution with the oligomer of the invention, observing whether the oligomer undergoes a conformational change and identifying the change in the solution if the oligomer undergoes a conformational change. The conformational changes that can be detected include oligomer folding to expose or envelop charged moieties on or within the oligomer, or oligomer folding into a helix, or unfolding of the oligomer. Any solution can be tested in the methods of the invention. For example, the solution can be a patient's fluid sample, a soil sample, a water sample, a waste fluid sample, or a test sample. In some embodiments, the change in solution detected by the present methods and oligomers is a change in the solution's temperature. Another change in solution that can be detected by the present methods and oligomers is a change in metal ion, or small molecule concentration. Examples of metal ions that can be detected include lead, cadmium, zinc, cobalt, mercury, nickel, silver or iron. In some embodiments, the metal ion detected by the present methods and oligomers is mercury. A variety of small molecules can be detected by the present methods and oligomers including, for example, a drug, a polyanion, a metabolite, a sugar, ATP, GTP, an acid, a base or a hydrocarbon.

Another aspect of the invention is a method of sustained delivery of a therapeutic agent to a patient, comprising administering to the patient one of the compositions of the invention, for example, a pharmaceutical composition. In some embodiments, the composition is locally administered to a selected site of the patient's body. For example, the composition can be administered to site such as a tumor, heart, kidney, brain, or internal organ of the patient.

Another aspect of the invention is an oligomer comprising the following formula:

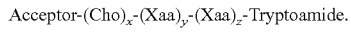

wherein:
x, y and z are integers, separately selected from 0-10;
Cho is 3-aminocholate;

each Xaa is an amino acid; and

Acceptor is a fluorophore that can accept fluorescence energy from tryptamide.

Another aspect of the invention is a cholate oligomer. Examples of oligomeric cholates of the invention include some of the following compounds:

Cho-Cho-Glu-Cho-Cho-Glu-Cho
Cho-Glu-Cho-Cho-Cho-Glu-Cho
Glu-Cho-Cho-Cho-Cho-Glu-Cho
Glu-Cho-Cho-Cho-Cho-Cho-Glu
Cho-Glu-Cho-Cho-Cho-Glu-Cho-Cho
Cho-Glu-Cho-Cho-Cho-Glu-Cho-Cho
Cho-Glu-Cho-Glu-Cho-Glu-Cho-Glu
Cho-Cho-Arg-Cho-Arg-Cho-Cho
Cho-Cho-Arg-Cho-Cho-Arg-Cho-Cho
Dansyl-Cho-Cho-Met-Cho-Cho-Met-Cho-Cho-CONHCH$_2$CH$_2$—(OCH$_2$CH$_2$)OH
2,4-Dimethoxystiblene-Cho-Arg-Cho-Cho-Arg-Cho-Cho-Cho-Trp
Anthracene-Cho-Arg-Cho-Cho-Cho-Cho-Arg-Cho-Trp
7-Dimethylaminocoumarine-Cho-Arg-Cho-Cho-Cho-Cho-Cho-Cho-Arg-Trp
Fluorescein-Cho-Cho-Arg-Cho-Cho-Arg-Cho-Cho-Arg-Trp
Dansyl-Cho-Arg-Cho-Arg-Cho-Arg-Cho-Cho-Cho-Trp
Eosin-Cho-Arg-Cho-Arg-Cho-Arg-Cho-Arg-Cho-Cho-Trp;
Dansyl-Cho-Cho-Met-Cho-Cho-Met-Cho-Cho-Methyl wherein Cho is cholic acid and the Cho residues are covalently linked to other Cho residues or amino acids by an amide bond.

Some examples (e.g., compounds 2-7, 10 and 102) of the oligomers of the invention have the following structures:

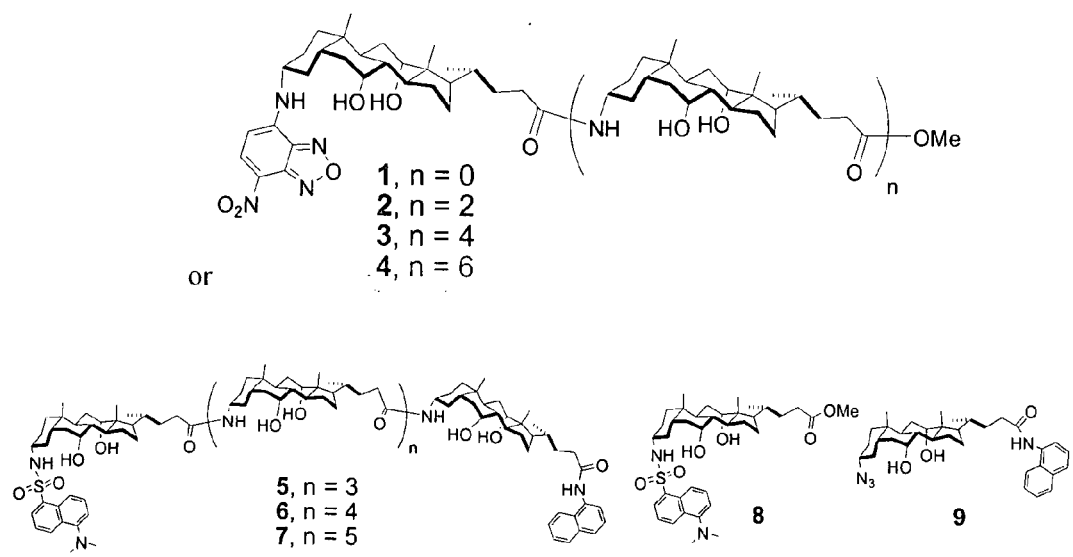
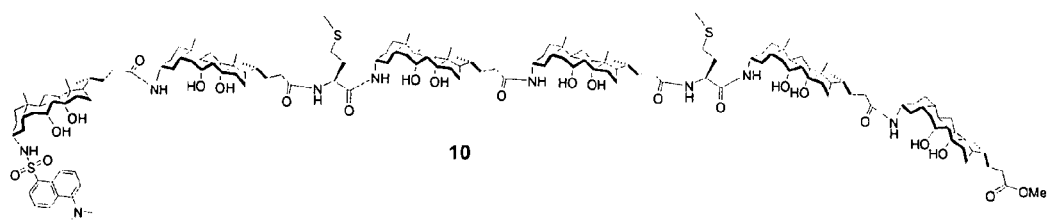
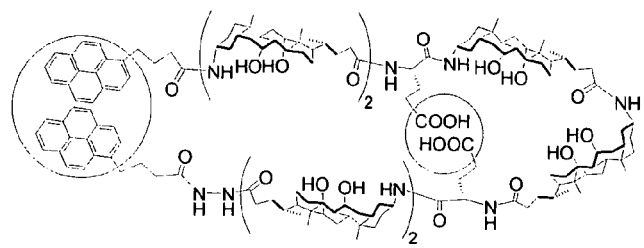
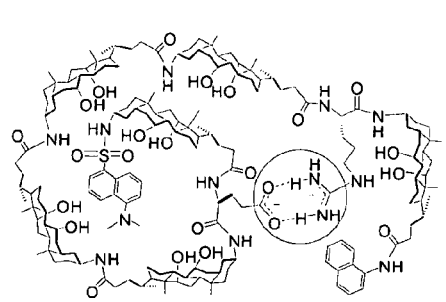

DETAILED DESCRIPTION OF THE INVENTION

Figure 1:
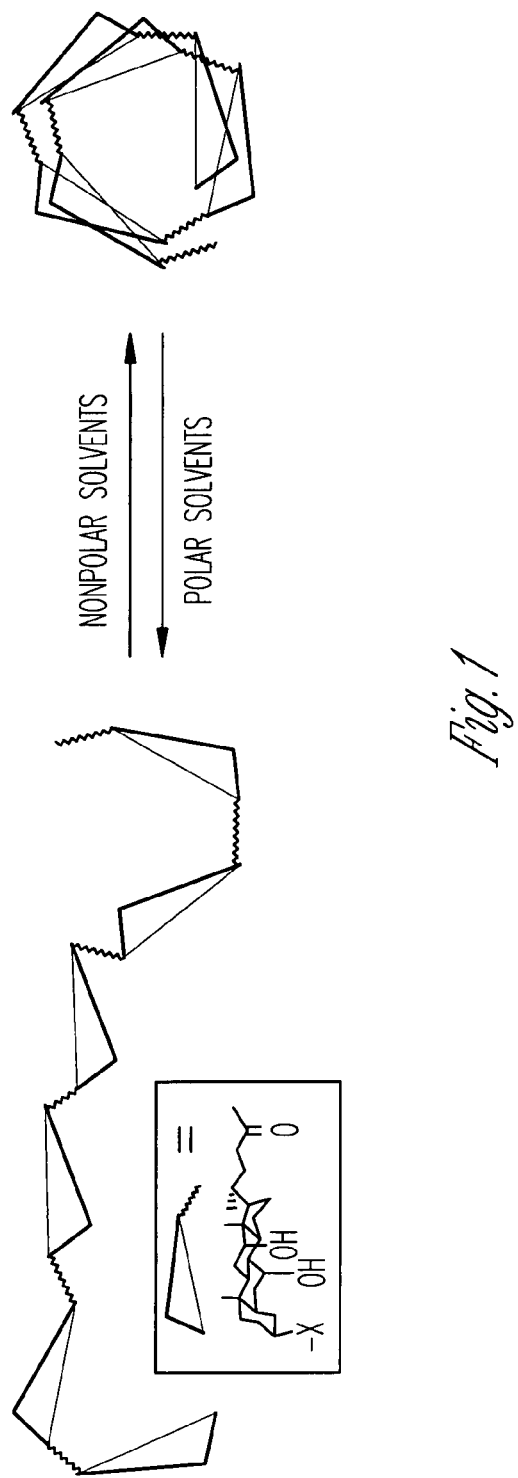
FIG. 1 illustrates the conformational transition of oligomeric cholate between nonpolar and polar solvents.

The invention involves environmentally responsive cholic acid-containing molecules called "foldamers" or cholate oligomers. The present foldamers have a defined structure and conformation under a defined set of conditions. Thus, the foldamer conformation can be made to change under different solvent polarity, solvent composition, and temperature conditions in predictable ways. Because the conformation of the present foldamers is controlled by their environmental conditions, these foldamers can be used as environmental probes to detect changes in the environment, or as protective agents useful for protecting labile materials from the environment, or as a controlled delivery system for delivering drugs and other useful agents to specific in vivo or in vitro sites. In another embodiment, the present foldamers are useful for assuming a given conformation (e.g., a folded helix or an unfolded, random, conformation) under defined conditions. Thus, the present foldamers have a variety of utilities.

DEFINITIONS

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and by using analytical procedures described herein, or using other similar procedures and tests that are well known in the art.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

As used herein, a cyclic heteroaromatic ring linkage is a linkage from a ring atom to an atom in another molecule, subunit or monomer (e.g., an Xaa or CHO subunit). The cyclic heteroaromatic ring can also be linked to two or more molecules, subunits or monomers, so that the cyclic heteroaromatic ring acts as a linker or bridging moiety between two or more molecules, subunits or monomers.

The term "oligomer" means a chain of subunits wherein a significant number, but not necessarily all, of the subunits are CHO (or cholate) residues as defined herein. The oligomers of the invention can contain variable numbers of subunits, so long as the oligomers can fold into helical structures with nanometer-sized hydrophilic cavities. Thus, for example, the oligomers can have up to about 1000 subunits, although in some embodiments fewer subunits are used, for example, up to about 750 subunits, or up to about 500 subunits, or up to about 300 subunits, or up to about 200 subunits, or up to about 100 subunits. The term "subunit" is used interchangeably herein with the term "residue."

Subunits for Foldamers

The foldamers of the invention comprise oligomers of cholic acid monomers, cholate derivatives and other subunits. The structure of cholic acid is shown below.

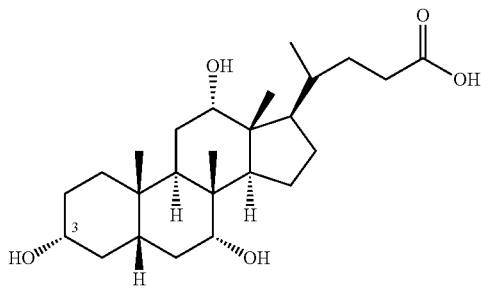

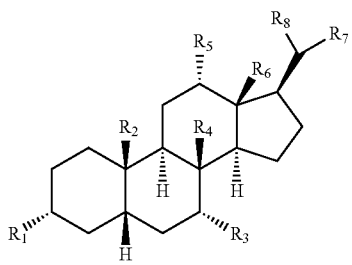

Cholic acid has a number of features that makes it useful in foldamer oligomers. For example, because of the positions of hydrophilic and hydrophobic substituents and the stereoisomeric configuration at these positions, the present cholic acid monomers have two distinct faces: a hydrophobic face (the β face) and a hydrophilic face (the α face). Moreover, the cholic acid monomers have slightly curved configurations and this curvature is toward the hydrophilic face.

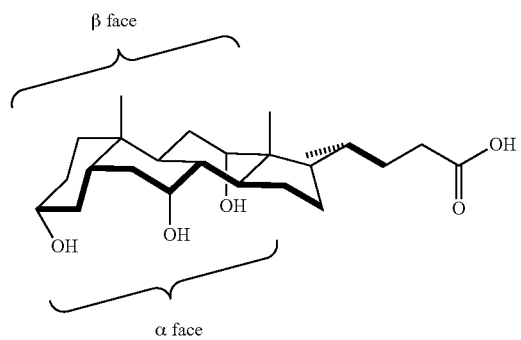

To make an oligomer of cholic acid, the acid moiety can be linked to a selected functional group on cholic acid. In general, it is useful to link the acid moiety of one cholic acid monomer to the three (3) position of another cholic acid moiety. This can easily be done by substituting an amine for the hydroxyl group at position 3 to generate a 3-aminocholate monomer, shown below.

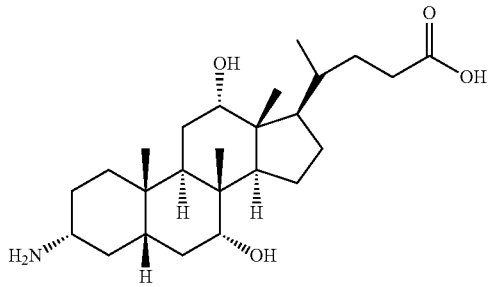

Standard peptide synthetic procedures and reagents can be used to covalently link such aminocholate subunits into oligomers.

The foldamers of the invention can contain other subunits in addition to cholic acid. In some embodiments, the additional subunits include cholic acid analogs and amino acids.

Thus, one such cholic acid analog that can be used in the foldamers of the invention has the following formula:

wherein:

$R_1$, $R_3$, and $R_5$ are independently hydrogen, hydroxy (OH), alkoxy, alkoxyalkyl, amine, azide, boronate, mercapto, sulfide, sulfone, sulfoxide, sulfoninium, phosphine, phosphate, phosphate, a heterocycle, a solid support, a linker or a label, wherein each alkoxy and/or alkoxyalkyl can independently be substituted with one or more hydroxy, alkyl, alkenyl, alkynyl, amine, ammonium, sulfate, phosphate, caroboxy, mercapto, sulfide, sulfone, sulfoxide, sulfoninium, phosphine, heteroaromatic cycle, or epoxy groups;

$R_2$, $R_6$ and $R_8$ are independently lower alkyl;

$R_4$ is hydrogen or lower alkyl;

$R_7$ is carboxylate, alkylenecarboxylate, alkylenecarboxyl, lower alkyl alkylenecarboxylate ester, alkyleneamide, alkyleneamine, alkylenethiol, a solid support, a linker or a label.

In some embodiments, the solid support, linker or label is present at one of oligomer termini. Moreover, in some embodiments $R_1$, or $R_7$ is a solid support, linker or label rather than the $R_3$ or $R_5$ groups. Also, in some embodiments $R_3$, and $R_5$ are hydroxy (OH) or lower alkyl substituted with one or more hydroxy groups.

Some examples of Cho monomers used in the invention are provided below, where the carbonyl of the acid or ester moiety is joined to the nitrogen at ring position 3 when the oligomer is formed.

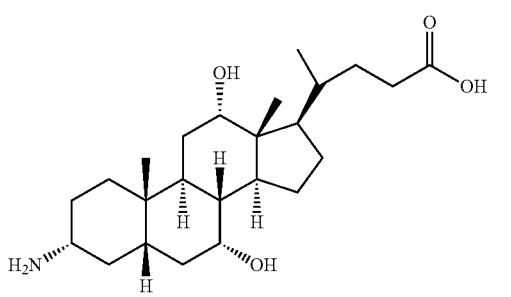

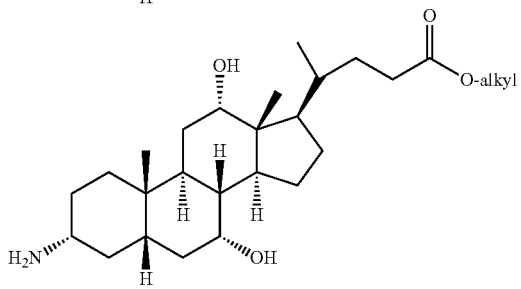

15
-continued

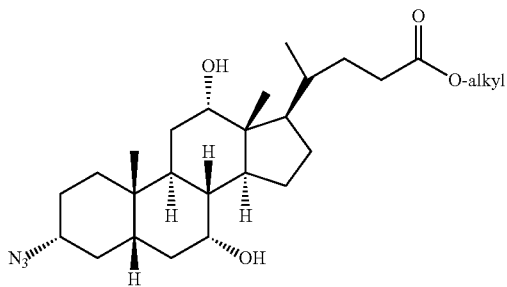

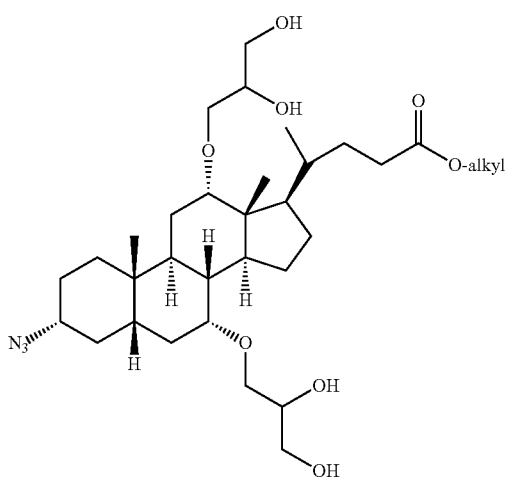

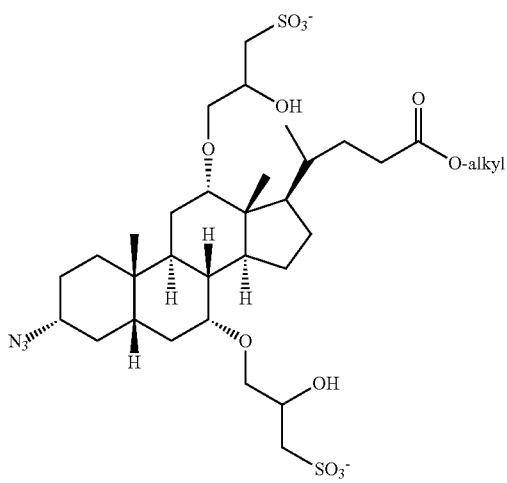

16
-continued

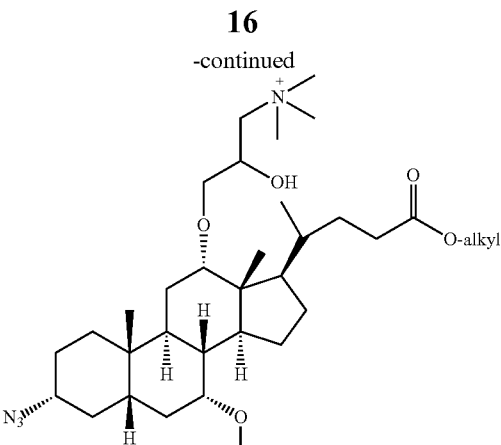

where the $R_{21}$ group is a spacer unit such as alkylene, phenylene, naphthylene, or phenylene ethynylene.

Any natural or synthetic amino acid can be used as subunits in the foldamers of the invention. For example, amino acids used in the present foldamers can be genetically encoded L-amino acids, naturally occurring non-genetically encoded L-amino acids, synthetic L-amino acids or D-enantiomers of any of the above. Examples of amino acids that can be used as well as the amino acid notations used herein for such amino acids are as shown in Table 1.

TABLE 1

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | Bala |
| 2,3-Diaminopropionic acid | | Dpr |

TABLE 1-continued

| Amino Acid | One-Letter Symbol | Common Abbreviation |
|---|---|---|
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | Harg |
| N-acetyl lysine | | AcLys |
| 2,4-Diamino butyric acid | | Dbu |
| ρ-Aminophenylalanine | | Phe(pNH$_2$) |
| N-methylvaline | | MeVal |
| Homocysteine | | Hcys |
| Homoserine | | Hser |
| ε-Amino hexanoic acid | | Aha |
| δ-Amino valeric acid | | Ava |
| 2,3-Diaminobutyric acid | | Dab |

Any such amino acid, or any other amino acid known to one of skill in the art, can be utilized in the foldamers of the invention. However, in some embodiments, the amino acids employed have functional groups such as H—, HO—, HOOC—, H$_2$NOC—, HN=C(NH$_2$)—NH—, HS—, alkyl-S—,

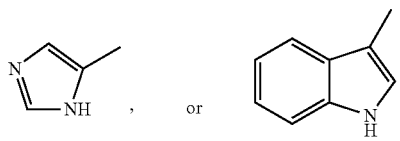

Thus, examples of amino acids that have functional groups that can be used in the foldamers of the invention include Glu, Gln, Asp, Asn, Lys, Arg, His, Trp, Cys, Met, Gly, Ser, Thr, Tyr and the like. In some embodiments, the amino acid is Glu, Asp, Lys, Arg, Trp, Met, or Cys.

The foldamers of the invention may have more cholic acid or cholate analogs than amino acids. In some embodiments, having more cholic acid residues may to help preserve the folding properties of the foldamers. Thus, cholic acid and cholate analogs can constitute at least about 50% of the monomers in the foldamers of the invention. In other embodiments, cholic acid and cholate analogs can constitute at least about 60% or 65% or 70% or 80% of the monomers in the foldamers of the invention. However, in some embodiments the foldamers can have more amino acids than cholic acid or cholate analog monomers. Thus, the cholic acid and cholate analogs can constitute about 50% or less of the monomers in the foldamers of the invention.

Foldamer/Cholate Oligomers

The cholic acid, cholate analog and amino acid monomers described above can be used to make foldamers or cholate oligomers. The invention is therefore directed to an oligomer of a cholic acid analog of the following formula:

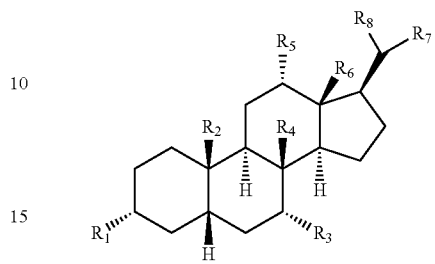

wherein the $R_1$, $R_2$, $R_3$, $R_4$, $R_5$, $R_6$, $R_7$ and $R_8$ groups are as described herein.

When the oligomer is formed from such cholic acid analogs, many of those cholic acid analogs have $R_1$ as an amine and $R_7$ as an alkylenecarboxyl so that the $R_1$ amine and $R_7$ alkylcarboxyl groups can form an amide covalently linking these cholic acid analogs together to form the oligomer.

The foldamer oligomers of the invention have at least four cholic acid, cholate analog or amino acid monomers. In some embodiments, the foldamer oligomers of the invention have at least four or five cholic acid, cholate analog or amino acid monomers. In other embodiments, the foldamer oligomers of the invention have at least five cholic acid, cholate analog or amino acid monomers. In further embodiments, the foldamer oligomers of the invention have at least six cholic acid, cholate analog or amino acid monomers. In some embodiments, the foldamer oligomers of the invention have twenty or fewer cholic acid, cholate analog or amino acid monomers. In some embodiments, the foldamer oligomers of the invention have fifty or fewer cholic acid, cholate analog or amino acid monomers. In other embodiments, the foldamer oligomers of the invention have one hundred or fewer cholic acid, cholate analog or amino acid monomers.

The invention is also directed to an oligomer of the following formula:

Xaa-(Xaa)$_m$-Xaa wherein:
m is an integer of 0-1000;
each Xaa is independently Cho or an amino acid.
In some embodiments, the oligomers have one or more Cho residues with the following formula:

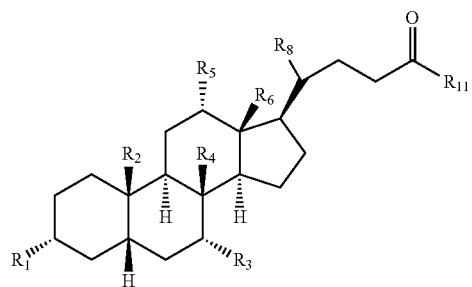

wherein the $R_1$, $R_2$, $R_3$, $R_4$, $R_5$, $R_6$, $R_7$ and $R_8$ groups are as described herein; and $R_{11}$ is a hydroxy, a solid support, a label, a linker, or a covalent bond to an $R_1$ amine of another Cho residue.

In some embodiments, $R_1$ in the oligomers can be a hydroxy, amine, a solid support, a linker or a label.

Examples of the foldamers of the invention include the following:

Cho-Cho-Glu-Cho-Cho-Glu-Cho
Cho-Glu-Cho-Cho-Cho-Glu-Cho
Glu-Cho-Cho-Cho-Cho-Glu-Cho
Glu-Cho-Cho-Cho-Cho-Cho-Glu
Cho-Glu-Cho-Cho-Cho-Glu-Cho-Cho
Cho-Glu-Cho-Cho-Cho-Glu-Cho-Cho
Cho-Glu-Cho-Glu-Cho-Glu-Cho-Glu-Cho
Cho-Cho-Arg-Cho-Arg-Cho-Cho
Cho-Cho-Arg-Cho-Cho-Arg-Cho-Cho
Dansyl-Cho-Cho-Met-Cho-Cho-Met-Cho-Cho-CONHCH$_2$CH$_2$—(OCH$_2$CH$_2$)OH
2,4-Dimethoxystiblene-Cho-Arg-Cho-Cho-Arg-Cho-Cho-Cho-Trp
Anthracene-Cho-Arg-Cho-Cho-Cho-Cho-Arg-Cho-Trp
7-Dimethylaminocoumarine-Cho-Arg-Cho-Cho-Cho-Cho-Cho-Cho-Arg-Trp
Fluorescein-Cho-Cho-Arg-Cho-Cho-Arg-Cho-Cho-Arg-Trp
Dansyl-Cho-Arg-Cho-Arg-Cho-Arg-Cho-Cho-Cho-Trp
Eosin-Cho-Arg-Cho-Arg-Cho-Arg-Cho-Arg-Cho-Cho-Trp The foldamers of the invention can readily be made using reagents, conditions and procedures like those used for making peptides. Selected cholic acid derivatives and amino acids can easily be incorporated by insertion at the desired position within the oligomer during synthesis using procedures for making peptides of selected sequences. In general, cholate analogs and amino acids are used as foldamer monomers to provide functional groups in the foldamers for interacting with agents of interest (e.g., metals, ions, drugs, small molecules, etc.). Thus, the cholate oligomers of the invention are easily made and can be used as a foldable backbone that is readily adapted for interacting with other agents and for a variety of other purposes.

Modulating Foldamer Conformation

The foldamers of the invention have a facial amphiphilicity and a natural curvature that encourages them to fold into helical structures with nanometer-sized hydrophilic cavities (see FIGS. 1 and 14). As facial amphiphiles, the α faces of cholate foldamers are hydrophilic with three hydroxyl groups, while the β face is completely hydrophobic, being all hydrocarbon. Thus, the hydroxyl groups of present cholate foldamers, which can be easily modified independent of the carboxyl tail (as described herein), can form a hydrophilic face that is easily tailored to react or interact with specific selected agents (metals, ions, drugs, small molecules, pollutants, etc.). Moreover, the curvature toward the α face creates an intrinsic preference for the present foldamer to adopt folded conformations. Such a folded conformation can enfold, envelop, or encapsulate these selected agents.

Foldamers in the folded conformation can form a corkscrew or helical conformation. In some embodiments, the foldamers helices have about 2 to 4 monomers per turn; in other embodiments the foldamers have about 2 to about 5 monomers per turn; and in further embodiments the foldamers have about 2 to about 6 monomers per turn.

Figure 17:
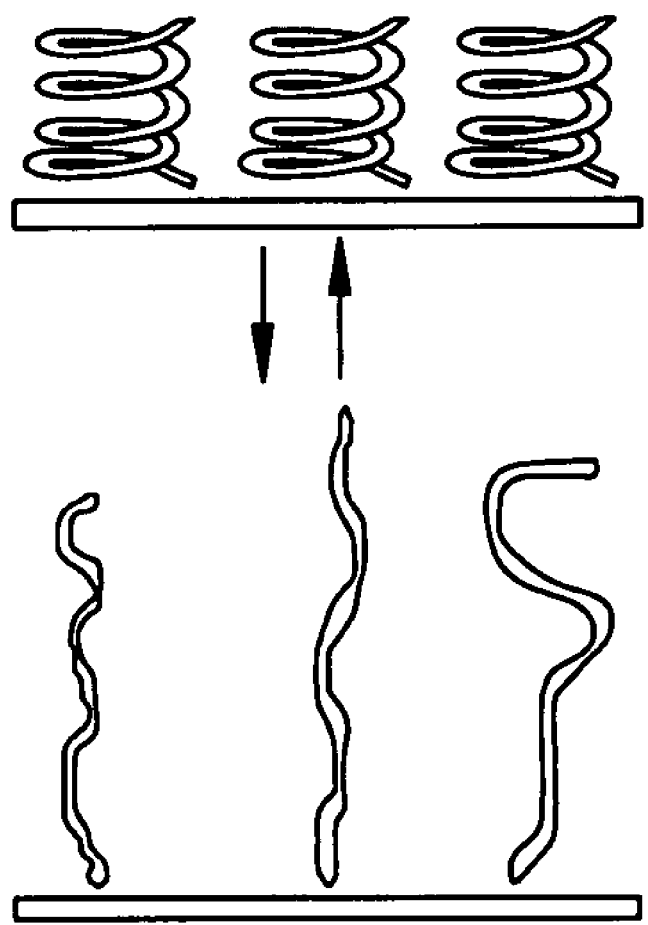
FIG. 17 shows transition between folded and unfolded immobilized oligomers of the invention.

Thus, in the extended conformation an oligomeric foldamer of the invention can have an unfolded conformation, for example, as shown in FIGS. 1, 14 and 17. However, in the folded conformation an oligomeric foldamer of the invention forms a helix, as described above and illustrated in FIGS. 1, 14 and 17.

When the foldamers consist only of cholate residues, which do not have inherent intramolecular interactions such as hydrogen bonds and π-π stacking along the backbone, folding is largely driven by solvophobic interactions and microphase separation of solvents within a nanometer-sized hydrophilic cavity. Experiments by the inventor have demonstrated that such folding is extremely sensitive to solvent changes—minute changes (<0.5%) in solvent composition can cause readily detected changes in foldamer conformation.

The foldamers can be solubilized or suspended in a variety of nonpolar or polar solvents. In some embodiments, the folded conformation of cholate-rich foldamers may be most stable in a polar solvent. In other embodiments, the folded conformation of cholate-rich foldamers may be most stable in a nonpolar solvent. In further embodiments, the folded conformation of cholate-rich foldamers may be most stable in a nonpolar solvent with a small amount of polar solvent. In general, nonpolar solvents are compounds that have low dielectric constants and are not miscible with water. Examples include benzene ($C_6H_6$), hexane ($CH_3(CH_2)_4$—$CH_3$), carbon tetrachloride ($CCl_4$), diethyl ether ($CH_3CH_2OCH_2CH_3$) and mixtures of ethyl acetate (EA) and hexane. Examples of polar solvents include water, dimethyl sulfoxide (DMSO), dimethyl formamide (DMF), formamide, formic acid, acetic acid, ethylene glycol, glycerol, acetone and alcohols. In some embodiments, the polar solvent is dimethyl sulfoxide (DMSO) or an alcohol. Examples of alcohols useful for practice of the invention include methanol, ethanol, propanol, isopropanol, t-butanol and butanol.

Like the polar solvents used in reversed micelles formed by conventional surfactants (Fendler, J. H. *Membrane Mimetic Chemistry*; Chapter 3 (Wiley: New York, 1982)), the polar solvent is used to stabilize the folded state, which resembles a reversed micelle with a hydrophilic interior and hydrophobic exterior that can enclose a few molecules of the polar solvent.

In general, in a nonpolar-polar solvent mixture, the polar solvents are present in smaller amounts than the nonpolar solvents. Thus, for example, to optimally promote folding, binding and or encapsulation the polar solvent can constitute about 0.01% to about 50% of the solvent mixture, or about 1% to about 40% of the solvent mixture, or about 2% to about 30% of the solvent mixture, or about 3% to about 20% of the solvent mixture, or about 3.5% to about 15% of the solvent mixture, or about 4% to about 10% of the solvent mixture. In some embodiments, the solvent mixture contains about 3% to about 8% of the polar solvent.

Because folding can be driven by solvophobic interactions and microphase separation of solvents within a nanometer-sized hydrophilic cavity, solvent quality/miscibility can be used to directly control the conformational stability of the foldamers. For example, DMSO is completely miscible with ethyl acetate but immiscible with hexane. Because the folded helix has a hydrophilic interior in which the polar solvent (DMSO) is expected to be enriched, a demixing of solvents must occur during folding. Such a demixing is easier in a solvent mixture with limited miscibility. This hypothesis is confirmed by experimental studies. DMSO is miscible with ethyl acetate/hexane (1/2) up to 6% by volume, but can mix with ethyl acetate/hexane (1/1) at any ratio. Therefore, folding is easier in the former solvent mixture and the stability of the folded conformation is lower in ethyl acetate/hexane (1/1) than in ethyl acetate/hexane (1/2). In fact, a foldamer with five cholate monomers (a "pentamer") completely unfolds even in 2% DMSO ethyl acetate/hexane (1/1). If miscibility of the solvents is further increased by using just DMSO and ethyl acetate, none of the oligomers tested (the pentamer, a cholate hexamer and a cholate heptamer) could fold. Thus, the solvent type and the proportion of hydrophobic and hydrophilic solvents can control foldamer folding.

One aspect of the invention is therefore a method of controlling the folding of the present foldamers in a solvent by modulating the solvent's hydrophobicity, hydrophilicity and/or miscibility of hydrophobic and hydrophilic components. Such modulating can involve changing the ratio of a hydrophobic or nonpolar solvent component to the hydrophilic or polar solvent component.

Another factor that can be used to control the folding of the present foldamers is temperature. Thus, in general, folding is stabilized when the temperature is reduced and unfolding is promoted when the temperature is increased. The length, amino acid content and the type and number of bound analytes of the foldamer can modulate the temperature at which the foldamers change their conformation.

When amino acids and cholic acid analogs are incorporated into the present foldamers, factors other than the temperature and/or solvent can modulate the conformation of the present foldamers. Thus, amino acids can be incorporated into the foldamers that can stabilize or destabilize the folded or unfolded conformational states of the foldamers. Moreover, these amino acids can bind to analytes not only to help retain the analyte within the hydrophilic cavity or pore of the foldamer but also to stabilize the folded conformation of the foldamer. Under these circumstances, changes in pH, ion concentration, solute concentration, and/or the presence of reducing or oxidizing agents can influence the conformation of the foldamers.

Thus, according to the invention, the present foldamers that undergo highly sensitive conformational changes are useful for sensing a variety of analytes as well as for detecting changes in the environment.

Delivery Systems and Compositions

Another aspect of the invention is a delivery system that includes a foldamer of the invention with selected active agent. The active agent is folded within, enveloped within or encapsulated within the hydrophilic cavity of the foldamer to form a foldamer delivery system. In some embodiments, the foldamer delivery system is further encapsulated within a liposome or formulated with a surfactant.

Any active agent can be encapsulated within the foldamer delivery systems of the invention. Such active agents include, pharmaceutically active agents, drugs, metals, minerals, ions, buffers, fertilizers, pesticides, herbicides and the like.

Examples of pharmaceutically active agents or drugs that can be encapsulated into the foldamers of the invention include: analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like); anesthetics (e.g., halothane, isoflurane, methoxyflurane, propofol, thiobarbiturates, xenon and the like); antiasthmatics (e.g., Azelastine, Ketotifen, Traxanox, and the like); antibiotics (e.g., neomycin, streptomycin, chloramphenicol, cephalosporin, ampicillin, penicillin, tetracycline, and the like); antidepressants (e.g., nefopam, oxypertine, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like); antidiabetics (e.g., biguanides, hormones, sulfonylurea derivatives, and the like); antifungal agents (e.g., griseofulvin, keoconazole, amphotericin B, Nystatin, candicidin, and the like); antihypertensive agents (e.g., propanolol, propafenone, oxyprenolol, nifedipine, reserpine, trimethaphan camsylate, phenoxybenzamine hydrochloride, pargyline hydrochloride, deserpidine, diazoxide, guanethidine monosulfate, minoxidil, rescinamine, sodium nitroprusside, rauwolfia serpentina, alseroxylon, phentolamine mesylate, reserpine, and the like); anti-inflammatory agents (e.g., (non-steroidal) indomethacin, naproxen, ibuprofen, ramifenazone, piroxicam, (steroidal) cortisone, dexamethasone, fluazacort, hydrocortisone, prednisolone, prednisone, and the like); antineoplastics agents (e.g., adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, and the like); antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, dantrolene, and the like); immunosuppressive agents (e.g., cyclosporine, azathioprine, mizoribine, FK506 (tacrolimus), and the like); antimigraine agents (e.g., ergotamine tartrate, propanolol hydrochloride, isometheptene mucate, dichloralphenazone, and the like); sedatives/hypnotics (e.g., barbiturates (e.g., pentobarbital, pentobarbital sodium, secobarbital sodium), benzodiazepines (e.g., flurazepam hydrochloride, triazolam, tomazeparm, midazolam hydrochloride, and the like); antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like)); antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like); antimanic agents (e.g., lithium carbonate); antiarrhythmics (e.g., amiodarone, related derivatives of amiodarone, bretylium tosylate, esmolol hydrochloride, verapamil hydrochloride, encamide hydrochloride, digoxin, digitoxin, mexiletine hydrochloride, disopyramide phosphate, procainamide hydrochloride, quinidine sulfate, quinidine gluconate, quinidine polygalacturonate, flecamide acetate, tocamide hydrochloride, lidocaine hydrochloride, and the like); antiarthritic agents (e.g., phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, and the like); antigout agents (e.g., colchicine, allopurinol, and the like); anticoagulants (e.g., heparin, heparin sodium, warfarin sodium, and the like); thrombolytic agents (e.g., urokinase, streptokinase, altoplase, and the like); antifibrinolytic agents (e.g., aminocaproic acid); hemorheologic agents (e.g., pentoxifylline); antiplatelet agents (e.g., aspirin, empirin, ascriptin, and the like); anticonvulsants (e.g., valproic acid, divalproate sodium, phenyloin, phenyloin sodium, clonazepam, primidone, phenobarbitol, phenobarbitol sodium, carbamazepine, amobarbital sodium, methsuximide, metharbital, mephobarbital, mephenyloin, phensuximide, paramethadione, ethotoin, phenacemide, secobarbitol sodium, clorazepate dipotassium, trimethadione, and the like); antiparkinson agents (e.g., ethosuximide, and the like); antihistamines/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimprazine tartrate and the like); agents useful for calcium regulation (e.g., calcitonin, parathyroid hormone, and the like); antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like); antiviral agents (e.g., interferon gamma, zidovudine, amantadine hydrochloride, ribavirin, acyclovir, and the like); antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), prythronycins, penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like); anti-infectives (e.g., GM-CSF); bronchodilators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g., aminophylline, dyphylline, metaproterenol sulfate, aminophylline), mast cell stabilizers (e.g., cromolyn sodium), inhalant corticosteroids (e.g., flurisolidebeclomethasone dipropionate, beclomethasone dipropionate monohydrate), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like); hormones (e.g., androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebutate, prednisolone acetate, prednisolone sodium phosphate, hydrocortisone sodium succinate, and the like), thyroid hormones (e.g., levothyroxine sodium) and the like), and the like; hypoglycemic agents (e.g., human insulin, purified beef insulin, purified pork insulin, glyburide, chlorpropamide, glipizide, tolbutamide, tolazamide, and the like); hypolipidemic agents (e.g., clofibrate, dextrothyroxine sodium, probucol, lovastatin, niacin, and the like); proteins (e.g., DNase, alginase, superoxide dismutase, lipase, and the like); nucleic acids (e.g., sense or anti-sense nucleic acids encoding any therapeutically useful protein, including any of the proteins described herein, and the like); agents useful for erythropoiesis stimulation (e.g., erythropoietin); antiulcer/antireflux agents (e.g., famotidine, cimetidine, ranitidine hydrochloride, and the like); antinauseants/antiemetics (e.g., meclizine hydrochloride, nabilone, prochlorperazine, dimenhydrinate, promethazine hydrochloride, thiethylperazine, scopolamine, and the like); oil-soluble vitamins (e.g., vitamins A, D, E, K, and the like); as well as other drugs such as mitotane, visadine, halonitrosoureas, anthrocyclines, ellipticine, and the like.

The delivery systems of the invention can be formulated as pharmaceutical compositions and administered to a mammal, such as a human patient in a variety of forms adapted to the chosen route of administration. Routes for administration include, for example, oral, parenteral, subcutaneous, intramuscular, and intraperitoneal routes.

The delivery systems and foldamers suitable for injection or infusion can include sterile aqueous solutions or dispersions comprising the delivery systems with the active agent that can be adapted for administration by encapsulation in liposomes. In further embodiments the foldamers can be formulated with a surfactant to increase the solubility of the foldamer, which can have a hydrophobic surface do to the cholic acid residues. Suitable long chain surfactants can be selected from the group known as organic or inorganic surfactant pharmaceutical excipients. Preferred surfactants include nonionic and anionic surfactants.

Representative examples of long chain or high molecular weight (>1000) surfactants include gelatin, casein, lecithin (phosphatides), gum acacia, cholesterol, tragacanth, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, microcrystalline cellulose, magnesium aluminum silicate, triethanolamine, polyvinyl alcohol, and polyvinylpyrrolidene (PVP). The low molecular weight (<1000) include stearic acid, benzalkonium chloride, calcium stearate, glycerol monostearate, cetostearyl alcohol, cetomacrogol emulsifying wax, and sorbitan esters. Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Sterile injectable solutions are prepared by incorporating the agents into the foldamers in the required amount in the appropriate solvent with various of the other ingredients, as required. The composition can be sterilized before or after assembly.

The desired dose may conveniently be presented in a single dose or as divided doses administered at appropriate intervals, for example, as two, three, four or more sub-doses per day. The sub-dose itself may be further divided, for example, into a number of discrete loosely spaced administrations; such as multiple oral, intraperitoneal or intravenous doses.

In some instances, the delivery systems can be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, they may be combined with one or more excipients and used in the form of ingestible tablets, buccal tablets, troches, capsules, elixirs, suspensions, syrups, wafers, and the like. Such compositions and preparations may contain at least 0.1% of active compound. The percentage of the compositions and preparations may, of course, be varied. The amount of compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Useful solid carriers include finely divided solids such as talc, clay, microcrystalline cellulose, silica, alumina and the like. Useful liquid carriers include water, alcohols or glycols or water-alcohol/glycol blends, in which the delivery systems can be dissolved or dispersed at effective levels, optionally as indicated above with the aid of non-toxic surfactants. Adjuvants such as fragrances and additional antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

The pharmaceutical compositions of the invention can include foldamer delivery systems of the invention with an effective amount of at least one active agent, or two or more different active agents. These compositions also include a pharmaceutically effective carrier.

Detection of Folding and/or Binding

A variety and/or a combination of different techniques can be used to detect foldamer folding and/or binding of a metal, ion, drug, small molecule, pollutant, and the like. For example, folding may be monitored simply by the change of UV absorption or fluorescence of fluorophores attached to the foldamers. In some embodiments the fluorophore employed is an environmentally sensitive fluorophore. Such environmentally sensitive fluorophores can detect changes in the hydrophobicity/hydrophilicity, pH, ion concentration, and the like of the solvent or surrounding environment. For example, folding of the present oligomers creates hydrophilic cavities and, as a result, enriches polar solvents around the fluorophore, which is typically sensitive to local solvent composition.

In some embodiments, measurement of fluorescence variations is used to detect folding of the foldamers and/or binding of other atoms, ions and molecules. Fluorophore-coupled folding assays use a donor and an acceptor fluorophore, for example, on the opposite ends of the foldamer. Upon folding, the two fluorophores are brought closer to each other by the folding of the foldamer so that fluorescence resonance energy transfer (FRET) occurs from the donor to the acceptor. When the foldamer unfolds, the donor and acceptor fluorophores are separated, FRET does not occur anymore and fluorescence emission from the donor increases at the expense of fluorescence emission from the acceptor. As shown in the Examples provided herein, FRET can not only distinguish the compact/folded and extended/unfolded conformations, but also probe the periodicity of the folded structure. Thus, FRET is a useful technique for detecting the conformation of the present foldamers.

A variety of donor and acceptor fluorophores can be used for FRET detection of conformational changes in the present foldamers. For example, a naphthalene-dansyl donor-acceptor pair can be used. In some embodiments, the naphthalene-dansyl donor-acceptor pair is useful for detecting elongated foldamers because the $R_0$ value (2.2 nm) for this pair allows easy distinction of distances between 1.5 nm (transfer efficiency E=0.9) and 3.2 nm (E=0.1). If the distance to be measured is outside this range, many other donor-acceptor pairs with broad ranges of $R_0$ values (e.g., 2-9 nm) are available. Stryer, L. Fluorescence Energy Transfer as a Spectroscopic Ruler. *Annu. Rev. Biochem.* 47, 819-846 (1978); Selvin, P. R. Fluorescence Resonance Energy Transfer. *Methods Enzymol.* 246, 300-334 (1995); Lakowicz, J. R. Energy Transfer, in *Principles of Fluorescence Spectroscopy,* 2nd Ed.; Chap. 13 (Kluwer: New York, 1999). For example, the pyrenene-Coumarin donor-acceptor pair has a $R_0$ value of 3.9 nm, while the NBD-fluorescein pair has a $R_0$ value of 4.8 nm.

Labeling of the foldamers is straightforward because they have useful functional groups on their termini (e.g., amino and carboxyl groups), and standard derivatizing procedures exist with for label attachment. For example, fluorophores with reactive functional groups for easy attachment are available from Molecular Probes.

Fluorescence quenching is also useful because enhanced quenching by hydrophilic quencher (e.g., 11) is an evidence for the presence of hydrophilic cavities.

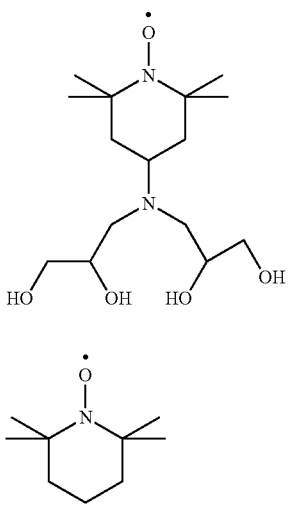

11

12

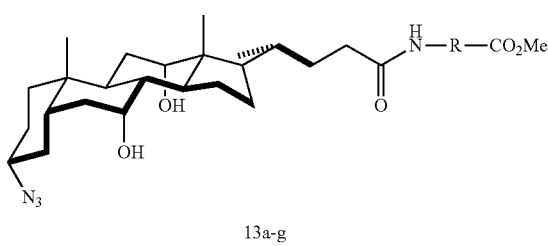

13a-g

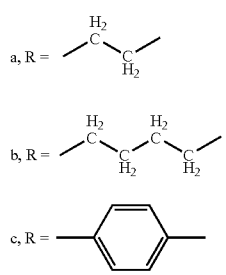

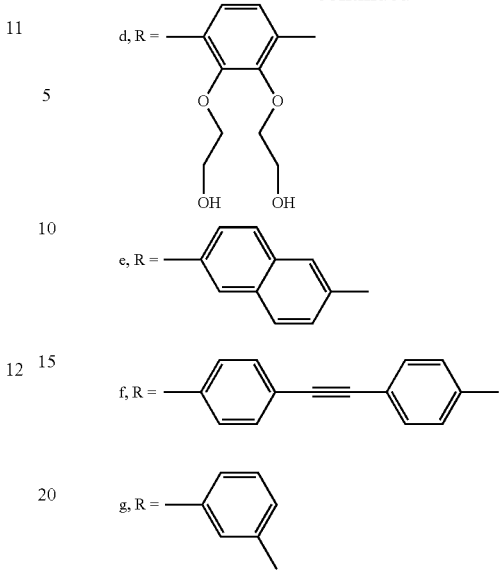

-continued

While circular dichroism (CD) spectroscopy can be used to monitor the conformational changes of polypeptides, CD cannot be used for detecting conformation changes in foldamers that contain only cholate, because the solvents needed for folding (e.g., $CCl_4$, DMSO, ethyl acetate, etc.) absorb strongly between 190-220 nm, which is where the amide moiety absorbs light. Solvent absorption is much less of a problem for the present foldamers with aromatic spacers (13c-f).

Because the amide bonds in the cholate oligomers differ significantly from those in natural peptides, it is not certain exactly what type of conformational changes have occurred when observing changes in CD. However, with CD spectroscopy, the conformational changes can be quickly correlated with the solvent composition. And, in connection with the fluorescence studies, signature CD patterns for the folded and unfolded conformations can be identified. In a longer term, this is a much faster and easier way to study conformations than fluorescence because no fluorescent labeling is necessary.

NMR techniques may also be used for detecting conformational changes in foldamers. While, NOE-based methods such as NOSEY are problematic because of severe overlaps of the proton signals in the cholate oligomers, a useful method is pulse-gradient spin-echo (PGSE) NMR, which can measure translational diffusion coefficients of molecules in solution (note that an unfolded conformer should diffuse more slowly than the folded conformer).

Thus, a variety of methods and reagents can be used be to detect conformational changes in foldamers.

The invention will be described with reference to the following non-limiting examples.

Example 1

Materials and Methods

This Example shows materials and methods for making oligomeric cholates. Briefly, the hydroxyl at the C-3 of cholic acid was converted to an amino group, and the resulting amino-functionalized cholic acid was used as a monomer to prepare amide-linked oligomeric cholates.

Materials

Anhydrous tetrahydrofuan (THF) and methylene chloride were dried by passage through a column of activated alumina under compressed nitrogen. Cholic acid was crystallized from 95% ethanol. Methyl sulfoxide (DMSO, spectrophotometric grade, 99.9%) was purchased from Acros. Methanol (HPLC grade) and hexanes (HPLC grade) were purchased from Fisher Scientific. Carbon tetrachloride (HPLC grade) was purchased from Aldrich. All other reagents and solvents were of A.C.S. certified grade or higher, and were used as received from commercial suppliers. All glassware and syringes were dried in an oven at least overnight prior to use. Routine $^1H$ and $^{13}C$ NMR spectra were recorded on a Varian VXR-300 and VXR-400 spectrometer. MALDI-TOF mass was recorded on a Thermobioanalysis Dynamo mass spectrometer. ESI-MS mass was recorded on Shimadzu LCMS-2010 mass spectrometer. UV-visible spectra were recorded at ambient temperature on an HP 8452 Spectrometer. Fluorescence spectra were recorded at ambient temperature on a Varian Cary Eclipse Fluorescence spectrophotometer.

Data Analysis

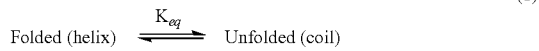

$$\text{Folded (helix)} \xrightleftharpoons{K_{eq}} \text{Unfolded (coil)} \tag{1}$$

According to the two-state model, at any given concentration of the denaturant (i.e., DMSO), only the folded and unfolded conformations are present and their fractions are represented by $f_F$ and $f_U$. Fraction of the unfolded conformation can be calculated by:

$$f_U = (I_F - I)/(I_F - I_U) \tag{2}$$

in which I is the observed emission intensity of the acceptor in a given foldamer, $I_F$ is the emission intensity of the acceptor in the fully folded conformer, and $I_U$ is the emission intensity of the acceptor in the fully unfolded conformer. The equilibrium constant ($K_{eq}$) and the free energy ($\Delta G$) for the folding reaction can be calculated using $$\Delta G = RT \ln K_{eq} = -RT \ln(f_U/f_F) = -RT \ln[f_U/(1-f_U)] \tag{3}$$

In order to calculate fractions of the unfolded conformations, both $I_F$ and $I_U$ must be known for different foldamers. The emission intensity of the acceptor in the 1:1 mixture of the monomer A 8 (MA) and monomer D 9(MD) should be good approximations for $I_U$ since the emission intensity of the longer foldamers (e.g., pentamer-DA 5 (PDA)) does converge to that of the (MA+MD) mixture upon unfolding. The value of $I_F$, on the other hand, cannot be obtained directly because none of the three foldamers seem to be fully folded under the initial condition of 1% DMSO.

In general, to obtain the values of $I_F$ for PDA, hexamer-DA 6 (HXDA), and heptamer-DA 7 (HPDA), it is useful to first make an assumption for $f_U$ (e.g., $f_U$=0.1 for the HPDA) in 1% DMSO and use it to calculate the corresponding value of $I_F$, which is designated $I_{F(1)}$. Using $I_{F(1)}$, the first set of $f_{U(1)}$ can be calculated at different DMSO percentages according to equation 2. In the two-state model, the free energies are linearly related to the concentration of denaturant (i.e., DMSO):

$$\Delta G = \Delta G_0 - m[DMSO] \tag{4}$$

in which $\Delta G_0$ is the free energy for the folding reaction in the absence of denaturant and m measures how sensitive the folding equilibrium is toward DMSO percentage. From equations 2, 3, and 4, the following equation 5 can be obtained, where equation 5 describes the relationship between $f_U$ and DMSO percentage:

$$f_U = 1/\{1 + 1/\exp[-(\Delta G_0 - m[DMSO])/RT]\} \tag{5}$$

As a result, the initial values of $\Delta G_0$ and m (which are designated as $\Delta G_{0(1)}$ and $m_1$) can be obtained by nonlinear least-squares fitting to the first set of $f_{U(1)}$. The resulting $\Delta G_{0(1)}$ and $m_1$ are used to calculate the refined value of $I_{F(2)}$ using equations 5 and 2. This process is repeated as long as there is a fairly large difference between the entering $I_{F(n)}$ value and the resulting $I_{F(n+1)}$ value. In general, fitting of the data improves over several rounds of refinement. The refinement is stopped in the end when the values of $I_{F(n)}$ and $I_{F(n+1)}$ are within 1% of each other and are taken as the final value of $I_F$.

In such data processing, it is assumed that $I_F$ was independent of DMSO percentage. Such an assumption is expected to underestimate the stability of the cholate foldamers. This is because the emission of MA is shown to be slightly quenched by DMSO—the emission intensity decreases by about 20% over 1-5% DMSO. By assuming a constant $I_F$ value in all the solvents, we have attributed the decrease of the acceptor emission solely to unfolding, yet the decrease is actually caused by both unfolding and, to a smaller degree, by the increasing DMSO.

Synthetic Procedures

Synthetic procedures
A scheme for synthesizing cholate oligomers is provided below.
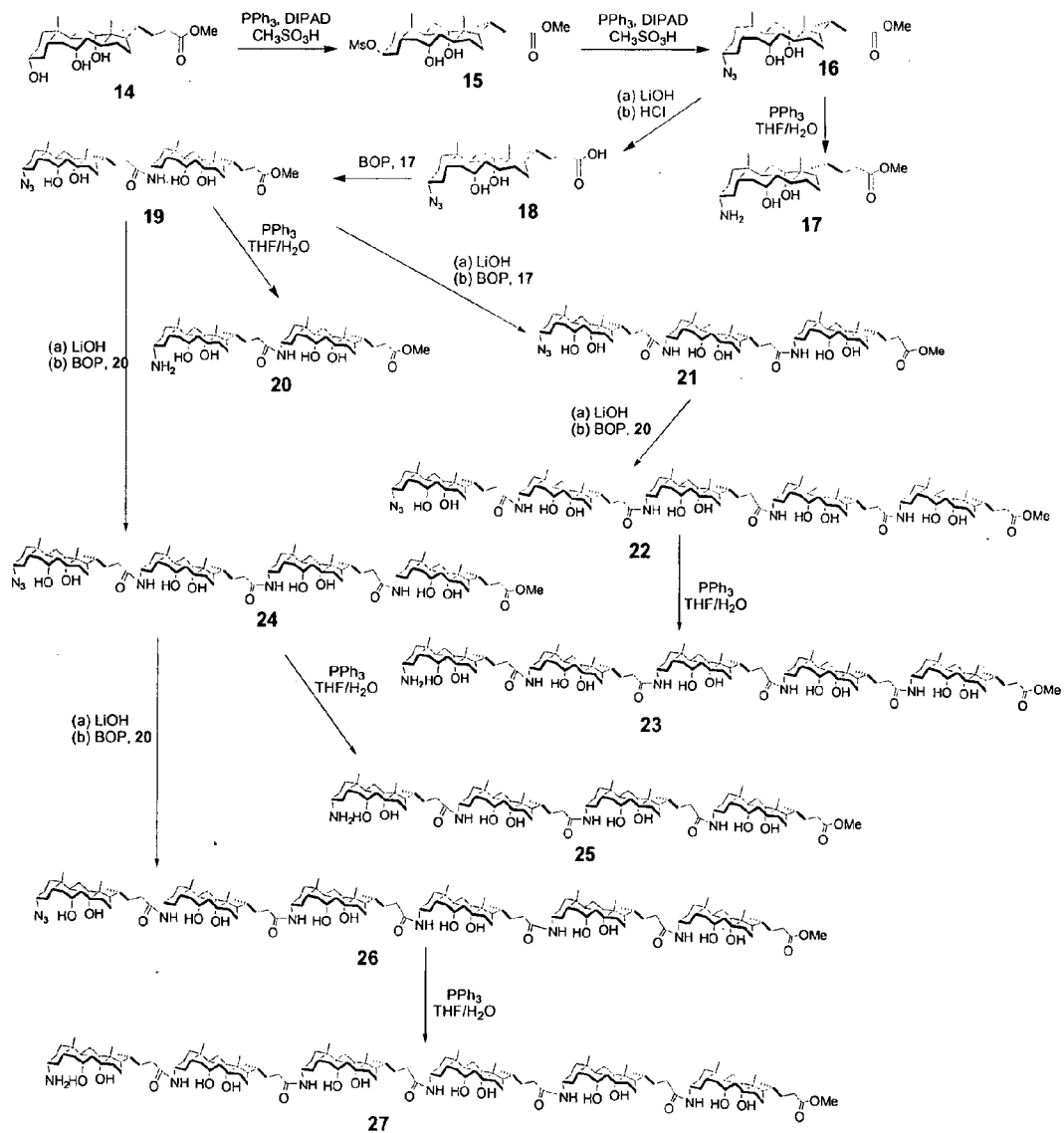

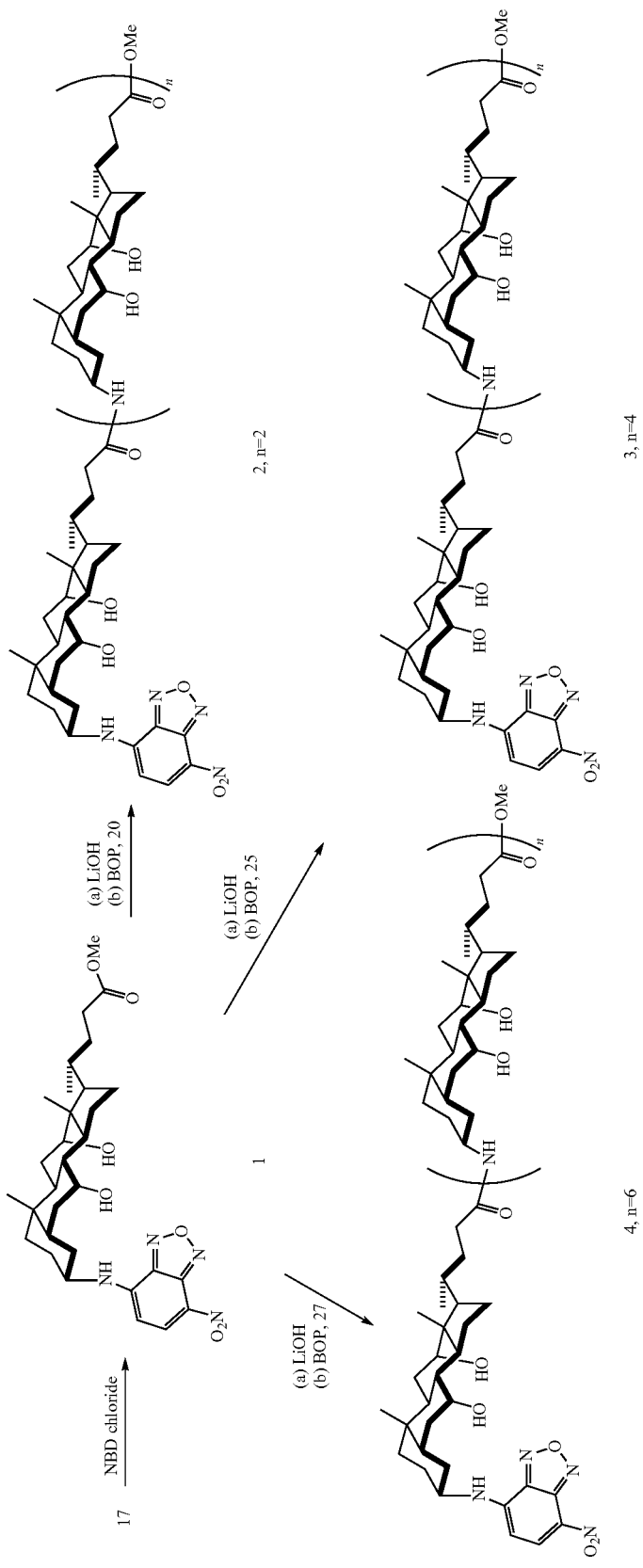
A scheme for synthesizing NBD-labeled foldamers.

Synthesis of donor-acceptor-labeled foldamers.
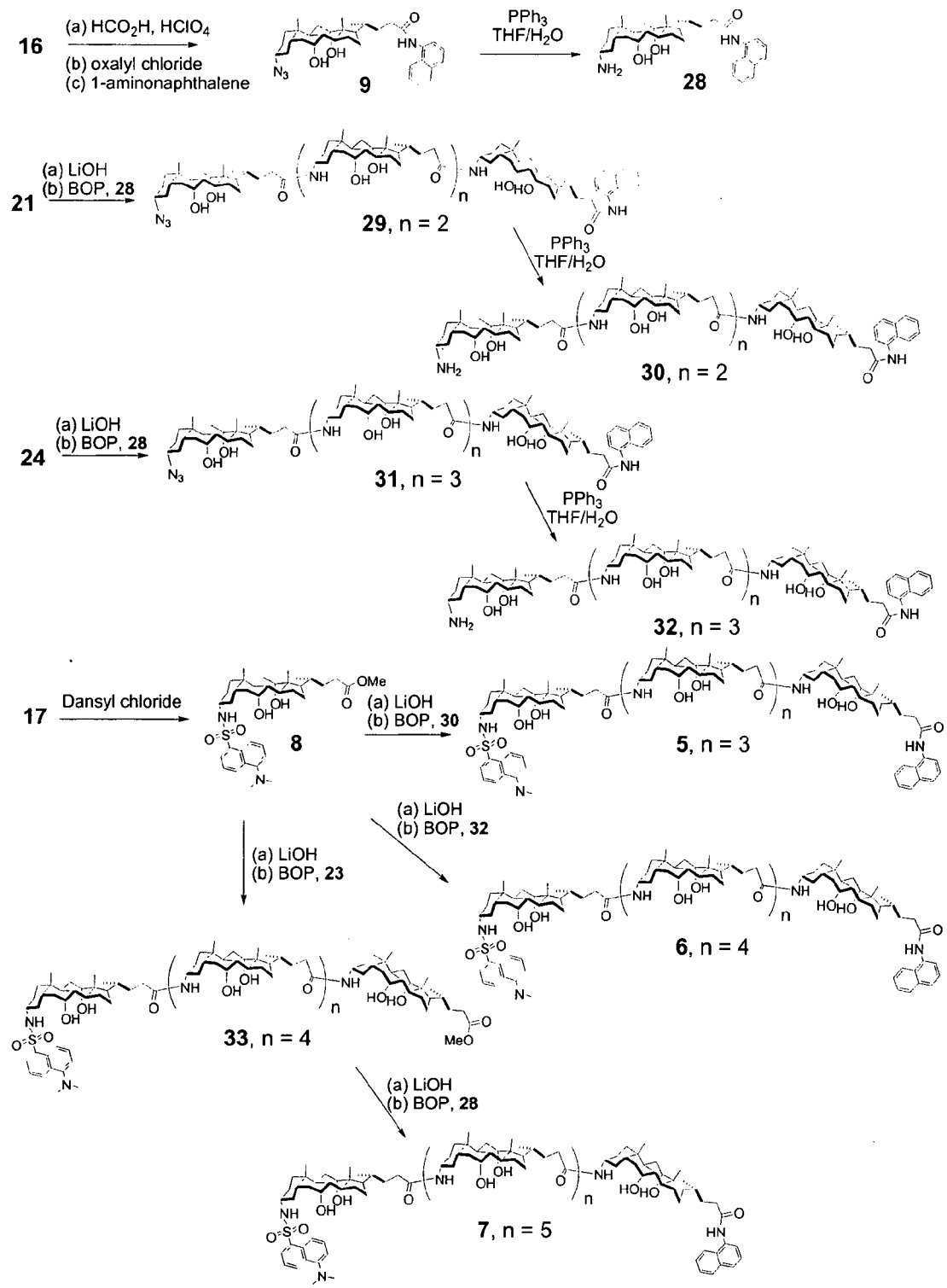

Procedure A—hydrolysis of the methyl ester. The methyl ester (1 mmol) was dissolved in methanol (5 mL) and was stirred with 2 M LiOH (5 mL, 10 mmol) at room temperature. Reaction was monitored by thin layer chromatography (TLC) and was complete in 5-24 h. Upon completion, the reaction mixture was quenched with 2 N HCl until pH=4-5. The solid was collected by suction filtration, washed with water, and dried under vacuum. The acid was generally used in the following step (i.e., amide coupling) without further purification.

Procedure B—reduction of the azide. The azide (1 mmol) and $PPh_3$ (1.5 mmol) were stirred in THF (5 mL) and $H_2O$ (0.1 mL) at 50° C. Reaction was monitored by TLC and was complete in 10-24 h. Solvents were removed by rotary evaporation. The residue was purified by column chromatography over silica gel.

Procedure C—amide coupling with BOP. The acid (1 mmol), the amine (1 mmol), and benzotriazol-1-yloxytris (dimethylamino) phosphonium hexafluorophosphate (BOP, 1.2 mmol) were dissolved in anhydrous DMF (3 mL). N,N-Diisopropylethylamine (DIPEA, 3 mmol) was added. The reaction mixture was stirred at room temperature (for lower oligomers) or 50° C. (for higher oligomers) for 10-42 h. The solvent was removed in vacuo. The residue was triturated with $CH_3CN$/ethyl acetate and was purified by column chromatography over silica gel.

Compound 16. (See, Davis, A. P.; Dresen S.; Lawless, L. J. Tetrahedron Lett. 1997, 38, 4305-4308.) Methanesulfonic acid (3.2 mL, 7.81 mmol) was added via a syringe to a solution of methyl cholate 2 (10.0 g, 24 mmol) and $PPh_3$ (18.8 g, 72 mmol) in anhydrous THF (120 mL). The reaction mixture was warmed to 40-50° C. Diisopropyl azodicarboxylate (14.0 mL, 72 mmol) was added drowse via a syringe over a 15 minute period. The mixture was stirred for 24 h at 40-50° C. under $N_2$. The mixture was cooled to room temperature and the white solid (mostly triphenyphosphine oxide) was removed by filtration. The filtrate was concentrated in vacuo and was purified by flash chromatography over silica gel using EtOAc/hexane (3:1) as the eluents to afford a viscous oil 3 (slightly impure). The oil was dissolved in 1,3-dimethyl-3,4,5,6-tetrahydro-2(1H)-pyrimidinone (DMPU, 50 mL). Sodium azide (4.7 g, 72 mmol) was added. The reaction mixture was stirred at 50° C. for 9 h. The mixture was poured into water (100 mL) and was extracted with ethyl acetate (2×50 mL). The combined organic phase was washed with water, dried over $MgSO_4$, filtered, concentrated by rotary evaporation, and purified by column chromatography over silica gel using EtOAc/hexane (1:4) as the eluents to afford a viscous oil (4.59 g, 45% yield). $^1$H NMR (300 MHz, $CDCl_3$, TMS, δ): 3.99 (s, 1H), 3.86 (s 1H), 3.67 (s, $CO_2CH_3$, 3H), 3.09-3.22 (m, 1H), 1.34-2.36 (series of m, 26H), 0.96-0.98 (d, J=8.7 Hz, 3H), 0.91 (s, 3H), 0.69 (s, 3H). C NMR (75 MHz, CDCl, δ): 175.04, 73.23, 68.46, 61.51, 51.73, 47.42, 46.75, 42.11, 42.03, 39.59, 35.66, 35.56, 35.50, 34.97, 34.77, 31.24, 31.01, 28.40, 27.71, 27.02, 26.75, 23.40, 22.77, 17.52, 12.68.

Compound 17. (See, Lawless, L. J.; Blackburn, A. G.; Ayling, A. J.; Perez-Payan, M. N.; Davis, A. P J. Chem. Soc., Perkin Trans. 12001, 1329-1341.)

Compound 17 was prepared by the reduction of 16 (Procedure B), and was purified by column chromatography over silica gel using ethyl acetate and MeOH/$Et_3$N (20:1) as the eluents (81% yield). $^1$H NMR (300 MHz, $CDCl_3$, δ): 3.95 (s, 1H), 3.89 (s, 1H), 3.56 (s, $CO_2CH_3$, 3H), 2.54-2.37 (br, 1H), 2.32-1.05 (series of m, 28H), 1.03 (d, 3H), 0.98 (s, 3H), 0.67 (s, 3H). $^{13}$C NMR (75 MHz, $CDCl_3$, δ): 174.90, 72.88, 68.08, 51.96, 51.56, 47.07, 46.51, 42.17, 41.86, 40.54, 39.65, 36.19, 35.43, 34.95, 34.84, 31.39, 31.17, 30.98, 28.45, 27.61, 26.50, 23.36, 22.81, 17.39, 12.59.

Compound 19. Compound 19 was obtained by coupling between hydrolyzed 16 and amine 17 (Procedures A and C). The product was purified by precipitation into $CH_3CN$ (94% yield). $^1$H NMR (300 MHz, $CDCl_3$/$CD_3OD$=1:1, δ): 7.79 (s, 1H), 3.95 (d, 2H), 3.81 (d, 2H), 3.66 (s, $CO_2CH_3$, 3H), 3.58-3.49 (m, 1H), 3.26-3.17 (m, 1H), 2.49-1.50 (series of m, 48H), 1.02 (d, 6H), 0.96 (d, 6H), 0.70 (d, 6H). $^{13}$C NMR (75 MHz, $CDCl_3$/$CD_3OD$=1:1, δ): 176.31, 175.50, 73.73, 73.59, 68.71, 62.46, 51.93, 50.49, 47.67, 47.29, 47.20, 47.19, 43.10, 42.99, 42.71, 42.58, 40.48, 40.40, 37.09. 36.81, 36.48, 36.39, 36.34, 35.73, 35.54, 35.40, 33.53, 32.77, 31.88, 31.70, 29.24, 29.07, 28.42, 28.11, 27.55, 27.52, 27.40, 23.93, 23.19, 23.05, 17.66, 17.47, 12.90, 12.85. MALDI-TOFMS (m/z): $[M+Na]^+$ calcd for $C_{49}H_{80}N_4NaO_7$, 860.17; found, 860.74.

Compound 20. Compound 20 was prepared by the reduction of 19 (Procedure B), and was purified by precipitation into $CH_3CN$ (88% yield). $^1$H NMR (300 MHz, $CDCl_3$/$CD_3OD$=1:1, δ): 3.92 (s, 2H), 3.79 (s, 2H), 3.64 (s, $CO_2CH_3$, 3H), 3.55 (br, 1H), 2.58 (br, 1H), 2.37-0.82 (m, 60H), 0.66 (d, 6H). $^{13}$C NMR (75 MHz, $CDCl_3$/$CD_3OD$=1:1, δ): 175.04, 174.01, 72.46, 72.39, 67.54, 50.90, 49.03, 48.81, 46.46, 46.23, 45.96, 45.88, 45.36, 41.56, 41.34, 41.27, 39.05, 38.95, 37.81, 35.73, 35.46, 35.29, 35.19, 35.02, 34.30, 34.25, 34.09, 32.68, 31.53, 30.58, 28.63, 27.79, 27.67, 26.80, 26.06, 22.70, 22.01, 21.94, 16.53, 16.40, 11.79, 11.77. MALDI-TOFMS (m/z): $[M+Na]^+$ calcd for $C_{49}H_{82}N_2NaO_7$, 834.17; found, 834.92. $[M+H]$ calcd for $C_{49}H_{83}N_2O_7$ 812.18; found, 812.79.

Compound 21. Compound 21 was obtained by coupling between hydrolyzed 19 and amine 17 (Procedures A and C). The product was purified by column chromatography over silica gel using $CH_2Cl_2$/MeOH (15:1) as the eluents (91% yield). $^1$H NMR (300 MHz, $CDCl_3$/$CD_3OD$=1:1, δ): 3.96 (m, 3H), 3.83 (m, 3H), 3.68 (s, $CO_2CH$, 3H), 3.62 (br, 2H), 3.25 (br, 1H), 2.42-1.15 (series of m, 72H), 1.12 (m, 9H), 0.96 (m, 9H), 0.69 (m, 9H). $^{13}$C NMR (75 MHz, $CDCl_3$/$CD_3OD$=1:1, δ): 175.08, 174.04, 173.97, 72.51, 72.42, 67.62, 67.44, 61.18, 50.99, 49.13, 49.05, 46.54, 46.09, 46.04, 45.99, 45.95, 41.60, 41.37, 41.27, 39.10, 39.01, 35.76, 35.47, 35.32, 35.15, 35.08, 34.53, 34.31, 34.16, 33.00, 32.36, 31.68, 31.55, 30.67, 30.61, 27.82, 27.79, 27.17, 26.87, 26.19, 22.74, 22.08, 22.02, 19.99, 18.11, 16.63, 16.59, 16.50, 13.63, 11.87, 11.84. MALDI-TOFMS (m/z): $[M+Na]^+$ calcd for $C_{73}H_{119}N_5NaO_{10}$, 1249.74; found, 1251.84.

Compound 22. Compound 22 was obtained by coupling between hydrolyzed 21 and amine 20 (Procedures A and C). The product was purified by column chromatography over silica gel using EtOAc/MeOH (12:1) as the eluents (54% yield). $^1$H NMR (300 MHz, $CDCl_3$/$CD_3OD$=1:1, δ): 7.59 (m, 1H), 3.96 (m, 5H), 3.83 (m, 5H), 3.68 (s, $CO_2CH_3$, 3H), 3.55 (br, 4H), 3.20 (br, 1H), 2.45-1.03 (series of m, 135H), 0.93 (m, 15H), 0.70 (m, 15H). $^{13}$C NMR (75 MHz, $CDCl_3$/$CD_3OD$=1: 1, δ): 175.16, 174.11, 174.02, 72.58, 67.69, 67.51, 61.22, 51.04, 49.18, 46.12, 46.04, 41.64, 41.40, 41.31, 39.12, 39.06, 35.81, 35.51, 35.32, 35.10, 34.56, 34.37, 34.32, 34.19, 33.18, 32.39, 31.70, 31.37, 30.70, 30.65, 27.80, 27.19, 26.91, 26.21, 22.78, 22.10, 22.08, 16.62, 16.54, 11.91, 11.88. MALDI-TOFMS (m/z): $[M+Na]^+$ calcd for $C_{121}H_{197}N_7NaO_{16}$, 2028.89; found, 2031.27.

Compound 23. Compound 23 was prepared by the reduction of 22 (Procedure B), and was purified by column chromatography over silica gel using ethyl acetate and MeOH/$Et_3$N (20:1) as the eluents (78% yield). $^1$H NMR (300 MHz, $CDCl_3$/$CD_3OD$=1:1, δ): 7.58 (m, 1H), 3.96 (m, 5H), 3.83 (m, 5H), 3.68 (s, $CO_2CH_3$, 3H), 3.55 (br, 4H), 3.20 (br, 1H), 2.45-1.03 (m, 135H). 0.93 (m, 15H), 0.70 (m, 15H). $^{13}$C NMR (75 MHz, CDCl$_3$/CD$_3$OD=1:1, δ): 175.09, 174.04, 173.95, 72.51, 67.63, 67.44, 61.16, 50.97, 49.11, 46.12, 46.06, 45.97, 41.58, 41.34, 41.24, 39.12, 38.99, 35.74, 35.45, 35.26, 35.04, 34.49, 34.30, 34.13, 33.07, 32.33, 31.64, 31.31, 30.63, 30.61, 27.73, 27.13, 26.85, 26.14, 22.71, 22.04, 22.03, 16.56, 16.48, 11.84, 11.82. MALDI-TOFMS (m/z): [M+Na]$^+$ calcd for C$_{121}$H$_{199}$N$_5$NaO$_{16}$, 2002.89; found 2001.61. [M+H]$^+$ calcd for C$_{12}$H$_{200}$N$_5$O$_{16}$, 1980.90; found, 1983.64.

Compound 24. Compound 24 was obtained by coupling between hydrolyzed 19 and amine 20 (Procedures A and C). The product was purified by column chromatography over silica gel using EtOAc/MeOH (15:1) as the eluents (74% yield). NMR (300 MHz, CDCl$_3$/CD$_3$OD=1:1, δ): 3.96 (m, 4H), 3.82 (m, 4H), 3.67 (s, CO$_2$CH$_3$, 3H), 3.52 (br, 3H), 3.33 (br, 1H), 2.43-1.02 (series of m, 108H), 0.93 (m, 12H), 0.71 (m, 12H). $^{13}$C NMR (75 MHz, CDCl$_3$/CD$_3$OD=1:1, δ): 176.16, 175.29, 175.22, 73.58, 73.49, 68.62, 62.28, 55.55, 51.91, 50.41, 50.36, 50.28, 48.66, 47.62, 47.58, 47.15, 47.10, 47.07, 47.04, 42.86, 42.77, 42.50, 42.41, 40.26, 40.18, 36.84, 36.60, 36.46, 36.41, 36.29, 36.20, 35.59, 35.432, 35.41, 35.28, 34.10, 34.01, 33.44, 32.86, 32.56, 31.72, 31.64, 28.99, 28.89, 28.27, 27.96, 27.32, 23.80, 23.11, 23.09, 22.99, 17.59, 17.54, 17.44, 12.86, 12.80. MALDI-TOFMS (m/z): [M+Na] calcd for C$_{97}$H$_{158}$N$_6$NaO$_{13}$, 1639.31; found, 1640.28.

Compound 25. Compound 25 was prepared by the reduction of 24 (Procedure B), and was purified by column chromatography over silica gel using ethyl acetate and MeOH/Et$_3$N (50:1) as the eluents (80% yield). $^1$H NMR (300 MHz, CDCl$_3$/CD$_3$OD=1:1, δ): 3.97 (m, 4H), 3.82 (m, 4H), 3.67 (s, CO$_2$CH$_3$, 3H), 3.51 (br, 3H), 3.22 (br, 1H). 2.23-0.89 (m, 120H), 0.75 (m, 12H). $^{13}$C NMR (300 MHz, CDCl$_3$/CD$_3$OD=1:1, δ): 176.26, 175.36, 175.33, 78.75, 73.61, 68.68, 68.52, 52.24, 51.95, 50.44, 50.01, 47.68, 47.60, 47.52, 47.18, 47.13, 47.10, 46.58, 42.94, 42.86, 42.58, 42.52, 40.32, 40.31, 36.92, 36.66, 36.27, 35.48, 35.34, 34.09, 33.91, 32.94, 32.85, 31.78, 31.69, 29.05, 28.33, 28.02, 27.37, 23.85, 23.12, 23.05, 17.57, 17.46, 12.80, 10.90. MALDI-TOF mass (m/z): [M+Na]$^+$, calcd for C$_{97}$H$_{160}$N$_4$O$_{13}$Na 1613.33, found: 1609.28.

Compound 26. Compound 26 was obtained by coupling between hydrolyzed 24 and amine 20 (Procedures A and C). The product was purified by repeated precipitation in CH$_3$CN (86% yield). $^1$H NMR (300 MHz, CDCl$_3$/CD$_3$OD=1:1, δ): 3.98 (m, 6H), 3.82 (m, 6H), 3.68 (s, CO$_2$CH$_3$, 3H), 3.52 (br, 5H), 3.26 (br, 1H), 2.39-0.85 (m, 180H), 0.85 (m, 18H). $^{13}$C NMR (300 MHz, CDCl$_3$/CD$_3$OD=1:1, δ): 176.31, 175.36, 175.27, 78.69, 73.71, 73.35, 68.79, 68.63, 62.38, 52.11, 50.43, 50.40, 47.72, 47.68, 47.27, 47.22, 47.19, 47.15, 42.87, 42.59, 42.48, 40.33, 40.29, 36.94, 36.69, 36.50, 36.36, 36.27, 35.54, 35.51, 35.36, 34.21, 33.53, 32.92, 32.60, 31.80, 29.04, 28.36, 28.23, 28.07, 27.40, 27.36, 23.92, 23.23, 23.16, 18.33, 17.77, 17.72, 17.62, 13.02, 12.97. MALDI-TOF mass (m/z): [M+H]$^+$, calcd for C$_{145}$H$_{237}$N$_8$O$_{19}$ 2396.47, found: 2391.15. [M+Na]$^+$, calcd for C$_{145}$H$_{236}$N$_8$O$_{19}$Na 2418.47, found: 2419.28.

Compound 27. Compound 27 was prepared by the reduction of 26 (Procedure B), and was purified by column chromatography using EtOAc and MeOH/Et$_3$N (50:1) as the eluents (75% yield). $^1$H NMR (300 MHz, CDCl$_3$/CD$_3$OD=1:1, δ): 3.98 (m, 6H), 3.83 (m, 6H), 3.67 (s, CO$_2$CH$_3$, 3H), 3.53 (br, 5H), 2.90 (br, 1H). 2.40-0.85 (m, 180H), 0.72 (m, 18H). $^{13}$C NMR (300 MHz, CDCl$_3$/CD$_3$OD=1:1, δ): 178.88, 175.03, 174.02, 173.06, 77.49, 72.42, 72.21, 67.49, 62.38, 54.37, 50.79, 48.37, 45.90, 45.68, 41.66, 41.31, 39.05, 35.69, 35.42, 35.25, 35.02 34.26, 34.24, 34.17, 34.12, 33.78, 32.96, 31.67, 30.49, 27.77, 27.11, 26.79, 26.11, 23.01, 22.65, 21.94, 21.73, 21.42, 16.41, 16.30, 11.72. MALDI-TOF mass (m/z): [M+Na]$^+$, calcd for C$_{145}$H$_{239}$N$_6$O$_{19}$Na 2392.37, found: 2391.14.

Compound 1. Compound 17 (0.505 g, 1.2 mmol) and NBD Chloride (4-Chloro-7-Nitrobenzofurazan, 0.36 g, 1.8 mmol) were dissolved in MeOH (10 mL). Sodium bicarbonate (0.152 g, 1.8 mmol) was added to the solution. The reaction mixture was stirred at room temperature for 24 h. Solvent was removed in vacuo. The residue was diluted with water (30 mL) and extracted with ethyl acetate (2×50 mL). The combined organic phase was washed with water, dried over MgSO$_4$, filtered, concentrated in vacuo, and purified by column chromatography over silica gel using EtOAc/hexane (1:2) as the eluents to give an orange solid (0.524 g, 75% yield). mp 143-145° C. $^1$H NMR (300 MHz, CDCl$_3$/CD$_3$OD=1:1, δ): 8.44 (d, J=8.4 Hz, 1H), 6.26 (d, J=8.4 Hz, 1H), 3.96 (s, 1H), 3.81 (s, 1H), 3.64 (s, CO$_2$CH$_3$, 3H), 3.56 (br, 1H), 2.48-1.12 (m, 24H), 0.98 (m, 6H), 0.69 (s, 3H). $^{13}$C NMR (300 MHz, CDCl$_3$/CD$_3$OD=1:1, δ): 176.21, 145.82, 139.53, 121.83, 99.46, 73.44, 68.42, 51.92, 47.55, 47.06, 42.77, 42.46, 40.31, 36.30, 36.18, 35.55, 35.13, 31.69, 31.63, 28.99, 28.23, 27.40, 23.03, 17.43, 12.87. ESI-MS (m/z): [M+H]$^+$ calcd for C$_{31}$H$_{45}$N$_4$O$_7$, 585.3; found, 555.0.

Compound 2. Compound 2 was obtained by coupling between hydrolyzed 1 and amine 20 (Procedures A and C). The product was purified by column chromatography over silica gel using EtOAc/MeOH (20:1) as the eluents to afford an orange solid (78%). $^1$H NMR (300 MHz, CDCl$_3$/CD$_3$OD=1:1, δ): 8.50 (d, J=8.7 Hz, 1H), 6.23 (d, J=8.4 Hz, 1H), 3.98 (m, 3H), 3.83 (m, 3H), 3.68 (s, CO$_2$CH$_3$, 3H), 3.55 (br, 3H), 2.41-0.92 (m, 90H), 0.71 (m, 9H). $^{13}$C NMR (300 MHz, CDCl$_3$/CD$_3$OD=1:1, δ): 175.38, 145.82, 139.53, 121.83, 99.46, 72.96, 72.87, 72.68, 68.09, 67.86, 51.42, 46.36, 46.29, 41.76, 41.68, 41.64, 39.39, 39.25, 36.14, 35.75, 35.53, 34.86, 34.65, 34.59, 31.86, 31.07, 30.88, 29.57, 27.98, 27.44, 27.18, 26.49, 26.40, 23.08, 22.46, 17.02, 16.97, 12.30. MALDI-TOF (m/z): [M+Na]$^+$, calcd for C$_{83}$H$_{130}$N$_6$O$_{12}$Na 1386.85, found: 1386.09; [M+K], calcd for C$_{83}$H$_{130}$N$_6$O$_{12}$K 1402.95, found: 1402.32.

Compound 3. Compound 3 was obtained by coupling between hydrolyzed 1 and amine 25 (Procedures A and C). The product was purified by column chromatography over silica gel using EtOAc/MeOH (15:1) as the eluents to afford an orange solid (42%). $^1$H NMR (300 MHz, CDCl$_3$/CD$_3$OD=1:1, δ): 8.51 (d, J=8.1 Hz, 1H), 7.47 (br, 2H), 6.28 (d, J=8.7 Hz, 1H), 3.98 (m, 5H), 3.83 (m, 5H), 3.68 (s, CO$_2$CH$_3$, 3H), 3.54 (br, 5H), 2.76-0.97 (m, 150H), 0.80 (m, 15H). $^{13}$C NMR (300 MHz, CDCl$_3$/CD$_3$OD=1:1, δ): 175.21, 174.08, 174.05, 145.82, 139.56, 121.79, 99.48, 72.61, 72.39, 67.72, 51.03, 46.62, 46.53, 46.06, 46.01, 41.64, 41.41, 39.20, 39.08, 35.85, 35.54, 35.52, 35.33, 35.11, 34.58, 34.39, 34.36, 34.20, 33.11, 31.69; 30.72, 27.84, 27.23, 26.93, 26.18, 22.79, 22.12, 16.63, 16.54, 11.93. MALDI-TOF (m/z): [M+H]$^+$, calcd for C$_{127}$H$_{201}$N$_8$O$_{19}$ 2143.99, found: 2147.27; [M+Na]$^+$, calcd for C$_{127}$H$_{200}$N$_8$O$_{19}$Na 2165.99, found: 2163.45.

Compound 4. Compound 4 was obtained by coupling between hydrolyzed 1 and amine 27 (Procedures A and C). The product was purified by column chromatography over silica gel using EtOAc/MeOH (10:1) as the eluents to afford an orange solid (70%). $^1$H NMR (300 MHz, CDCl$_3$/CD$_3$OD=1:1, δ): 8.50 (d, J=8.5 Hz, 1H), 7.49 (br, 5H), 6.30 (d, J=8.4 Hz, 1H), 4.08 (br, 1H), 3.98 (m, 7H), 3.83 (m, 7H), 3.68 (s, CO$_2$CH$_3$, 3H), 3.54 (br, 6H), 2.54-0.98 (m, 210H), 0.82 (m, 21H). $^{13}$C NMR (300 MHz, CDCl$_3$/CD$_3$OD=1:1, δ): 175.29, 175.05, 174.01, 173.911 145.88, 139.60, 121.84, 99.47, 72.46, 72.33, 67.57, 54.38, 50.95, 46.48, 45.94, 45.90, 41.59, 41.30, 39.00, 35.73, 35.45, 35.25, 34.30, 33.01, 31.64, 30.60, 27.75, 27.16, 26.84, 26.09, 22.71, 22.04, 16.54, 16.42, 11.82. MALDI-TOF mass (m/z): [M+H]$^+$, calcd for $C_{175}H_{279}N_{10}O_{25}$ 2923.13, found: 2922.21.

Compound 11. 4-Amino TMPO (0.684 g, 4.0 mmol) and glycidol (1.50 g, 20 mmol) were dissolved in anhydrous THF (4 mL). The reaction mixture was heated to reflux under $N_2$ for 24 h. The crude product was purified by column chromatography over silica gel using $CHCl_3/MeOH=10:1$ (Rf=0.48) as the eluents to obtain 0.67 g viscous oil. The oil was dissolved in Millipore water (5 mL) and was lyophilized to give a red oil (0.45 g, 46%). UV (THF) $\lambda_{max}$, nm ($\epsilon$): 276 (350). ESI mass (m/z): [M+H]$^+$, calcd for $C_{15}H_{32}N_2O_{15}$, 320.42, found 320.0.

Compound 9. Compound 16 (0.866 g, 2.0 mmol, prepared by Procedure A) was combined with $HCO_2H$ (8 mL) and a catalytic amount of $HClO_4$ (1 drop). The mixture was heated to 60° C. for 2 h. The mixture was poured into water (20 mL) and was extracted with ethyl acetate (2×50 mL). The combined organic phase was washed with water, dried over $MgSO_4$, filtered, concentrated, and purified by column chromatography over silica gel using EtOAc/Hexane (1:2) to give the diformate derivative (0.62 g, 72% yield). The diformate (0.39 g, 0.8 mmol), oxalyl chloride (0.16 g, 1.2 mmol), and anhydrous DMF (1 drop) were dissolved in anhydrous $CH_2Cl_2$ (10 mL). The mixture was stirred at room temperature for 30 min. The solvent and excess oxalyl chloride were removed by rotary evaporation. The residue was dissolved in anhydrous $CH_2Cl_2$ (5 mL), to which a solution of 1-aminonaphthalene (0.115 g, 0.8 mmol) and triethylamine (0.1 mmol) in $CH_2Cl_2$ (3 mL) was added via a syringe under $N_2$ at 0° C. After 2 h at room temperature, the solvent was removed by rotary evaporation. The residue was combined with $K_2CO_3$ (0.33 g) in MeOH (5 mL) and the mixture was heated to reflux 3 h. The reaction mixture was extracted with ethyl acetate (2×50 mL). The combined organic phase was washed with water, dried over $MgSO_4$, filtered, concentrated in vacuo, and was purified by column chromatography over silica gel using EtOAc/Hexane (1:1) as the eluents (0.32 g, 71%). mp 152-155° C. $^1$H NMR (300 MHz, $CDCl_3/CD_3OD=1:1$, $\delta$): 8.15 (br, NH, 1H), 7.86-7.41 (m, ArH, 7H), 4.03 (s, 1H), 3.84 (s, 1H), 3.13 (s, br, 1H), 2.52-1.03 (series of m, 29H), 0.98 (s, 3H), 0.89 (s, 3H). $^{13}$C NMR (75 MHz, $CDCl_3/CD_3OD=1:1$, $\delta$): 173.98, 134.25, 132.81, 128.62, 128.03, 126.21, 126.02, 125.69, 121.98, 121.74, 73.51, 68.54, 61.33, 54.85, 46.64, 46.40, 42.10, 41.96, 39.82, 35.66, 35.29, 34.92, 33.21, 31.35, 27.98, 26.98, 26.43, 23.60, 22.48, 17.55, 12.51. ESI-MS (m/z): [M+H]$^+$ calcd for $C_{34}H_{47}N_4O_3$, 559.75; found, 559.0.

Compound 28. Compound 28 was prepared by the reduction of 9 (Procedure B), and was purified by column chromatography over silica gel using ethyl acetate and MeOH/Et$_3$N (50:1) as the eluents and precipitation into $CH_3CN$ (86% yield). mp 197-200° C. $^1$H NMR (300 MHz, $CDCl_3/CD_3OD=10:1$, $\delta$): 7.92-7.63 (m, ArH, 4H), 7.58-7.39 (m, ArH, 3H); 3.96 (s, 1H), 3.81 (s, 1H), 2.64-2.38 (m, 3H), 2.19-0.98 (series of m, 25H), 0.90 (s, 3H), 0.69 (s, 3H). $^{13}$C NMR (75 MHz, $CDCl_3/CD_3OD=10:1$, $\delta$): 173.87, 134.25, 132.86, 132.75, 128.59, 128.02, 126.19, 126.02, 125.72, 121.93, 121.63, 73.15, 68.32, 51.26, 49.99, 49.71, 49.43, 49.14, 46.46, 41.74, 41.68, 39.45, 35.66, 35.40, 34.85, 34.55, 31.83, 28.07, 27.65, 26.38, 23.35, 22.59, 17.47, 12.54. ESI-MS (m/z): [M+H]$^+$ calcd for $C_{34}H_{49}N_2O_3$, 533.76; found, 532.0.

Compound 29. Compound 29 was obtained by coupling between hydrolyzed 21 and amine 28 (Procedures A and C). The product was purified by column chromatography over silica gel using $CHCl_3/MeOH$ (15:1) as the eluents (46% yield). $^1$H NMR (300 MHz, DMSO-d6, $\delta$): 9.91 (s, NH, 1H), 8.22-7.47 (m, 7 ArH, 3 NH, 10H), 4.10 (m, 4H), 3.69 (m, 4H), 3.62 (m, 4H), 2.50-0.83 (series of m, 120H), 0.62 (m, 12H). $^{13}$C NMR (75 MHz, DMSO-d6, $\delta$): 172.41, 171.62, 133.76, 133.71, 128.10, 127.82, 125.92, 125.65, 125.54, 122.74, 121.68, 71.00, 66.22, 66.12, 60.81, 48.89, 46.17, 45.80, 45.74, 42.16, 41.52, 41.38, 36.33, 36.02, 35.22, 34.98, 34.83, 34.42, 34.30, 33.24, 32.71, 31.94, 28.65, 28.45, 27.56, 26.30, 26.13, 22.77, 17.13, 12.36. MALDI-TOFMS (m/z): [M+Na]$^+$ calcd for $C_{106}H_{163}N_7NaO_{12}$, 1750.46; found, 1753.88.

Compound 30. Compound 30 was prepared by the reduction of 29 (Procedure B), and was purified by column chromatography over silica gel using $CHCl_3/MeOH$ (15:1) as the eluents (73% yield). $^1$H NMR (300 MHz, DMSO-d6, $\delta$): 7.95-7.42 (m, 10H), 4.07-3.95 (m, 4H), 3.82 (m, 4H), 3.57 (br, 3H), 3.22 (br, 1H), 2.37-0.83 (series of m, 120H), 0.79-0.65 (m, 12H). $^{13}$C NMR (75 MHz, DMSO-d6, $\delta$): 173.66, 172.58, 171.61, 133.73, 133.24, 128.11, 127.82, 125.92, 125.65, 125.54, 122.74, 121.68, 71.00, 66.22, 66.12, 60.81, 48.89, 46.17, 45.80, 45.74, 42.16, 41.52, 41.38, 36.33, 36.02, 35.22, 34.98, 34.83, 34.42, 34.30, 33.24, 32.71, 31.94, 28.65, 28.45, 27.56, 26.30, 26.13, 22.78, 17.25, 12.48. MALDI-TOFMS (m/z): [M+Na]$^+$ calcd for $C_{106}H_{165}N_5NaO_{12}$, 1724.46; found, 1724.71.

Compound 31. Compound 31 was obtained by coupling between hydrolyzed 24 and amine 28 (Procedures A and C). The product was purified by column chromatography over silica gel using $CHCl_3/MeOH$ (15:1) as the eluents (59% yield). $^1$H NMR (300 MHz, $CDCl_3/CD_3OD=1:1$, $\delta$): 7.95 (d, 1H), 7.86 (d, 2H), 7.72 (d, 2H), 7.54 (m, 2H), 7.47 (m, 5H), 4.01-3.90 (m, 5H), 3.82 (m, 5H), 3.55 (br, 4H), 3.24 (br, 1H), 2.42-0.98 (series of m, 135H), 0.96 (m, 15H), 0.78 (m, 15H). $^{13}$C NMR (300 MHz, $CDCl_3/CD_3OD=1:1$, $\delta$): 175.43, 175.08, 174.99, 174.90, 134.82, 133.36, 129.30, 128.78, 126.92, 126.58, 126.47, 125.90, 123.37, 122.68, 73.41, 68.50, 68.33, 62.07, 50.06, 47.46, 46.97, 46.93, 46.88, 42.52, 42.27, 42.16, 39.98, 39.93, 39.86, 36.66, 36.53, 36.38, 36.27, 36.22, 36.18, 36.04, 35.99, 35.95, 35.86, 35.41, 35.22, 35.19, 35.03, 34.94, 34.00, 33.24, 32.59, 32.26, 30.13, 28.70, 28.06, 27.76, 27.07, 27.02, 23.63, 22.96, 22.89, 22.80, 17.51, 17.46, 12.82, 12.75, 12.70. MALDI-TOFMS (m/z): [M+Na]$^+$ calcd for $C_{130}H_{202}N_8NaO_{15}$, 2140.03; found, 2139.83.

Compound 32. Compound 32 was prepared by the reduction of 31 (Procedure B), and was purified by column chromatography over silica gel using ethyl acetate and MeOH/Et$_3$N (20:1) as the eluents (61% yield). $^1$H NMR (300 MHz, $CDCl_3/CD_3OD=1:1$, $\delta$): 7.95 (d, 1H), 7.86 (d, 1H), 7.72 (d, 1H), 7.58 (m, 1H), 7.49 (m, 3H), 4.05-3.92 (m, 5H), 3.82 (m, 5H), 3.55 (br, 4H), 2.66 (br, 1H), 2.28-1.02 (series of m, 135H), 0.98-0.89 (m, 15H), 0.78-0.62 (m, 15H). $^{13}$C NMR (300 MHz, $CDCl_3/CD_3OD=1:1$, $\delta$): 175.09, 174.55, 134.47, 133.01, 128.95, 128.43, 126.56, 126.23, 126.12, 125.55, 123.02, 122.33, 73.05, 68.16, 60.77, 51.51, 49.69, 47.08, 46.90, 46.53, 42.17, 41.91, 39.58, 37.56, 36.32, 36.03, 35.83, 34.87, 34.73, 33.62, 33.60, 33.38, 32.24, 28.32, 27.72, 27.42, 26.67, 23.30, 22.62, 22.52, 17.17, 13.92, 12.40. MALDI-TOFMS (m/z): [M+Na]$^+$ calcd for $C_{130}H_{204}N_6NaO_{15}$, 2114.03; found 2113.27.

Compound 8. A solution of compound 17 (0.421 g, 1.0 mmol), Dansyl chloride (0.27 g, 1.0 mmol) and triethyl anime (TEA, 0.21 mL, 2 mmol) in $CH_2Cl_2$ (8 mL) was stirred at room temperature under $N_2$ for 3 h. Solvent was removed by rotary evaporation. The product was purified by column chromatography over silica gel using EtOAc/hexane (2:1) as the eluents (0.63 g, 91%). mp 150-152° C. $^1$H NMR (300 MHz, CDCl$_3$, $\delta$): 8.50 (d, J=8.4 Hz, ArH, 1H), 8.26 (t, J=9.3 Hz, 7.5 Hz, ArH, 2H), 7.51 (m, ArH, 2H), 7.15 (d, J=7.5 Hz, ArH, 1H), 5.36 (d, J=7.8 Hz, NH, 1H), 3.92 (s, 1H), 3.78 (s, 1H), 3.65 (s, (CO$_2$CH$_3$, 3H), 2.96 (br, 1H), 2.40-1.01 (series of m, 26H), 0.94 (d, 3H), 0.77 (s, 3H), 0.63 (s, 3H). $^{13}$C NMR (75 MHz, CDCl$_3$, δ): 175.03, 151.93, 136.29, 130.24, 130.03, 129.85, 129.27, 128.31, 123.33, 119.42, 115.30, 73.10, 68.44, 54.89, 54.21, 51.72, 47.22, 46.58, 45.64, 42.15, 42.05, 39.51, 37.81, 35.99, 35.37, 34.62, 31.21, 31.04, 28.94, 28.33, 27.62, 26.67, 23.29, 22.68, 17.49, 12.64. ESI-MS (m/z): [M+H]$^+$ calcd for C$_{37}$H$_{55}$N$_2$O$_6$S, 655.90; found, 654.0.

Compound 5. Compound 5 was obtained by coupling between hydrolyzed 8 and amine 30 (Procedures A and C). The product was purified by preparative TLC using CHCl$_3$/MeOH (15:1) as the developing solvents (32% yield). $^1$H NMR (300 MHz, CDCl$_3$/CD$_3$OD=1:1, δ): 8.50 (d, J=9.0 Hz, 1H), 8.29 (d, J=8.7 Hz, 1H), 8.19 (d, J=7.2 Hz, 1H), 7.95 (m, 1H), 7.93 (m, 1H), 7.72 (d, J=8.4 Hz, 1H), 7.58-7.44 (m, 6H), 7.19 (d, J=7.8 Hz, 1H), 4.35 (s, 1H), 4.14-3.98 (m, 5H), 3.82-3.53 (m, 5H), 3.43 (br, 4H), 2.89 (s, N(CH$_3$)$_2$, 6H), 2.72-2.56 (br, 1H), 2.28-0.96 (series of m, 150H), 0.76 (m, 15H). $^{13}$C NMR (300 MHz, CDCl$_3$/CD$_3$OD=1:1, δ): 175.30, 174.97, 136.88, 134.67, 133.17, 131.05, 130.22, 130.06, 129.85, 129.47, 129.33, 129.14, 128.59, 128.47, 128.39, 128.15, 126.40, 126.29, 125.70, 123.24, 119.76, 115.48, 73.25, 68.33, 60.92, 49.90, 48.12, 47.84, 47.23, 46.70, 45.44, 42.38, 42.08, 39.798, 36.51, 36.20, 35.99, 35.09, 34.83, 33.69, 32.43, 28.52, 27.89, 27.58, 26.86, 24.68, 23.47, 22.75, 22.56, 20.77, 17.25, 14.03, 12.33. MALDI-TOFMS (m/z): [M+Na]$^+$ calcd for C$_{142}$H$_{215}$N$_7$NaO$_{17}$S, 2347.32; found, 2347.49.

Compound 6. Compound 6 was obtained by coupling between hydrolyzed 8 and amine 32 (Procedures A and C). The product was purified by preparative TLC using CHCl$_3$/MeOH (15:1) as the developing solvents (64% yield). $^1$H NMR (300 MHz, CDCl$_3$/CD$_3$OD=1:1, δ): 8.50 (d, J=8.1 Hz, 1H), 8.30 (d, J=8.7 Hz, 1H), 8.19 (d, J=7.2 Hz, 1H), 7.95 (m, 1H), 7.85-7.82 (m, 1H), 7.71 (d, J=7.8 Hz, 1H), 7.59-7.42 (m, 6H), 7.18 (d, J=7.5 Hz, 1H), 4.01-3.86 (m, 6H), 3.82-3.71 (m, 6H), 3.49 (br, 5H), 2.89 (s, N(CH$_3$)$_2$, 6H), 2.61-2.44 (br, 1H), 2.22-0.76 (m, 180H), 0.67 (m, 18H). $^{13}$C NMR (300 MHz, CDCl$_3$/CD$_3$OD=1:1, δ): 175.57, 175.05, 152.32, 137.21, 134.93, 133.47, 130.48, 130.30, 129.43, 129.38, 128.85, 128.41, 127.02, 126.65, 126.55, 123.76, 123.48, 122.81, 20.04, 115.72, 73.47, 68.53, 68.42, 54.69, 50.20, 49.62, 49.34, 49.06, 48.78, 48.49, 47.62, 47.51, 47.37, 47.02, 46.99, 46.90, 45.69, 42.91, 42.86, 42.67, 42.35, 40.06, 39.98, 36.75, 36.48, 36.32, 36.28, 35.31, 35.17, 35.09, 34.15, 33.99, 32.71, 28.81, 28.06, 27.87, 27.14, 27.01, 23.72, 23.08, 22.83, 17.58, 17.56, 12.87, 12.80, 12.75. MALDI-TOFMS (m/z): [M+Na]$^+$ calcd for C$_{166}$H$_{254}$N$_8$NaO$_{20}$S, 2736.89; found, 2735.32.

Compound 33. Compound 33 was obtained by coupling between hydrolyzed 8 and amine 23 (Procedures A and C). The product was purified by preparative TLC using CHCl$_3$/MeOH (15:1) as the developing solvents (71% yield). $^1$H NMR (400 MHz, CDCl$_3$/CD$_3$OD=1:1, δ): 8.54 (d, J=6.3 Hz, 1H), 8.32 (d, J=6.3 Hz, 1H), 8.23 (d, J=5.4 Hz, 1H), 7.59-7.53 (m, 3H), 7.22 (d, J=5.7 Hz, 1H), 4.09-3.91 (m, 6H), 3.88-3.75 (m, 6H), 3.68 (s, 3H), 3.55 (br, 5H), 3.02 (br, 1H), 2.90 (s, N(CH$_3$)$_2$, 6H), 2.48-0.82 (m, 180H), 0.79-0.65 (m, 18H). $^{13}$C NMR (100 MHz, CDCl$_3$/CD$_3$OD=1:1, δ): 175.11, 174.00, 151.33, 136.15, 129.52, 129.50, 129.31, 128.41, 127.44, 122.78, 119.02, 114.75, 72.54, 72.48, 67.65, 67.50, 53.71, 50.97, 49.20, 49.18, 46.57, 46.42, 46.02, 45.97, 44.77, 41.85, 41.67, 41.28, 39.07, 38.99, 37.04, 35.81, 35.50, 35.31, 35.08, 34.36, 34.19, 34.14, 34.03, 33.09, 32.92, 31.70, 30.66, 27.81, 27.68, 27.18, 26.89, 26.17, 26.03, 22.77, 22.07, 21.89, 16.59, 11.88, 11.81. MALDI-TOFMS (m/z): [M+Na]$^+$ calcd for C$_{156}$H$_{247}$N$_7$NaO$_{21}$S, 2611.72; found, 2613.68.

Compound 7. Compound 7 was obtained by coupling between hydrolyzed 33 and amine 28 (Procedures A and C). The product was purified by preparative TLC using CHCl$_3$/MeOH (12:1) as the developing solvents (75% yield). $^1$H NMR (300 MHz, CDCl$_3$/CD$_3$OD=1:1, δ): 8.49 (d, J=8.4 Hz, 1H), 8.28 (d, J=8.4 Hz, 1H), 8.19 (d, J=6.6 Hz, 1H), 7.94-7.70 (m, 3H), 7.52-7.19 (m, 6H), 7.18 (d, J=7.2 Hz, 1H), 4.26 (s, 1H), 3.93-3.86 (m, 6H), 3.78-3.72 (m, 7H), 3.50 (br, 5H), 2.86 (s, N(CH$_3$)$_2$, 6H), 2.62-2.35 (br, 2H), 2.32-0.72 (m, 210H), 0.65 (m, 21H). $^{13}$C NMR (300 MHz, CDCl$_3$/CD$_3$OD=1:1, δ): 174.54, 174.03, 173.99, 151.34, 136.15, 133.94, 132.05, 129.50, 129.33, 128.44, 127.91, 127.46, 126.05, 125.70, 125.59, 125.02, 122.80, 122.47, 121.79, 119.04, 114.76, 77.42, 67.52, 67.50, 54.19, 49.67, 49.23, 48.95, 48.62, 48.35, 47.07, 46.90, 46.51, 46.44, 45.29, 41.82, 41.64, 41.37, 41.26, 39.05, 39.02, 35.81, 35.50, 35.29, 34.34, 34.19, 34.13, 33.08, 31.69, 29.22, 27.79, 27.18, 26.89, 26.14, 26.01, 22.77, 22.08, 21.89, 16.60, 11.89, 11.85. MALDI-TOFMS (m/z): [M+Na] calcd for C$_{190}$H$_{293}$N$_9$NaO$_{23}$S, 3126.47; found, 3120.75.

UV and Fluorescence Measurements of the NBD-Labeled Cholate Oligomers 1-4: Stock solutions (1.0×10$^{-3}$ M) of 1-4 in anhydrous THF were prepared. An aliquot (20.0 μL for the UV measurements and 4.0 μL for the fluorescence measurements) of the stock solution was diluted by (a) 2.00 mL of carbon tetrachloride with 2 volume % DMSO, or (b) 2.00 mL of ethyl acetate/hexane (v/v=1.05/2) with 2 volume % DMSO in a quartz cuvet. Aliquots of DMSO (10.0 μL) were added to the sample with a Hamilton Gastight syringe. After each addition, the sample was vortexed for 1 minute before the UV or fluorescence spectrum was recorded. Fluorescence spectrum was recorded with the excitation wavelength set at 336 nm.

Fluorescence Quenching of the NBD-Labeled Cholate Oligomers 1-4: Typical procedures for the quenching experiment are as follows. Stock solutions (1.0×10$^{-3}$ M) of 1-4 in anhydrous THF were prepared. An aliquot (25.0 μL) of the stock solution was diluted by 2.00 mL of carbon tetrachloride with 5 vol. % DMSO in a quartz cuvet. Aliquots (5.0 μL, 0.8 M) of the quencher (11 or 12) in THF were added with a Hamilton Gastight syringe. After each addition, the sample was vortexed for 1 minute before the fluorescence spectrum was recorded. The excitation wavelength was set at 336 nm and the maximum emission intensity at 527 nm was monitored.

FRET Study of the Donor-Acceptor Labeled Cholate Oligomers 5-9 Stock solutions (2.0×10$^{-4}$M) of 5-9 in anhydrous THF were prepared. An aliquot (20.0 μL) of the stock solution was diluted by (a) 2.00 mL of ethyl acetate/hexane (v/v=1.05/2) with 1 vol. % DMSO and (b) (a) 2.00 mL of ethyl acetate/hexane (v/v=1/1) with 1 vol. % DMSO in a quartz cuvet. Ten aliquots of DMSO (10.0 μL each) were added to the sample. After each addition, the sample was vortexed for 1 minute before the fluorescence spectrum was recorded. The excitation wavelength was set at 287 nm.

Example 2

Oligomeric Cholates

Amphiphilic Foldamers with Nanometer-Sized Hydrophilic Cavities

This Example shows that cholate oligomers fold into helical structures with nanometer-sized hydrophilic internal cavities in solvent mixtures consisting mostly of nonpolar solvents such as carbon tetrachloride or ethyl acetate/hexane and 2-5% of a polar solvent such as methanol or DMSO. The conformations of the foldamers were studied by UV, fluorescence, fluorescence quenching, and fluorescence resonance energy transfer. The nature of the polar/nonpolar solvents and their miscibility strongly influenced the folding reaction. Folding was cooperative, as evidenced by the sigmoidal curves in solvent denaturation experiments. The folded conformers became more stable with an increase in the chain length. The folding/unfolding equilibrium was highly sensitive toward the amount of polar solvent. One percent variation in the solvent composition could change the folding free energies by 0.5-1.4 kcal/mol.

Results

Design of Cholate Foldamers. The inventor has previously synthesized amphiphilic baskets by attaching four cholate groups to a calixarene scaffold. Ryu, E.—H.; Zhao, Y. *Org. Lett.* 2004, 6, 3187-3189; Zhao, Y.; Ryu, E.-H. *J. Org. Chem.* 2005, 70, 7585-7591. The molecules adopt micellelike conformations in polar solvents, with the hydroxyl groups facing outward, and reversed-micelle-like conformations in nonpolar solvents, with the hydroxyl groups inward. Similar solvophobically driven conformational changes may also occur if several cholates are linked in a head-to-tail fashion (FIG. 1).

Cholate has a polar (alpha (α)) face and a non-polar (beta (β)) face, as shown below.

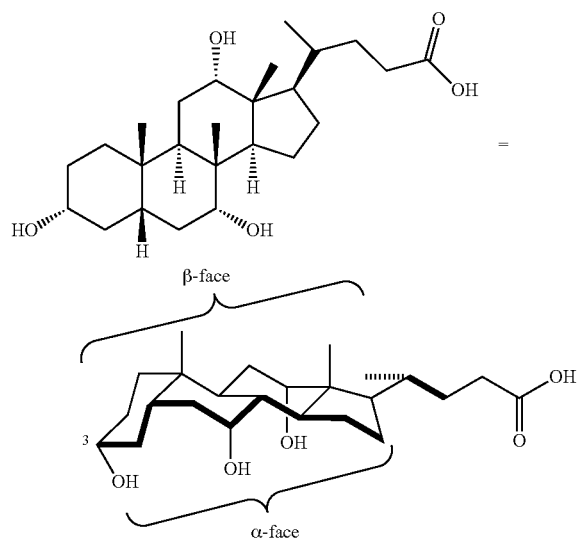

The conformational effects of the solvent on oligomeric cholates are described below. If the solvent mixture has similar preference for the alpha (α) and the beta (β) faces, the oligomer should adopt extended, random conformations to maximize its entropy. In a mostly nonpolar solvent mixture, which preferentially solvates the hydrophobic β faces, the molecule is expected to bury the α faces. Several possible scenarios exist, including aggregation/precipitation. If sufficiently low concentration of nonpolar solvent is used and the possibility of precipitation excluded, the molecule may adopt collapsed but disordered conformations or, as shown in FIG. 1, fold into a helical structure with a hydrophobic exterior and a hydrophilic interior. Choice between the disordered or the helical conformer was not obvious at the outset of the project and probably depends on several factors including the intrinsic curvature and the rigidity of the monomer units.

As demonstrated below, the intrinsic folding propensities of the cholate backbone can be controlled using the present methods and solvent compositions. A folded cholate oligomer resembles a unimolecular reversed micelle with a hydrophobic exterior and a hydrophilic interior. As in the molecular baskets, the most suitable solvents for such conformers consist of mostly a nonpolar solvent such as carbon tetrachloride and a small amount of a polar solvent such as methanol or dimethyl sulfoxide (DMSO). Ryu, E.-H.; Zhao, Y. *Org. Lett.* 2004, 6, 3187-3189; Zhao, Y.; Ryu, E.-H. *J. Org. Chem.* 2005, 70, 7585-7591.

Ternary solvent mixtures (DMSO/ethyl acetate/hexane) were used because folding may be more likely to occur in partially miscible solvent mixtures than completely miscible ones. This is because the folded conformer would enrich the polar solvents in its hydrophilic interior and such demixing should be easier with low solvent miscibility. DMSO is completely miscible with ethyl acetate but immiscible with hexane. By varying the ratio between ethyl acetate and hexane, the solvent miscibility can be modulated. For example, DMSO is miscible at all ratios with ethyl acetate/hexane (1/1) but is miscible only up to 5 vol. % in ethyl acetate/hexane (1/2) in our hands.

Typical Synthesis of Cholate Oligomers. Among the three hydroxyl groups, the most reactive one is the hydroxyl at the C-3 position. Following a procedure reported by Davis and colleagues (Davis, A. P.; Dresen, S.; Lawless, L. J. *Tetrahedron Lett.* 1997, 38, 4305-4308) the β mesylate 15 was prepared from methyl cholate 14 using triphenylphosphine and diisopropyl azodicarboxylate (DIAD). Sodium azide attacks the mesylate by an SN2 reaction to afford azide ester 16, which is reduced by triphenylphosphine in aqueous THF to give compound 17.

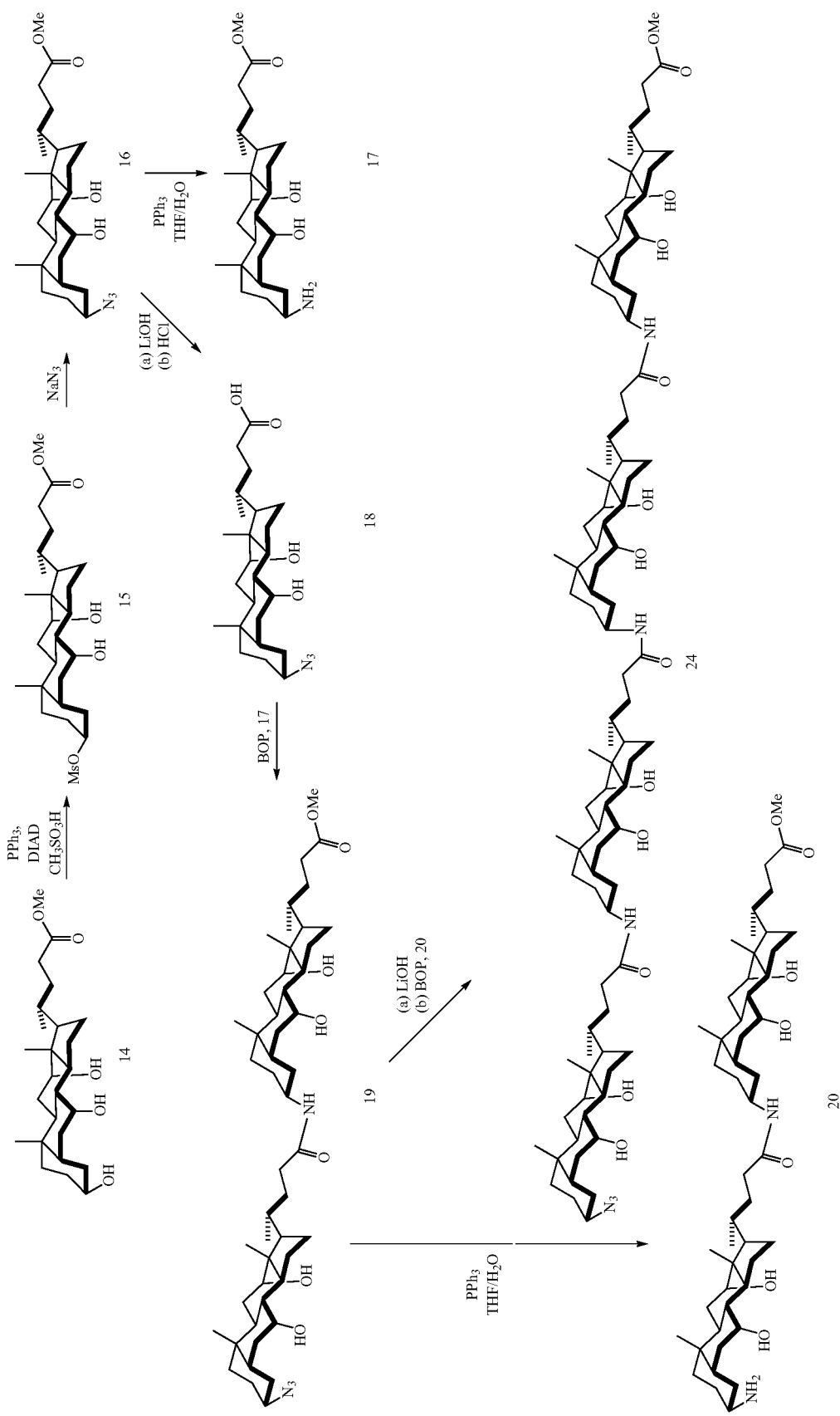

Standard amide coupling between 17 and carboxylic acid 18 using benzotriazol-1-yloxytris(dimethylamino) phosphonium hexafluorophosphate (BOP) yields the dimeric azide ester 19. Repetition of the procedures gives the tetrameric azide ester 24. Other oligomeric cholates could be synthesized in similar fashions, e.g., hydrolysis of 24 and amide coupling between the resulting acid and dimer amine 20 gives the hexamer.

UV and Fluorescence of NBD-Labeled Oligomeric Cholates. A folded cholate oligomer should enrich polar solvent molecules within its internal cavity. Thus, a solvent-sensitive chromophore attached to the oligomer may generate a detectable change in signal as the local solvent composition changes. Cholate monomers, trimers, pentamers, and heptamers (1-4) that were labeled with the N-(7-nitrobenz-2-oxa-1,3-diazo-4-yl) (NBD) group were prepared, whose UV and fluorescence are both sensitive to solvent polarity (Fery-Forgues, S.; Fayet, J.-P.; Lopez, A. *J. Photochem. Photobiol. A* 1993, 70, 229-2463).

uted around the NBD group. Thus, an unsymmetrical solvation shell cannot be modeled by the NBD group on the monomer in homogeneous DMSO/CCl$_4$ mixtures. Even though the exact cause of the unusual UV of the heptamer is unclear at this point, this local environment is clearly destroyed with the addition of just a few percent of DMSO. Such behavior is consistent with the unfolding of the cholate backbone, which will destroy the internal cavity and local enrichment of DMSO.

Figure 3A:
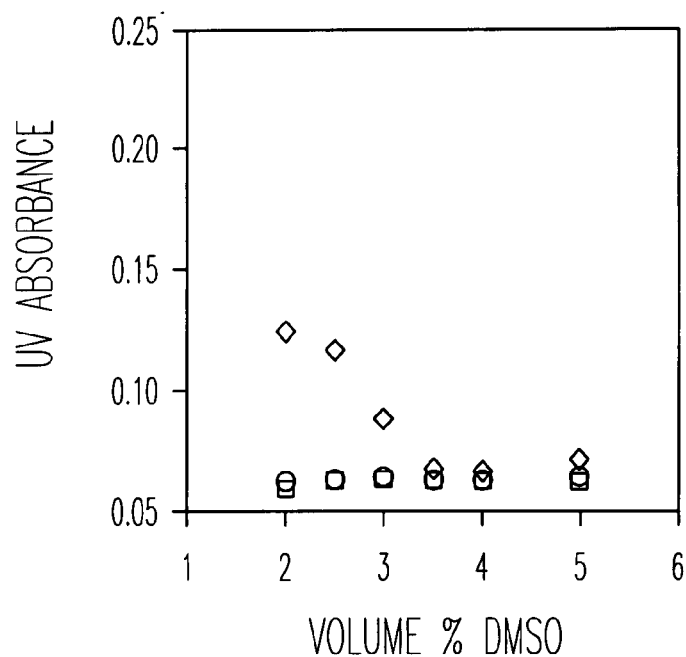
FIGS. 3A and 3B show UV absorbance at 334 nm for monomer 1 (□), trimer 2 (○), pentamer 3 (Δ), and heptamer 4 (◊) as a function of DMSO in (A) CCl$_4$ and (B) ethyl acetate/hexane=1/2. [Oligomer]=10 µM.

The effect of chain length on the UV absorption was then studied. In FIG. 3A, the UV absorbance at 334 nm (which is from the $\pi$-$\pi$* transition and most sensitive toward DMSO percentage) is plotted against DMSO percentage for the various oligomers. A distinctive chain-length dependence is observed, as none of the shorter oligomers (1-3) display solvent-sensitive absorptions. Most significantly, the plot for the heptamer has a sigmoidal shape, a hallmark of cooperative phenomena typically observed in protein denaturation (Fery-Forgues, S.; Fayet, J.-P.; Lopez, A. *J. Photochem. Photobiol.*

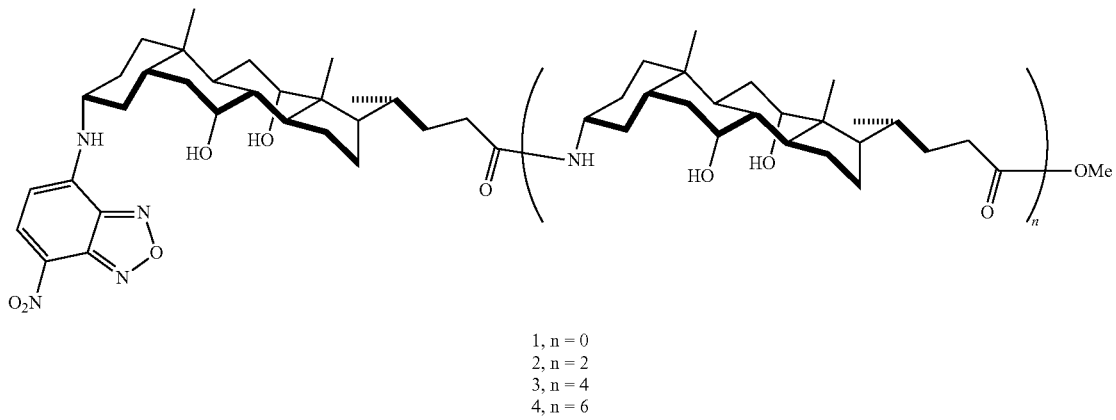

1, n = 0
2, n = 2
3, n = 4
4, n = 6

Figure 2A:
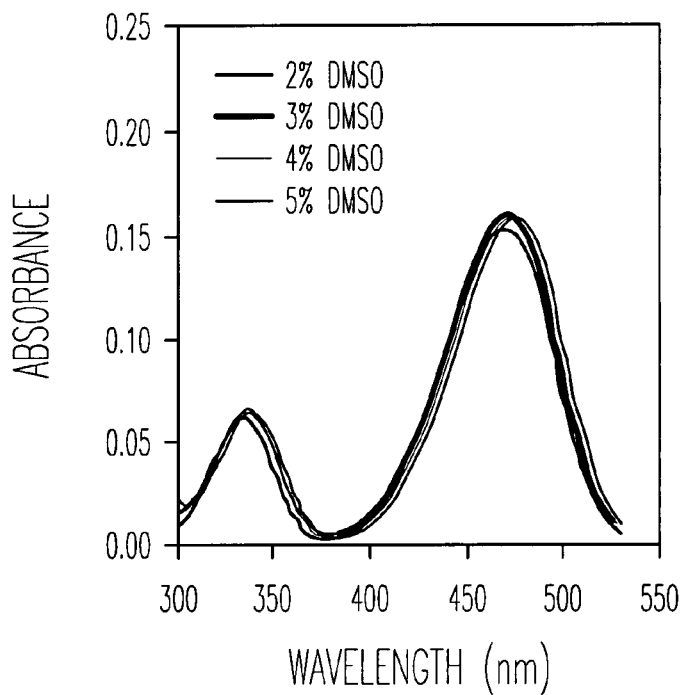
FIGS. 2A and 2B show UV spectra of (A) monomer 1 and (B) heptamer 4 in DMSO/CCl$_4$ mixtures. [1]=[4]=10 µM.
Figure 2B:
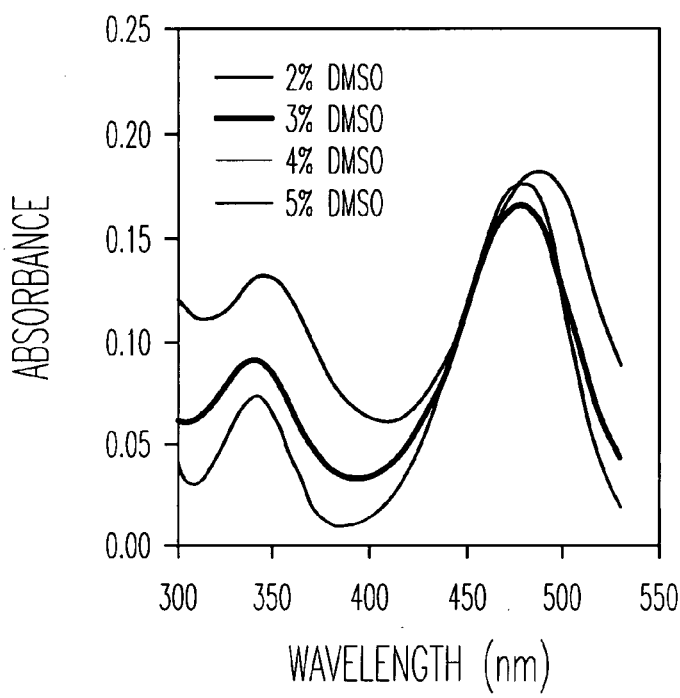

Because short oligomers cannot fold, any folding derived "unusual" solvent effects should only occur in the longer oligomers (3, 4). Shorter oligomers (1, 2), therefore, serve as control compounds. As in the molecular baskets, an increase in the polar solvent is expected to destabilize the reversed-micelle-like conformers. Hence, the unusual solvent effects should diminish with higher percentage of the polar solvent. In the end, all the oligomers should behave similarly if sufficient amount of the polar solvent is added to unfold the longer oligomers. These predictions are indeed confirmed in the NBD-labeled oligomers. When the volume percentage of DMSO is increased from 2 to 5% in CCl$_4$, the UV spectrum of the monomer (FIG. 2A) stays nearly the same, but that of the heptamer displays large changes (FIG. 2B). Moreover, the difference between the two is most significant in low percentage of DMSO and quickly disappears with higher (4-5%) DMSO.

The inventor's folding model predicts a higher local concentration of DMSO for a folded oligomer. Thus, initially it was thought was that the unusual UV absorptions of the heptamer (in 2% DMSO/CCl$_4$) should be modeled simply by the monomer in solvent mixtures with higher DMSO. However, the UV spectrum of the monomer is almost identical in 10/90, 50/50, and 90/10 mixtures of DMSO and CCl$_4$. Apparently, it is not simply an increase in solvent polarity that caused the unusual UV of the heptamer. This result is not a total surprise because, even if DMSO is enriched inside the folded heptamer, the solvent molecules are not evenly distrib-

*A* 1993, 70, 229-2463). The data support a helix-coil transition, which is cooperative and indicative of higher stability with an increase in the chain length. Schellman, J. A. *J. Phys. Chem.* 1958, 62, 1485-1494; Zimm & Bragg, *J. Chem. Phys.* 1959, 31, 526-535; and Lifson & Roig, *J. Chem. Phys.* 1961, 34, 1963-1974; Poland, D. C.; Scheraga, H. A. *Theory of the Helix-Coil Transition*; Academic Press: New York, 1970.

At this point, the higher-absorbing state of the heptamer was tentatively assigned as the folded state and the monomer-like, lower-absorbing state as the unfolded state. As will be shown in later sections, the helix-coil model is completely consistent with the data.

Figure 3B:
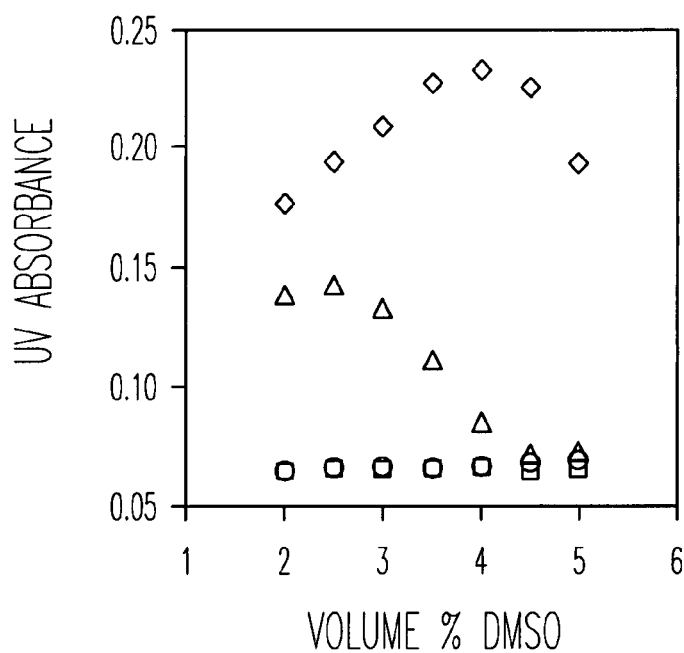

Another prediction from the solvophobically driven folding is that demixing and folding should be easier in the partially miscible DMSO/(ethyl acetate/hexane=1/2) mixtures than the completely miscible DMSO/CCl$_4$. Indeed, as shown in FIG. 3B, the pentamer, which seems to be unable to fold in DMSO/CCl$_4$ mixtures, displays the heptamer-like sigmoidal transitions in the ternary solvents. Not surprisingly, the monomer and the trimer show little changes in their UV signal with variation of DMSO, as they are too short to fold. The heptamer, on the other hand, remains in the higher-absorbing state throughout the experiments. However, instead of a sigmoidal curve, the UV absorbance of the heptamer in the ternary solvents shows an initial increase and a subsequent decrease (FIG. 3B). This behavior is actually reasonable with the proposed folding process. According to FIG. 3B, the pentamer is mostly folded with up to 3% DMSO.

Because the folded heptamer is more stable and has a longer internal cavity, it should enrich DMSO more efficiently than the pentamer. Provided higher absorption of the NBD group is caused by local enrichment of DMSO, the heptamer should have higher absorption as well. During the initial increase in DMSO, the heptamer is mostly folded. Therefore, an increase in DMSO in the bulk solvent should increase its local concentration even more (and enhance the UV absorption of NBD). Further increase in DMSO, however, would unfold the heptamer and thus should decrease the local concentration of DMSO (and reduce the UV absorption of NBD). In ethyl acetate/hexane (1/2), no more than about 5% DMSO can be added due to limited miscibility. Otherwise, all four oligomers would eventually have the same UV absorption, as they did in the DMSO/CCl$_4$ mixtures.

Figure 4A:
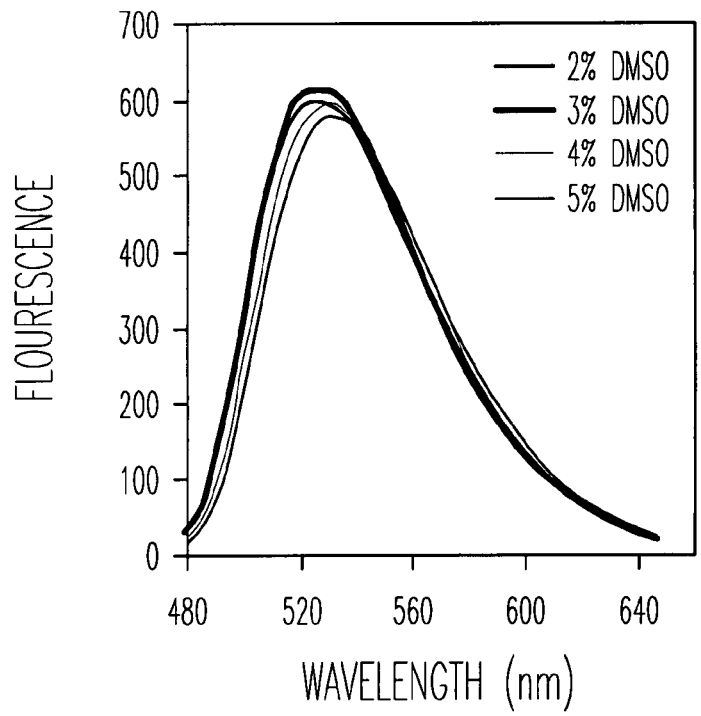
FIGS. 4A and 4B show fluorescence spectra of (A) monomer 1 and (B) heptamer 4 in DMSO/CCl$_4$ mixtures. [1]=[4]=10 µM.
Figure 4B:
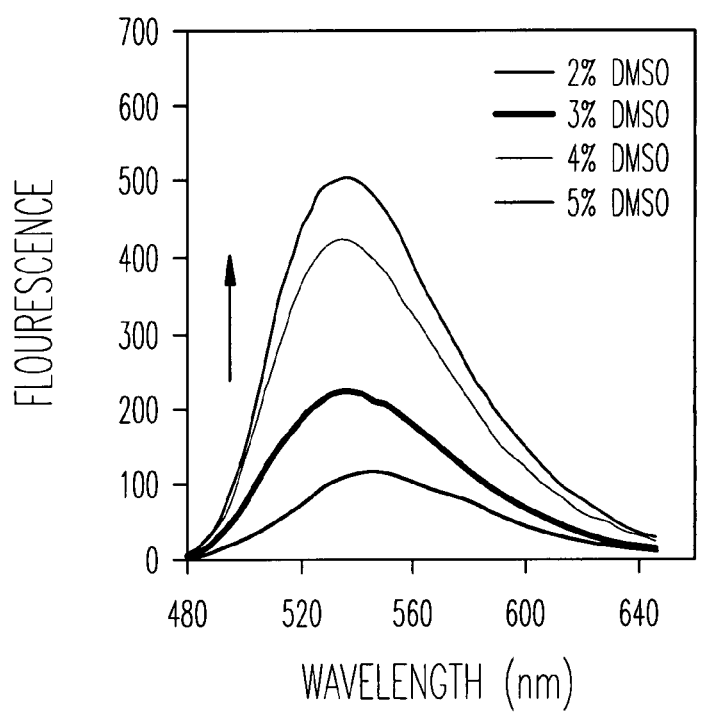
Figure 5A:
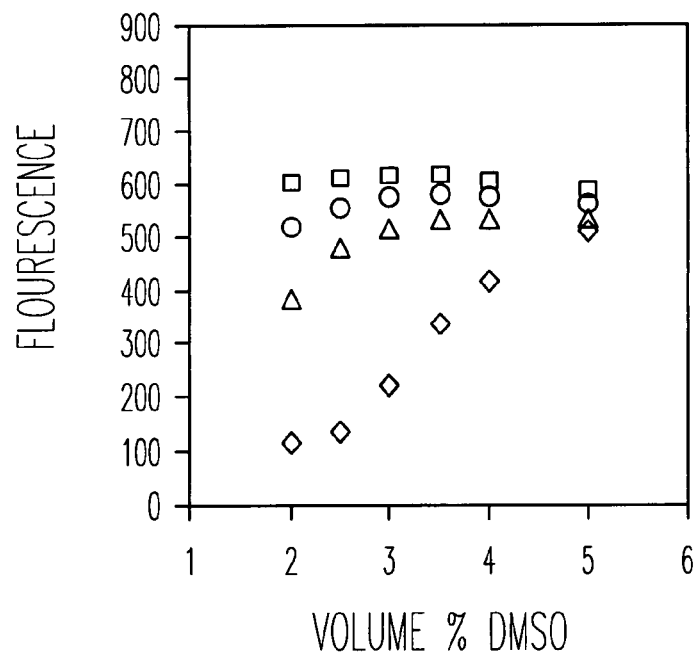
FIGS. 5A and 5B show the maximum fluorescence intensity of monomer 1 (□), trimer 2 (○), pentamer 3 (Δ), and heptamer 4 (◊) as a function of DMSO in (A) CCl$_4$ and (B) ethyl acetate/hexane=1/2. [Oligomer]=10 µM.
Figure 5B:
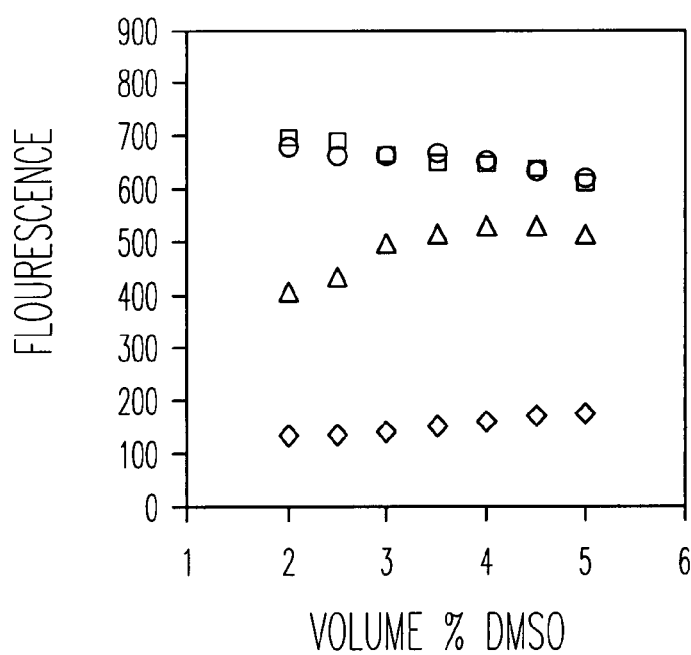

Similar solvent effects were also observed in the fluorescence spectra. For example, the emission of the monomer is nearly unchanged with 2-5% DMSO in CCl$_4$ (FIG. 4A), but that of the heptamer starts out with an intensity 1/6 of that of the monomer in 2% DMSO and gradually gains strength, approaching that of the monomer in 5% DMSO. In addition, chain-length dependencies similar to those found in the UV spectra were also observed in the fluorescence spectra (FIG. 5), except that the higher-absorbing (folded) state in the UV spectra corresponds to the lower-fluorescing state in the fluorescence spectra.

The UV and fluorescence data are consistent with solvent-induced folding/unfolding of the cholate oligomers. Importantly, the unusual behavior of the longer oligomers does not depend on their concentrations. The sample concentration was 10 µM for the UV spectra and 2 µM for the fluorescence spectra. When an even lower concentration (0.2 µM) is used, similar DMSO-dependent fluorescence was observed for the heptamer but not for the monomer. Therefore, the "unusual" solvent effects in the longer oligomers were unlikely a result of concentration-dependent aggregation or disordered conformational changes, which are unlikely to be cooperative. Instead, they probably come from cooperative, helix-coil transitions. The following experiments provide additional evidence for this hypothesis.

Fluorescence Quenching of NBD-Labeled Oligomeric Cholates. If folding indeed creates internal hydrophilic cavities, the emission of the NBD group should be efficiently quenched by a hydrophilic quencher (11) and the quenching efficiency should increase with chain lengths, as the folded state is more stable for the longer oligomers. Quenching by the parent quencher, TEMPO (12), however, should be independent of chain lengths because its hydrophobicity forbids it to enter the cavity generated by folding.

11

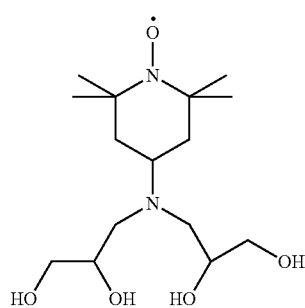

12

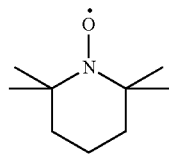

Figure 6A:
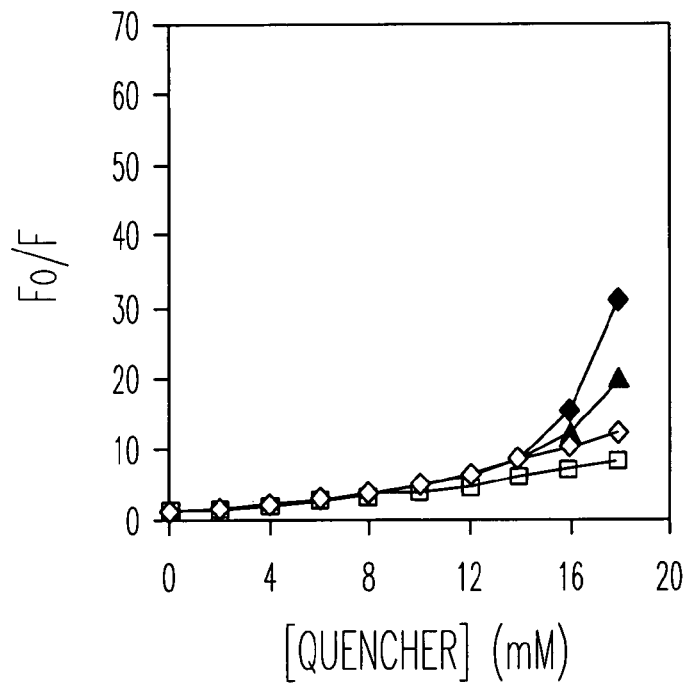
FIGS. 6A and 6B show quenching of monomer 1 (□), trimer 2 (◊), pentamer 3 (▲), and heptamer 4 (◆) by hydrophilic quencher 11 in (A) 5% DMSO/CCl$_4$ and (B) 2% MeOH/CCl$_4$. [Oligomer]=12.5 µM.

FIG. 6A shows the quenching of 1-4 by 11 in 5% DMSO/CCl$_4$. Five percent DMSO was used because the quencher had to be used in millimolar concentrations but was fairly insoluble with lower DMSO. As expected, positive deviations from linear Stern-Volmer quenching profiles are observed, and quenching efficiency clearly increased with the chain length. The basic conclusions drawn from FIG. 6—that the longer the chain length, the more stable the folded state (and the better it can bind a hydrophilic guest)—are the same from the UV and fluorescence studies. Subtle differences do exist, particularly for the pentamer. For example, UV (FIG. 3A) seems to indicate that the pentamer is completely unfolded in DMSO/CCl$_4$. Fluorescence (FIG. 5A) appears to suggest that pentamer is partly folded at least in 2% DMSO. FIG. 6A, on the other hand, clearly shows enhanced quenching of the pentamer even in 5% DMSO/CCl$_4$, indicating that the pentamer is folded even in 5% DMSO/CCl$_4$. Such "discrepancies" between different experimental methods are quite normal because these methods probably detect different folding-related events (e.g., DMSO enrichment or binding of a hydrophilic guest) and are expected to have different sensitivities for the conformational transitions. In addition, these events may not be synchronous and have their own unique solvent-dependences. Therefore, the observed solvent effects are "composite" effects from multiple factors and should not be simply assigned to the folding/unfolding equilibrium.

Figure 6B:
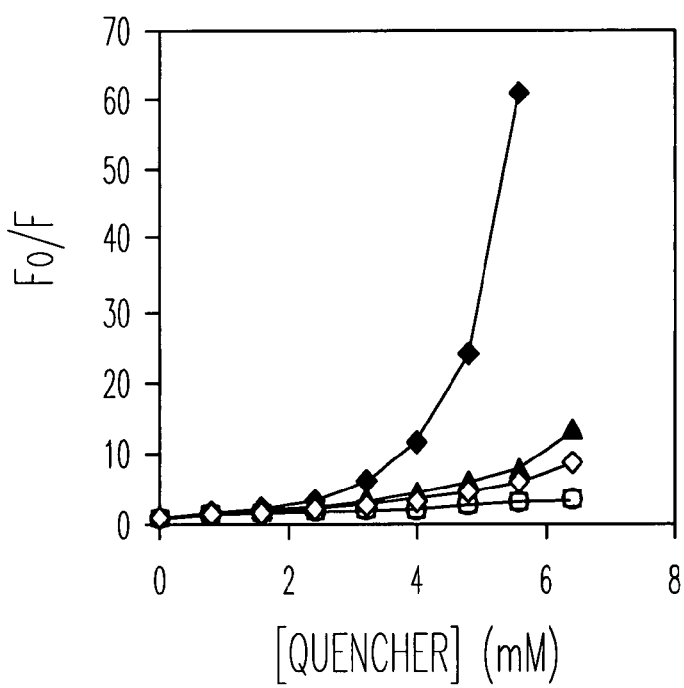

Little enhancement in quenching of 1-4 by 11 is observed in 5% methanol/CCl$_4$. In 2% methanol, however, similar positive deviations appear again (FIG. 6B). There are three important differences between the two solvent mixtures: (a) Quenching efficiency is much higher for the same cholate oligomer in 2% methanol/CCl$_4$ than in 5% DMSO/CCl$_4$. For example, the fluorescence of heptamer 4 (♦) is reduced by 60-fold with 5.6 mM of 11 in 2% methanol (FIG. 6B) but only by <3-fold with the same concentration of the quencher in 5% DMSO. Therefore, binding between the heptamer and the quencher is much stronger in the former solvent. (b) When the most "foldable" heptamer (+) and the least "foldable" monomer (□) are compared, difference in quenching is only obvious with >12 mM of quencher in 5% DMSO but is clearly observable at 3 mM in 2% methanol. Apparently, the quencher has difficulty entering the binding site formed by the heptamer in 5% DMSO. This difference again suggests stronger binding in 2% methanol than in 5% DMSO. (c) Difference between the more stable heptamer (♦) and the less stable pentamer (▲) is much larger in 2% methanol than in 5% DMSO. This result, together with the lack of quenching enhancement in 5% methanol, suggests that DMSO/CCl$_4$ mixtures are more amenable to folding than methanol/CCl$_4$ mixtures.

Interestingly, very similar solvent effects were observed in the cholate-based calixarene basket. The basket binds phenyl β-D-glucopyranoside in the reversed-micelle-like conformation. Binding is fairly strong (Ka=290 M$^{-1}$) in 10% methanol/CCl$_4$ but is too weak to be detected in 10% DMSO/CCl$_4$, even though the latter mixture stabilizes the guest-binding conformer more than the former. This unusual solvent effect is actually quite normal, if one realizes that preferential solvation of the hydrophilic faces of cholates by DMSO or methanol is responsible for both the formation of the reversed-micelle-like conformer and its binding property. Whereas stronger preferential solvation stabilizes this conformer initially, it also makes it an inferior host during subsequent binding, because the strongly solvating DMSO molecules cannot be displaced easily by the guest. In other words, for a conformationally mobile, solvophobically based supramolecular host, the same interaction that helps the formation of the ordered conformer actually works against it during binding.

Figure 7:
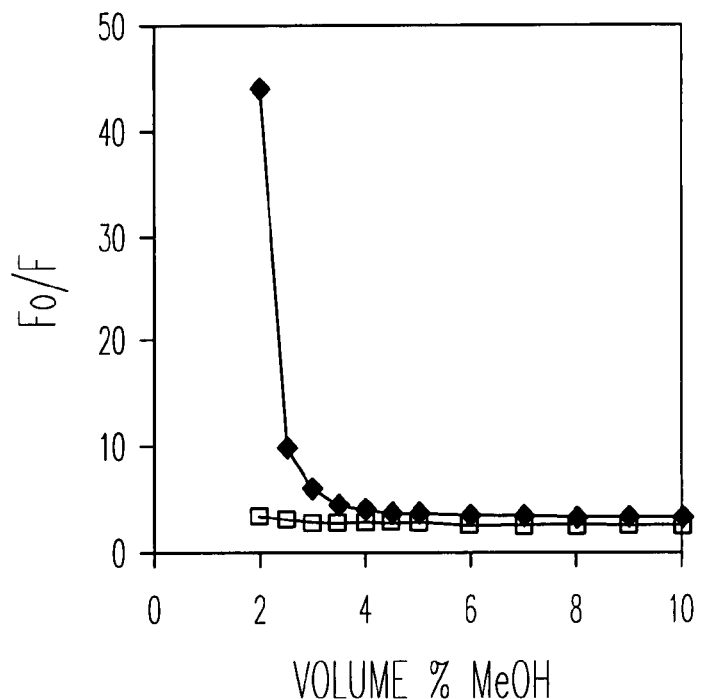
FIG. 7 shows quenching of monomer 1 (□) and heptamer 4 (◆) by hydrophilic quencher 11 as a function of the percentage of methanol in CCl$_4$. [1]=[4]=12.5 µM, [11]=5.6 mM.

To further explore the effect of the polar solvent on quenching, the heptamer or the monomer was mixed with the hydrophilic quencher 11 in 2% methanol/$CCl_4$ and then added aliquots of methanol to this mixture. The two oligomers differ enormously in their response, as shown in FIG. 7. Quenching efficiency for the monomer stays nearly the same with 2-10% of methanol, but that for the heptamer shows a huge decrease within a very narrow range (2-3%) of methanol percentage. In solvophobically based hosts with rigid structures, binding energies typically correlate linearly to the solvent solvophobicity parameters (which are linearly related to volume percentages in binary solvent mixtures). Abraham, M. H. *J. Am. Chem. Soc.* 1982, 104, 2085-2094; Abraham, M. H.; Grellier, P. L.; McGill, R. A. *J. Chem. Soc., Perkin Trans.* 2 1988, 339-345; Schneider, H.-J.; Kramer, R.; Simova, S.; Schneider, U. *J. Am. Chem. Soc.* 1988, 110, 6442-6448. Therefore, the abrupt solvent response cannot be explained by changes in solvent solvophobicity alone. Instead, unfolding of the heptamer is the most likely reason. The conclusion is consistent with the earlier UV and fluorescence data.

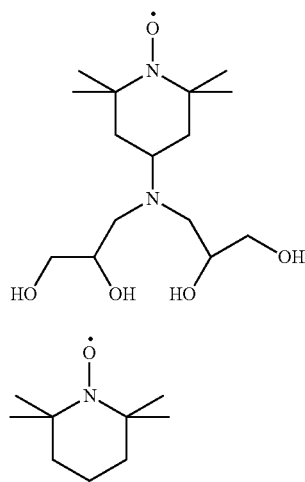

11

12

As expected, when the hydrophobic compound 12 is used as the quencher, quenching becomes much less efficient, and the difference between the heptamer and the monomer completely disappeared in either DMSO/$CCl_4$ or MeOH/$CCl_4$ mixtures. This is in line with the folding model because the hydrophilic cavity created by folding cannot bind hydrophobic guests.

Figure 8:
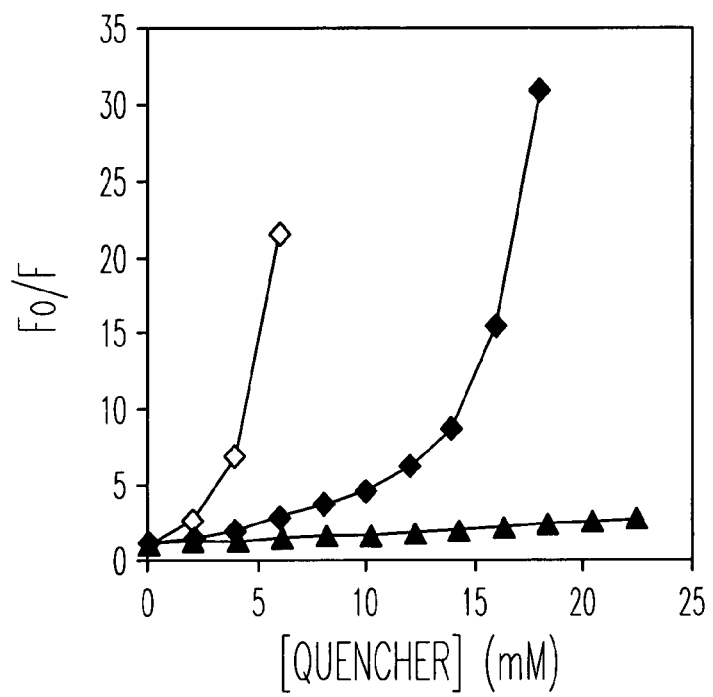
FIG. 8 shows quenching of heptamer 4 by hydrophilic quencher 11 with 5% DMSO in ethyl acetate/hexane=1/2 (◊), CCl$_4$ (◆), and ethyl acetate (▲). [Oligomer]=12.5 µM.

Finally, to probe the effect of solvent miscibility on folding, quenching in 5% DMSO with three different nonpolar solvents was studied: ethyl acetate/hexane (1/2), $CCl_4$, and ethyl acetate. As discussed above, folding should be most favorable in ethyl acetate/hexane=1/2 due to easy demixing of DMSO. Even though both ethyl acetate and $CCl_4$ are miscible with DMSO at all ratios, DMSO certainly is more "like" the polar ethyl acetate than the nonpolar $CCl_4$. Therefore, demixing of DMSO and folding should be easier in the latter. The data support this theory, with much more efficient quenching in ethyl acetate/hexane=1/2 than in $CCl_4$ (see FIG. 8). The heptamer is probably completely unfolded in 5% DMSO/ethyl acetate, as no quenching enhancement is observed at all in this mixture.

Characterization of Conformations by Fluorescence Resonance Energy Transfer (FRET). The data so far suggest that the cholate foldamers (with >5 repeating units) form internal hydrophilic cavities upon folding. In agreement with helix-coil transitions, the folding seems to be cooperative. Examination of the molecular models suggests that three repeating units make one turn in the cholate foldamers. According to the models, the end-to-end distance is ca. 1 nm for the hexamer and ca. 2 nm for both the pentamer and the heptamer in the fully folded states. These distances can be easily distinguished by FRET, whose transfer efficiency (E) is related to the donor-acceptor (D-A) distance (r) by equation $E=R_0^6/(R_0^6+r^6)$, in which $R_0$ is the Forster distance for a specific D-A pair. Because typical $R_0$ (2-6 nm) is comparable to the diameter of many proteins, FRET has been widely used in the conformational study of biomolecules. Stryer, L. *Annu. Rev. Biochem.* 1978, 47, 819-846; Selvin, P. R. *Methods Enzymol.* 1995, 246, 300-334; Lakowicz, J. R. *Principles of Fluorescence Spectroscopy,* 2nd ed.; Kluwer: New York, 1999; Chapter 13. Note that distance measurement has been used to study foldamer conformations as well. For example, Moore and co-workers characterized the helical pitch of their m-phenylene ethynylene foldamers using distance-dependent spin-spin interactions.

Figure 9:
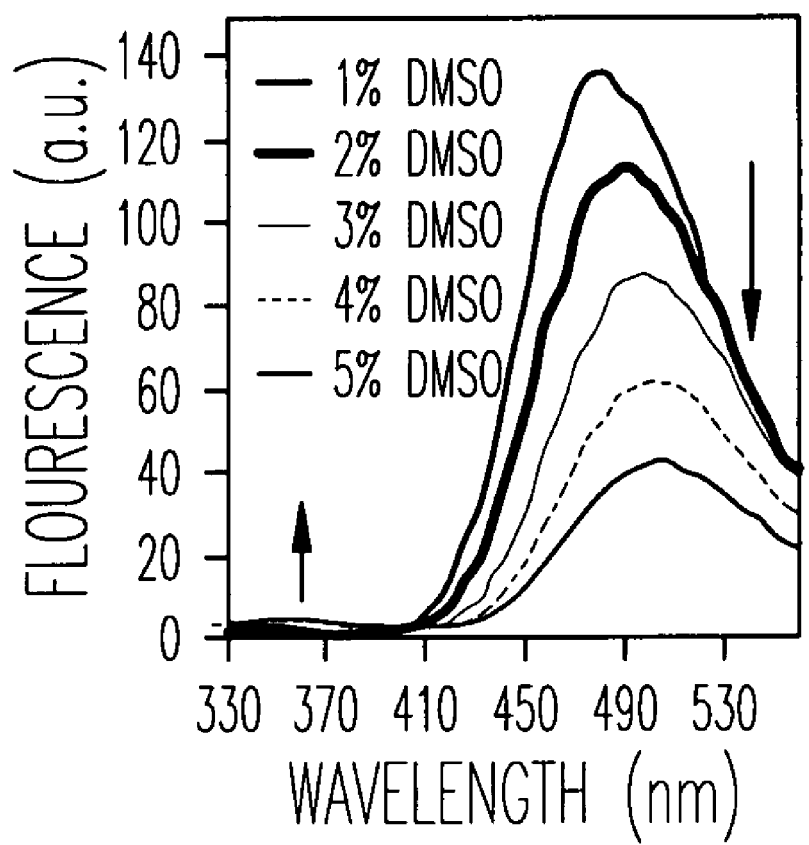
FIG. 9 shows fluorescence spectra of HXDA 6 in ethyl acetate/hexane (1/2) with different percentages of DMSO.

A naphthalene-Dansyl D-A pair (Stryer, L.; Haugland, R. P. *Proc. Natl. Acad. Sci. U.S.A.* 1967, 58, 719-726) and the synthesized pentamer-DA 5 (PDA), hexamer-DA 6 (HXDA), heptamer-DA 7 (HPDA), monomer-A 8 (MA), and monomer-D 9 (MD). Because $CCl_4$ interferes with the fluorescence of naphthalene, the ternary DMSO/ethyl acetate/hexane mixture was used instead. As shown in FIG. 9, FRET is clearly observable in HXDA in 1% DMSO, with the donor emission at 350 nm close to zero and the acceptor emission at 480 nm extremely strong. FRET becomes less efficient with higher DMSO, as shown by an increase of the donor emission and a decrease of the acceptor emission. Reduction in FRET suggests an increase in the D-A distance, consistent with a transition from a more compact folded helix to an unfolded coil.

Figure 10A:
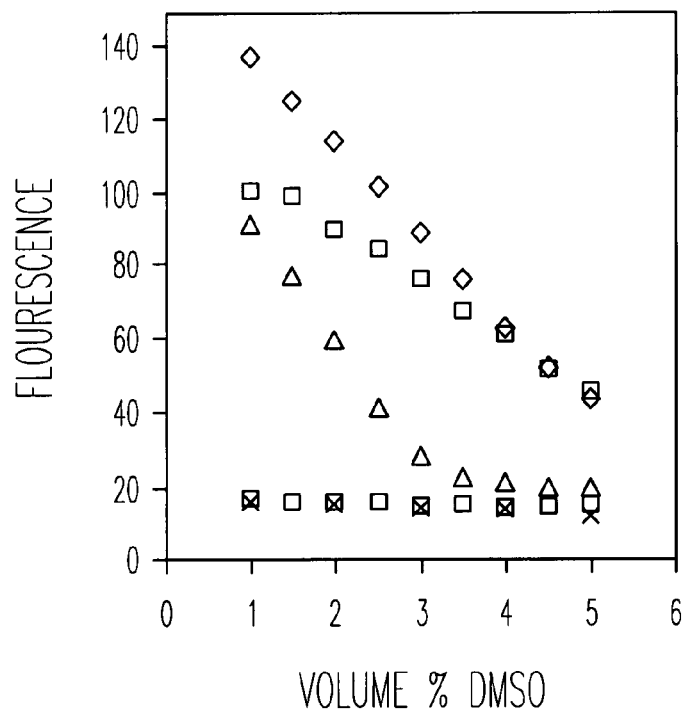
FIG. 10A shows the maximum emission intensity of the acceptor in pentamer-DA 5 (Δ), hexamer-DA 6 (◊), heptamer-DA 7 (upper □), monomer-A 8 (lower □), and a 1:1 mixture (8+9) of monomer-A and monomer-D (x) as a function of the volume percentage of DMSO in ethyl acetate/hexane (1/2).
Figure 10B:
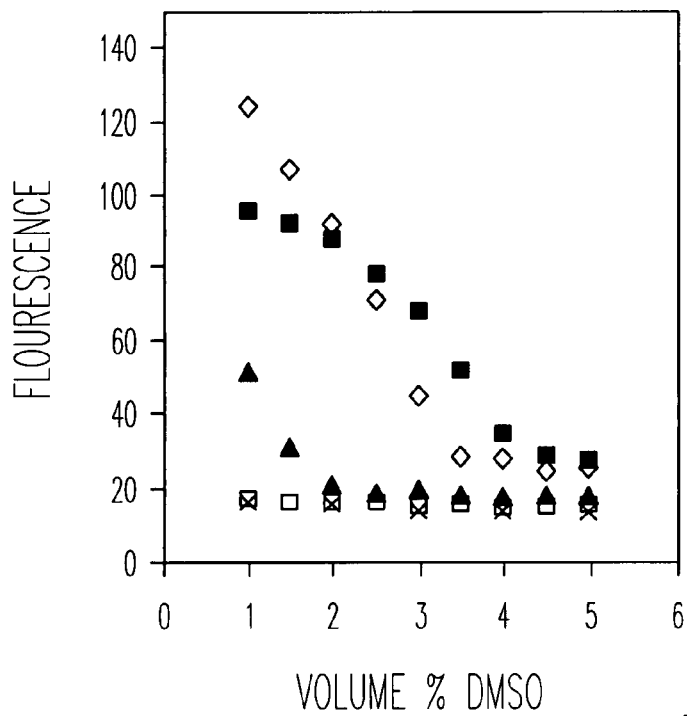
FIG. 10B shows the maximum emission intensity of the acceptor in pentamer-DA 5 (◆), hexamer-DA 6 (◊), heptamer-DA 7 (■), monomer-A 8 (□), and a 1:1 mixture (8+9) of monomer-A and monomer-D (x) as a function of the volume percentage of DMSO in ethyl acetate/hexane (1/1).

The donor emission in the systems tested was very weak. Therefore, the acceptor emission was used as a relative indicator for the transfer efficiency—a stronger acceptor emission corresponds to a more efficient FRET. FIGS. 10A and 10B show the maximum emission intensity of the acceptor vs. DMSO percentage in two mixtures (1:2 and 1:1) of ethyl acetate/hexane.

Several important conclusions can be drawn from FIG. 10. First, the acceptor emission of MA 8 is the same in the absence (□) or the presence (x) of MD 9. Thus, no intermolecular transfer occurs under the experimental conditions in either solvent system. Also, the two curves for MA and (MA+MD) are nearly flat, indicating that the effect of DMSO on the acceptor emission is small. Second, FRET becomes less efficient in all three oligomers (5-7) with higher DMSO. On the basis of the slopes of the curves, stability of the folded state follows the order of heptamer>hexamer>pentamer. Third, stability of all three foldamers decreases in the more miscible DMSO/(ethyl acetate/hexane=1/1) mixtures. For example, the pentamer loses its folded conformer with about 4%

DMSO in ethyl acetate/hexane=1/2 but does so with as little as 2% DMSO in ethyl acetate/hexane=1/1. This behavior is fully consistent with the miscibility hypothesis. Fourth, the hexamer has the most efficient FRET in both mixtures of ethyl acetate/hexane with 1% DMSO but, because of its lower stability compared to the heptamer, ends up with lower FRET than the heptamer. Thus, the hexamer has a shorter D-A distance than the heptamer because it has a collapsed conformation. It is, however, quite unusual for the hexamer to have a shorter D-A distance than the pentamer. The result once again confirms the helix-folding model, which predicts the closest end-to-end distance in the hexamer if three repeating units make one turn and the hexamer has two full turns. Such a periodicity is probably a result of the curvature of monomer created by the cis-fused A-B rings of the cholate backbone. Similar preference for trimeric structures was discovered by Sanders and co-workers, who reported trimeric cyclic cholate esters were more stable than other cyclic oligomers under thermodynamic control. Brady, P. A.; Bonar-Law, Ri. P.; Rowan, S. J.; Suckling, C. J.; Sanders, J. K. M. *Chem. Commun.* 1996, 319-320.

Figure 11A:
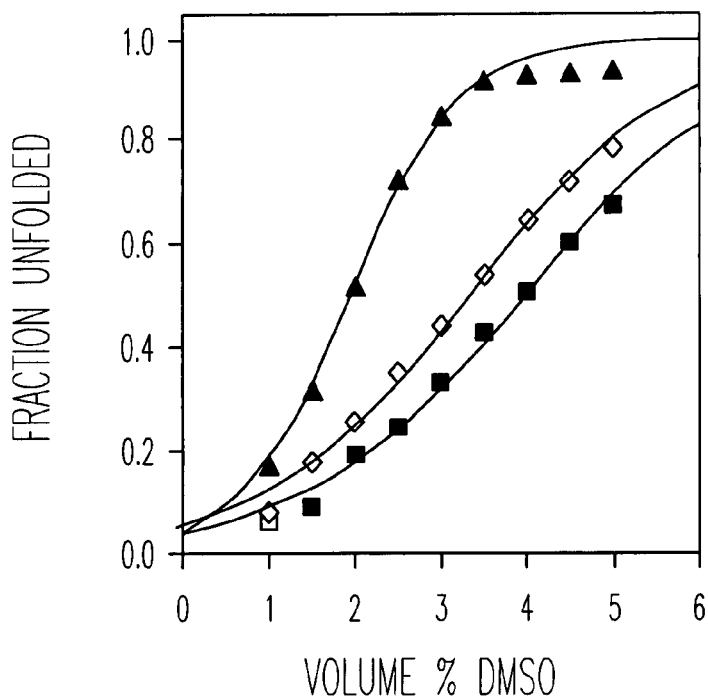
FIGS. 11A and 11B show the fraction of the unfolded pentamer-DA 5 (▲), hexamer-DA 6 (◊), and heptamer-DA 7 (■) as a function of the volume percentage of DMSO in (A) ethyl acetate/hexane (1/2) and (B) ethyl acetate/hexane (1/1). The theoretical curves are nonlinear least-squares fitting to a two-state transition model.
Figure 11B:
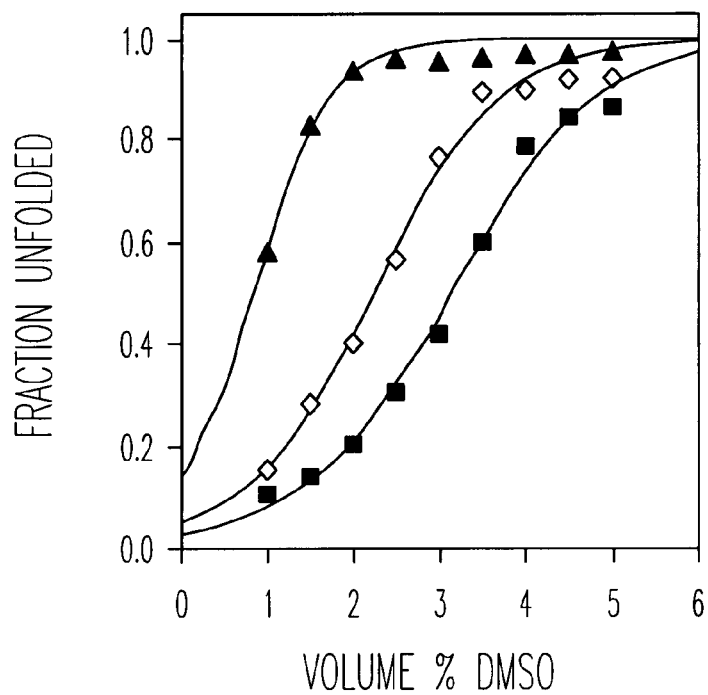
Figure 12A:
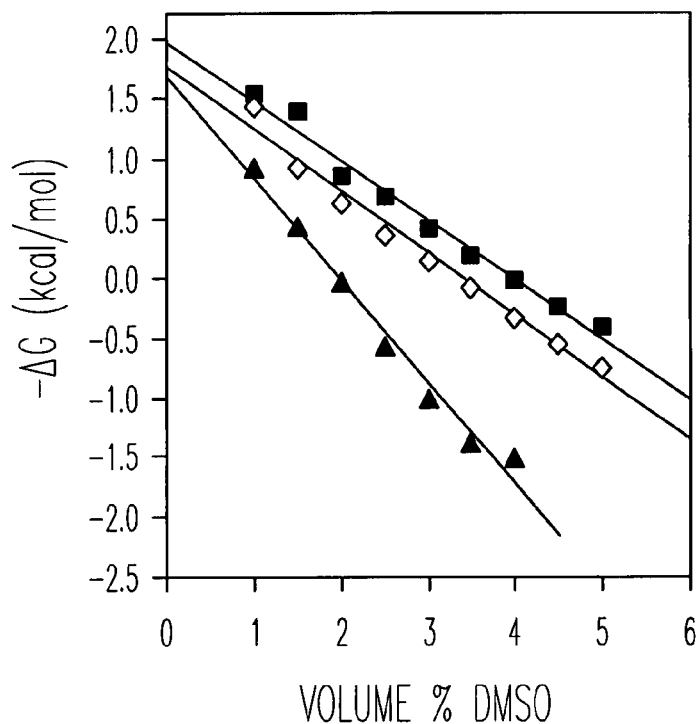
FIGS. 12A and 12B show the unfolding free energies for pentamer-DA 5 (▲), hexamer-DA 6 (◊), and heptamer-DA 7 (■) as a function of the volume percentage of DMSO in (A) ethyl acetate/hexane (1/2) and (B) ethyl acetate/hexane (1/1).
Figure 12B:
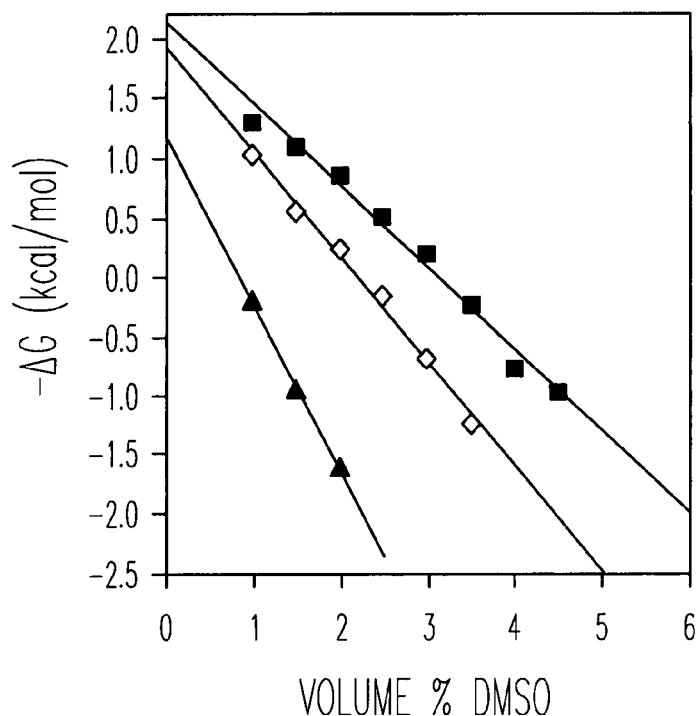

The curves in FIGS. 10A and 10B once again have sigmoidal shapes, suggesting cooperative transitions in these "solvent denaturation experiments." The experimental data fit quite well to a two-state model (equation 1). Pace, C. N. *Methods in Enzymology*; Hirs, C. H. W., Timasheff, S, N., Eds.; Academic Press: New York, 1986; Vol. 131, pp 266-280; Pace, C. N.; Shirley, B. A.; Thomson, J. A. *Protein Structure: A Practical Approach*; Creighton, T. E., Ed.; IRL Press: New York, 1989; pp 311-330; Prince, R. B.; Saven, J. G.; Wolynes, P. G.; Moore, J. S. *J. Am. Chem. Soc.* 1999, 121, 3114-3121. As shown in FIGS. 11A and 11B, the stability of the foldamer follows the order of heptamer (■)>hexamer (◊)>pentamer (▲). In addition, the free energies in the transition regions of the solvent denaturation curves are linearly related to the concentration of DMSO (FIGS. 12A and 12B). Such behavior is frequently seen in proteins which display two-state transitions in their folding and unfolding. Chan, H. S.; Bromberg, S.; Dill, K. A. *Philos. Trans. R. Soc. London, Ser. B* 1995, 348, 61-70; Pace, C. N. *Methods in Enzymology*; Hirs, C. H. W., Timasheff, S, N., Eds.; Academic Press: New York, 1986; Vol. 131, pp 266-280. (b) Pace, C. N.; Shirley, B. A.; Thomson, J. A. *Protein Structure: A Practical Approach*; Creighton, T. E., Ed.; IRL Press: New York, 1989; pp 311-330.

It is quite remarkable that the cholate oligomers can display cooperative folding with as few as five repeating units.

(1)

From the curves in FIGS. 11 and 12, the thermodynamic parameters shown in Table 2 were extracted for the folding/unfolding equilibrium in all three cholate foldamers.

TABLE 2

Values of $\Delta G_0$ and m Determined from Solvent Denaturation Curves[a]

| Entry | Chain Length | Solvent Composition | $\Delta G_0$ (kcal/mol) | m (kcal/mol) |
|---|---|---|---|---|
| 1 | n = 5 | DMSO in ethyl acetate/hexane (1/2) | 1.8 ± 0.1 (1.7) | 0.93 ± 0.06 (0.86) |

TABLE 2-continued

Values of $\Delta G_0$ and m Determined from Solvent Denaturation Curves[a]

| Entry | Chain Length | Solvent Composition | $\Delta G_0$ (kcal/mol) | m (kcal/mol) |
|---|---|---|---|---|
| 2 | n = 6 | DMSO in ethyl acetate/hexane (1/2) | 1.7 ± 0.1 (1.8) | 0.50 ± 0.02 (0.52) |
| 3 | n = 7 | DMSO in ethyl acetate/hexane (1/2) | 1.9 ± 0.1 (2.0) | 0.47 ± 0.02 (0.50) |
| 4 | n = 5 | DMSO in ethyl acetate/hexane (1/1) | 1.1 ± 0.2 (1.2) | 1.35 ± 0.20 (1.42) |
| 5 | n = 6 | DMSO in ethyl acetate/hexane (1/1) | 1.8 ± 0.1 (1.9) | 0.81 ± 0.06 (0.89) |
| 6 | n = 7 | DMSO in ethyl acetate/hexane (1/1) | 2.2 ± 0.1 (2.1) | 0.71 ± 0.04 (0.69) |

[a]Data with errors are determined from FIG. 11 by nonlinear least-squares fitting to a two-state transition model. Data in parentheses are determined from FIG. 12 by linear fitting of the unfolding free energies as a function of denaturant concentration. The data slightly underestimate the thermodynamic stability of the folded states. See Example 1 for details of data analysis.

In both solvents, the foldamers become more resistant to DMSO denaturation with longer chain-length, as m decreases with increasing chain length (entries 1-3 and 4-6). The $\Delta G_0$ values generally reflect the same trend of stability (i.e., heptamer>hexamer>pentamer). Also, m is smaller for the same foldamer in the less miscible DMSO/(ethyl acetate/hexane=1/2) than the more miscible DMSO/(ethyl acetate/hexane=1/1)—compare entries 1 vs. 4, 2 vs. 5, and 3 vs. 6. Therefore, the folded conformation does become more stable as demixing of the polar solvent becomes easier.

Figure 13:
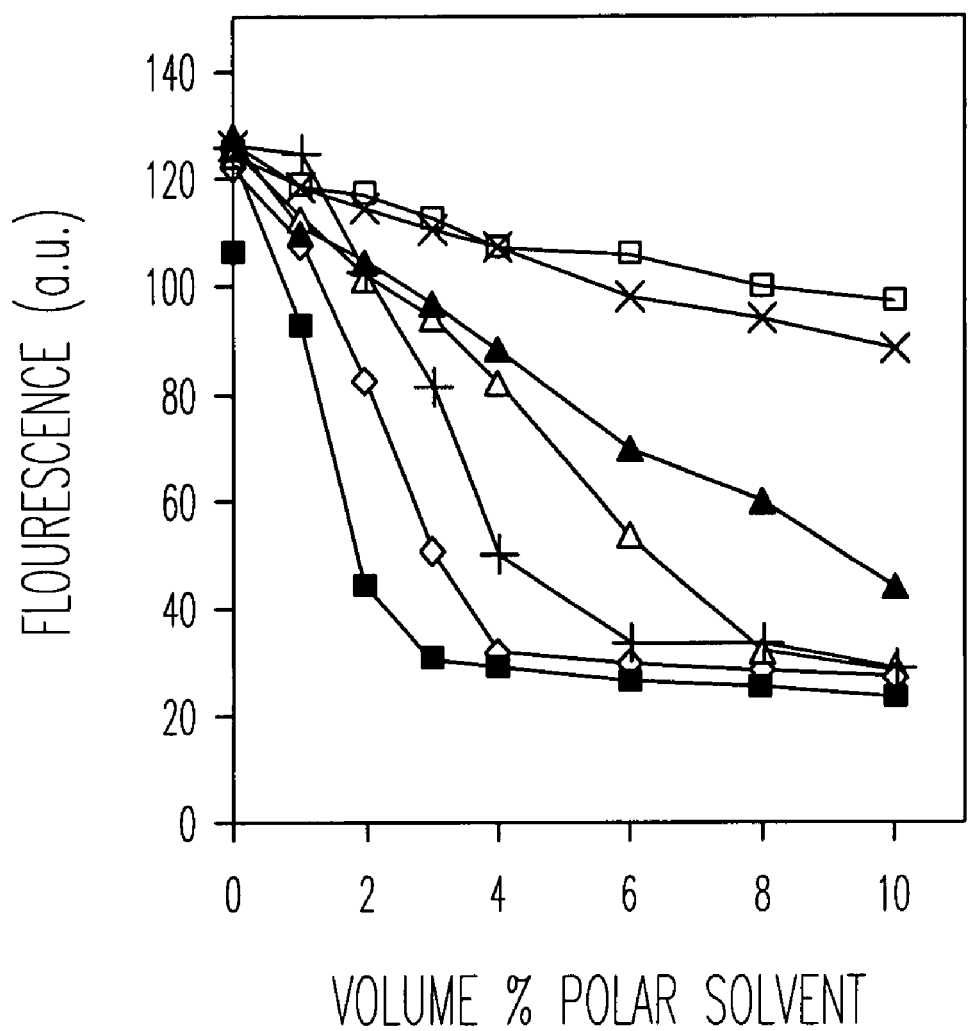
FIG. 13 shows the maximum emission intensity of the acceptor in hexamer-DA 6 as a function of the volume percentage of different polar solvents: methanol (■), ethanol (◊), N,N-dimethylformamide (+), isopropanol (Δ), tert-butyl alcohol (▲), dioxane (X), and tetrahydrofuran (□). The initial condition is 1% DMSO in ethyl acetate/hexane (1/2). [6]=2.0 µM.

An interesting feature of the present system is the role played by DMSO. At low concentrations, it is needed for both solubility and preferential solvation of the hydrophilic faces of cholates—the latter provides the fundamental driving force to folding. At higher concentrations, however, it destabilizes the folded conformer, with one percent change in DMSO shifting the folding free energy by 0.5-1.4 kcal/mol. One percentage change in solvent composition is unlikely to significantly change bulk solvent properties such as dielectric constants. Quite possibly, DMSO is enriched around the cholate foldamers by their polar hydroxyl and amide groups. Two types of interactions between DMSO and the cholate oligomers may exist. One type, serving to contract the cholate chains, is from the DMSO molecules within the hydrophilic cavities. These DMSO molecules selectively solvate the R faces of the cholates and essentially act as solvophobic "glue" to pull the otherwise extended chains together to form the helix. The other type is from those DMSO molecules outside the cavities, presumably serving to solvate the amide bonds and relax the cholate chains. It is probably the balance between the two that determines the folding/unfolding equilibrium. The ultrahigh sensitivity of the foldamers toward DMSO is unusual but is not unexpected considering similar behavior of our amphiphilic basket. Ryu, E.-H.; Zhao, Y. *Org. Lett.* 2004, 6, 3187-3189. The difference is that the latter is much better preorganized and, in consequence, requires higher percentage of DMSO to induce the conformational change. Many other polar solvents can unfold the cholate helixes (see FIG. 13). In general, the unfolding ability of the solvent seems to follow its polarity and/or hydrogen-bonding ability. For example, the unfolding ability of the solvent follows the order of methanol>ethanol>2-propanol>tert-butyl alcohol. For aprotic solvents, neither dioxane nor tetrahydrofuran has strong influence on the folding/unfolding equilibria (with dioxane being a slightly stronger denaturant among the two). N,N-Dimethylformamide, on the other hand, has very strong unfolding abilities, probably due to its strong hydrogen-bonding ability to solvate the amide linkages of the cholate foldamers.

Conclusions

The cholate oligomers can be synthesized easily from the amino-derived cholic acid using standard amide coupling reactions. The UV and the fluorescence studies of the NBD-labeled oligomeric cholates suggest cooperative conformational transitions in the longer oligomers (n≧5) from a higher-absorbing, lower-fluorescing state to a lower-absorbing, higher-fluorescing state, as the polar solvent (DMSO) is increased in a mostly nonpolar solvent mixture. The fluorescence-quenching experiments demonstrate that the higher-absorbing, lower-fluorescing conformer has internal hydrophilic cavities capable of binding a hydrophilic quencher. Binding affinity increases with the chain length. In addition, the binding site is quickly destroyed with even a few percent increase of the polar solvent. These data are consistent with folding of the cholate oligomers into helix structures with hydrophilic internal cavities in low DMSO and unfolding of the helix in high DMSO. Intermolecular aggregation is probably not important under the experimental conditions, as the changes in fluorescence and UV are independent of concentration over 50-fold dilution (from 10 to 0.2 μM).

To gain more definitive evidence for the folding process, the two ends of the cholate oligomers were labeled with a fluorescent donor and an acceptor and used FRET to measure the end-to-end distance in the cholate oligomers. The results strongly support a helix model with three monomer units making one turn, as the hexamer has closer end-to-end distance than either the pentamer or the heptamer. The thermodynamic parameters for the folding reactions obtained from the FRET data are consistent with cooperative helix-coil transition. In general, the folded conformers become more stable with longer chain-length and are not as susceptible to the denaturant.

With three repeating units making one turn, the cholate foldamers can grow rapidly along the helical axis. This effect is further magnified by the large size of the repeating unit and it's sideway alignment along the helical axis. As a result, every three repeating units contribute ca. 0.7 nm to the helical axis. On the basis of Corey-Pauling-Koltun models, foldamers with six repeating units can form a hydrophilic cavity about 1 nm in diameter and nearly 1.5 nm in length. It is remarkable that nanosized structures can be obtained in these cholate foldamers available in just a few steps from the monomer. The dimension of the internal cavity, the easy synthesis, and the readily tunable folding/unfolding of the cholate foldamers should make them very useful as novel supramolecular hosts and responsive materials.

Example 3

Mercury-Binding Foldamers

This Example describes foldamers that can bind metal ions such as mercury.

Materials and Methods

Anhydrous tetrahydrofuan (THF) and methylene chloride were dried by passage through a column of activated alumina under compressed nitrogen. Cholic acid was crystallized from 95% ethanol. Methyl sulfoxide (DMSO, spectrophotometric grade, 99.9%) was purchased from Acros. Methanol, hexanes, and ethyl acetate were of HPLC grade and were purchased from Fisher Scientific. All other reagents and solvents were of A.C.S. certified grade or higher, and were used as received from commercial suppliers. All glassware and syringes were dried in an oven at least overnight prior to use. Routine $^1$H and $^{13}$C NMR spectra were recorded on a Varian VXR-300 and VXR-400 spectrometer. MALDI-TOF mass was recorded on a Thermobioanalysis Dynamo mass spectrometer. ESI-MS mass was recorded on Shimadzu LCMS-2010 mass spectrometer. UV-visible spectra were recorded at ambient temperature on an HP 8452 Spectrometer. Fluorescence spectra were recorded at ambient temperature on a Varian Cary Eclipse Fluorescence spectrophotometer.

Synthesis of Foldamer 10 and 40:

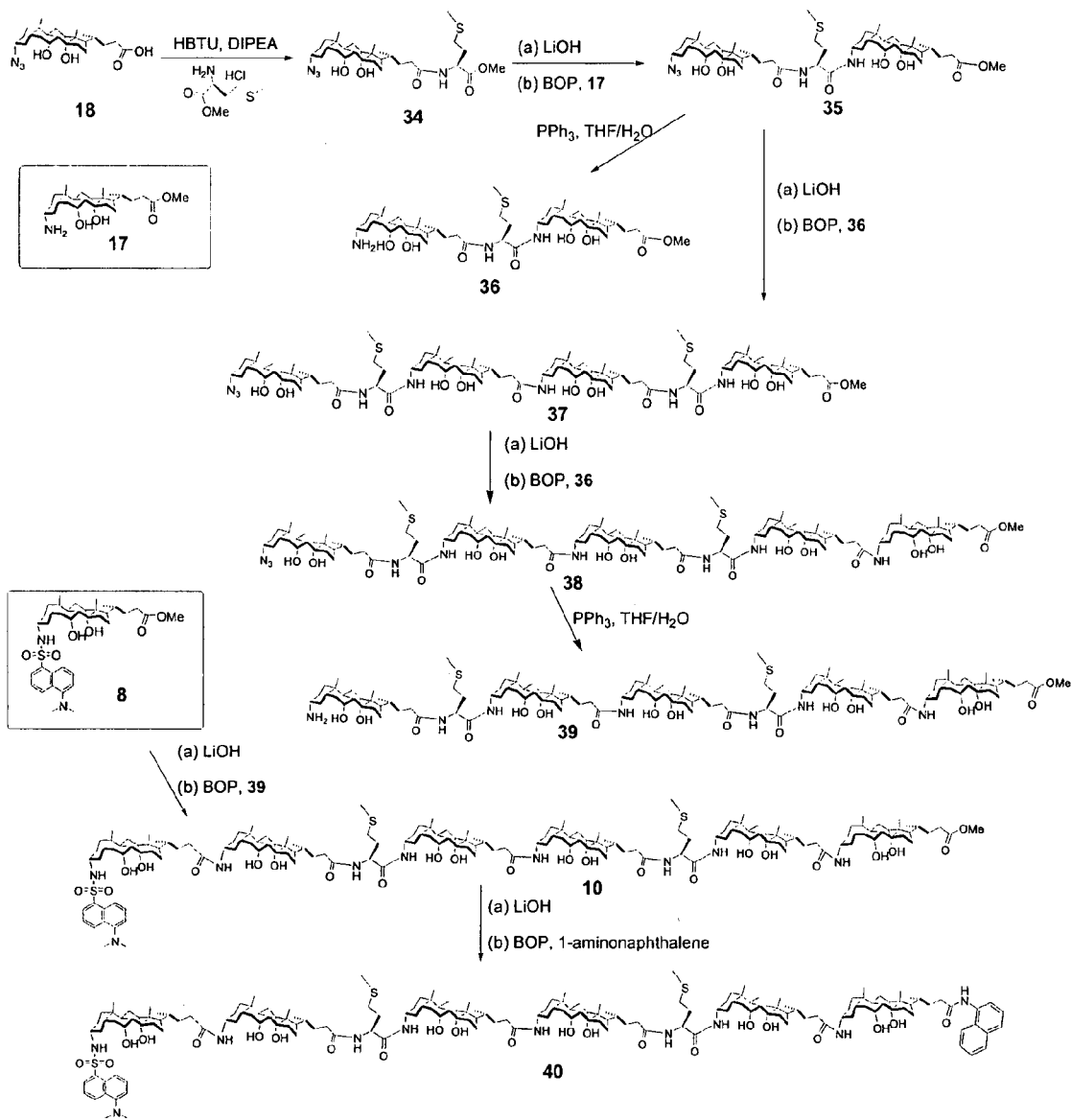

General procedure A—hydrolysis of the methyl ester. The methyl ester (1 mmol) was dissolved in methanol (5 mL) and was stirred with 2 M LiOH (5 mL, 10 mmol) at room temperature. Reaction was monitored by TLC and was complete in 5-24 h. Upon completion, the reaction mixture was quenched with 2 N HCl until pH=4-5. The solid was collected by suction filtration, washed with water, and dried under vacuum. The acid generally was used in the following step (i.e., amide coupling) without further purification.

General procedure B—reduction of the azide. The azide (1 mmol) and $PPh_3$ (1.5-5 mmol, higher amount was used for reduction of longer azide-terminated oligomers) were stirred in THF (5 mL) and $H_2O$ (0.1 mL) at 50° C. Reaction was monitored by TLC and was complete in 10-24 h. Solvents were removed by rotary evaporation. The residue was purified by column chromatography over silica gel.

General procedure C—amide coupling with BOP. The acid (1 mmol), the amine (1 mmol), and benzotriazol-1-yloxytris (dimethylamino) phosphonium hexafluorophosphate (BOP, 1.2 mmol) were dissolved in anhydrous DMF (3 mL). N,N-Diisopropylethylamine (DIPEA, 3 mmol) was added. The reaction mixture was stirred at room temperature (for lower oligomers) or 50° C. (for higher oligomers) for 10-42 h. The solvent was removed in vacuo and was purified by column chromatography over silica gel.

Compounds 8, 17, and 18 were synthesized as described in Example 1.

Synthesis of Compound 34. Compound 18 (1.019 g, 2.35 mmol) O-(Benzotriazol-1-yl)-N,N,N',N' tetramethyluronium hexafluorophosphate (HBTU, 0.937 g, 2.47 mmol), and DIPEA (1.234 g, 9.55 mmol) were dissolved in anhydrous DMF (10 mL). After 45 min, methionine methyl ester hydrochloride salt (0.510 g, 2.55 mmol) was added and the mixture was stirred for 10 h. The mixture was slowly added to a stirred solution of aqueous HCl (1.5 mL of 2N HCl in 60 mL water). The solid was collected by suction filtration, dried, and crystallized from EtOAc/hexane to give a white solid (0.992 g, 73%). m.p. 165.5-167.0° C. $^1$H NMR (400 MHz, $CDCl_3$, δ): 6.38 (d, J=7.8 Hz, 1H), 4.74 (m, 1H), 3.98 (s, 1H), 3.86 (s 1H), 3.67 (s, $CO_2CH_3$, 3H), 3.22-3.09 (m, 1H), 2.50 (d, J=7.6 Hz, 2H), 2.36-1.34 (series of m, 26H), 2.08 (s, $SCH_3$, 3H), 0.98-0.96 (d, J=5.8 Hz, 3H), 0.91 (s, 3H), 0.67 (s, 3H). $^{13}$C NMR (100 MHz, $CDCl_3$, δ): 174.40, 172.89, 73.48, 68.53, 61.46, 51.71, 51.57, 46.69, 42.11, 39.33, 35.75, 35.46, 35.02, 32.70, 31.85, 31.35, 30.28, 28.16, 27.98, 27.14, 26.55, 23.60, 22.64, 17.49, 15.70, 12.59. MALDI-TOFMS (m/z): $[M+H]^+$ calcd for $C_{30}H_{50}N_4O_5S$, 579.81; found, 576.35. $[M-N_2+H]^+$ calcd for $C_{30}H_{50}N_2O_5S$, 551.81; found, 547.39.

Synthesis of Compound 35. Compound 35 was prepared by the coupling between hydrolyzed 34 and amine 17 (General procedures A and C), and was purified by column chromatography over silica gel using $CH_2Cl_2$/MeOH (20:1) as the eluents (100% yield). $^1$H NMR (400 MHz, $CDCl_3$/$CD_3OD$=1:1, δ): 4.38 (m, 1H), 3.92 (br, 2H), 3.79 (s, 2H), 3.63 (s, $CO_2CH_3$, 3H), 3.55-3.44 (br, 1H), 3.16-3.07 (br, 1H), 2.45 (t, J=7.6 Hz, 2H), 2.42-0.99 (series of m, 50H), 2.04 (s, $SCH_3$, 3H), 0.95 (br, 6H), 0.86 (br, 3H), 0.65 (br, 6H). $^{13}$C NMR (100 MHz, $CDCl_3$/$CD_3OD$=1:1, δ): 175.57, 171.13, 171.09, 73.04, 68.13, 61.62, 52.65, 51.67, 50.11, 46.98, 46.80, 46.53, 42.14, 42.07, 41.78, 40.62, 39.57, 36.23, 35.95, 35.75, 35.59, 35.03, 34.92, 34.61, 33.12, 32.35, 31.85, 31.25, 31.14, 30.25, 28.33, 27.78, 27.52, 27.31, 26.89, 26.58, 23.37, 22.74, 22.62, 17.32, 17.18, 15.27, 12.54. MALDI-TOFMS (m/z): $[M+H]^+$ calcd for $C_{54}H_{90}N_5O_7S$, 969.38; found, 970.49. $[M-H_2O-N_2+H]^+$ calcd for $C_{54}H_{88}N_3O_6S$, 923.37; found, 920.94.

Synthesis of Compound 36. Compound 36 was prepared by reduction of compound 35 with $PPh_3$ (General procedure B), and was purified by column chromatography over silica gel using $CH_2Cl_2$/$CHCl_3$/MeOH (5:5:1) and then $CH_2Cl_2$/$CHCl_3$/MeOH/$Et_3N$ (5:5:2:0.2) as the eluents (98% yield). $^1$H NMR (400 MHz, $CDCl_3$/$CD_3OD$=1:1, δ): 4.38 (m, 1H), 3.95 (br, 2H), 3.78 (br, 2H), 3.62 (s, $CO_2CH_3$, 3H), 3.56-3.42 (br, 1H), 2.43 (t, J=7.6 Hz, 2H), 2.35-0.85 (series of m, 62H), 2.04 (s, $SCH_3$, 3H), 0.64 (br, 6H). $^{13}$C NMR (100 MHz, $CDCl_3$/$CD_3OD$=1:1, δ): 175.48, 174.93, 170.96, 73.05, 68.34, 68.18, 52.58, 51.71, 51.52, 49.93, 47.12, 47.03, 46.87, 46.56, 46.53, 42.05, 41.78, 39.60, 36.24, 36.02, 35.71, 35.57, 34.92, 34.69, 32.44, 31.87, 31.28, 31.14, 30.25, 28.33, 28.26, 27.73, 27.47, 26.52, 23.38, 22.75, 17.39, 17.26, 15.35, 12.59. MALDI-TOFMS (m/z): [M+H] calcd for $C_{59}H_{92}N_3O_8S$, 943.38; found, 943.40. [M+Na] calcd for $C_{59}H_{91}N_3NaO_8S$, 965.38; found, 965.90.

Synthesis of Compound 37. Compound 37 was prepared by coupling between hydrolyzed 35 and amine 36 (General procedures A and C), and was purified by column chromatography over silica gel using $CH_2Cl_2$/$CHCl_3$/MeOH (50:50:6) as the eluents (36% yield). $^1$H NMR (400 MHz, $CDCl_3$/$CD_3OD$=1:1, δ): 4.38 (m, 2H), 3.95 (br, 4H), 3.78 (br, 4H), 3.62 (s, $CO_2CH_3$, 3H), 3.56-3.42 (br, 3H), 3.16-3.08 (br, 1H), 2.43 (t, J=7.5 Hz, 4H), 2.35-1.05 (series of m, 100H), 2.04 (d, 2 ⊘$SCH_3$, 6H), 0.96 (br, 12H), 0.88 (br, 12H), 0.68 (br, 12H). $^{13}$C NMR (100 MHz, $CDCl_3$/$CD_3OD$=1:1, δ): 175.54, 175.08, 174.91, 171.03, 77.84, 73.04, 68.28, 68.18, 68.13, 61.65, 52.71, 51.74, 50.08, 47.14, 46.98, 46.80, 46.56, 42.04, 41.85, 41.78, 39.57, 36.88, 36.29, 35.94, 35.77, 35.58, 35.04, 34.93, 34.88, 34.67, 34.59, 33.19, 33.73, 33.18, 32.42, 32.16, 31.85, 31.29, 31.14, 30.24, 28.31, 27.77, 26.09, 26.57, 23.37, 22.75, 22.68, 17.38, 17.26, 15.35, 12.56. MALDI-TOFMS (m/z): $[M+H]^+$ calcd for $C_{107}H_{176}N_8NaO_{15}S_2$, 1901.72; found, 1900.59. $[M+H]^+$ calcd for $C_{107}H_{177}N_8O_{15}S_2$, 1879.72; found, 1873.78. $[M-N_2+H]^+$ calcd for $C_{107}H_{177}N_6O_{15}S_2$, 1851.72; found, 1851.28.

Synthesis of Compound 38. Compound 38 was prepared by the coupling between hydrolyzed 37 and amine 36 (General procedures A and C), and was purified by column chromatography over silica gel using $CH_2Cl_2$/$CHCl_3$/MeOH (5:5:1) as the eluents (44% yield). $^1$H NMR (400 MHz, $CDCl_3$/$CD_3OD$=1:1, δ): 4.38 (m, 2H), 3.92 (br, 5H), 3.79 (br, 5H), 3.64 (s, $CO_2CH_3$, 3H), 3.49 (br, 4H), 3.12 (br, 1H), 2.45 (t, J=7.5 Hz, 4H), 2.37-0.85 (series of m, 154H), 2.04 (d, 2×$SCH_3$, 6H), 0.66 (br, 15H). $^{13}$C NMR (100 MHz, $CDCl_3$/$CD_3OD$=1:1, δ): 175.56, 175.11, 175.00, 174.91, 174.39, 174.30, 171.03, 73.08, 68.29, 68.20, 68.11, 61.65, 57.70, 52.73, 51.73, 50.09, 49.69, 47.16, 47.03, 46.78, 46.56, 42.04, 41.89, 41.81, 39.57, 39.48, 36.35, 35.85, 35.81, 35.04, 34.95, 34.86, 34.68, 33.69, 33.19, 32.40, 32.16, 31.85, 31.31, 31.15, 30.23, 29.83, 28.26, 27.74, 27.49, 26.86, 26.57, 23.36, 22.72, 17.98, 17.34, 17.29, 15.32, 12.57. MALDI-TOFMS (m/z): $[M+Na]^+$ calcd for $C_{131}H_{215}N_9NaO_{18}S_2$, 2291.29; found, 2290.12. $[M+]^+$ calcd for $C_{131}H_{216}N_9O_{18}S_2$ 2269.29; found, 2263.04. $[M-N_2+H]^+$ calcd for $C_{131}H_{216}N_7O_{18}S_2$, 2241.29; found, 2241.01.

Synthesis of Compound 39. Compound 39 was prepared by the reduction of azide 38 with $PPh_3$ (General procedure B), and was purified by column chromatography over silica gel using $CH_2Cl_2$/$CHCl_3$/MeOH (3:3:1) and then $CH_2Cl_2$/$CHCl_3$/MeOH/$Et_3N$ (5:5:3:0.2) as the eluents (70% yield). $^1$H NMR (400 MHz, $CDCl_3$/$CD_3OD$=1:1, δ): 4.38 (m, 2H), 3.92 (br, 5H), 3.79 (br, 5H), 3.63 (s, $CO_2CH_3$, 3H), 3.49 (br, 4H), 2.45 (t, J=7.5 Hz, 4H), 2.37-0.85 (series of m, 154H), 2.04 (d, 2 ⊘$SCH_3$, 6H), 0.66 (br, 15H). $^{13}$C NMR (100 MHz, $CDCl_3$/$CD_3OD$=1:1, δ): 175.58, 174.98, 174.92, 174.33, 170.96, 73.10, 68.37, 68.30, 68.21, 52.59, 51.72, 51.49, 49.96, 49.54, 47.04, 46.92, 46.56, 42.05, 41.90, 41.80, 39.57, 39.47, 36.34, 35.99, 35.79, 35.58, 34.92, 34.86, 34.67, 33.64, 33.34, 32.43, 32.15, 31.91, 31.31, 31.14, 30.40, 30.21, 28.24, 27.71, 27.44, 26.62, 26.55, 23.35, 22.72, 17.33, 17.26, 15.31, 12.55. MALDI-TOFMS (m/z): $[M+H]^+$ calcd for $C_{131}H_{218}N_7O_{18}S_2$, 2243.29; found, 2241.36. $[M+H]^+$ calcd for $C_{131}H_{217}N_7NaO_{18}S_2$, 2265.29; found, 2263.79. $[M+K]^+$ calcd for $C_{131}H_{217}N_7KO_{18}S_2$ 2281.29; found, 2279.86.

Synthesis of Compound 10. Compound 10 was obtained by coupling between hydrolyzed 8 and amine 39. (General procedures A and C), and was purified by column chromatography over silica gel using $CH_2Cl_2/CHCl_3/MeOH$ (50:50:12) as the eluents (89% yield). $^1$H NMR (400 MHz, $CDCl_3/CD_3OD$=1:1, δ): 8.48 (d, J=8.6 Hz, 1H), 8.27 (d, J=8.6 Hz, 1H), 8.18 (d, J=7.5 Hz, 1H), 7.54-7.43 (m, 3H), 7.34-7.18 (m, 4H), 7.15 (d, J=7.5 Hz, 1H), 4.38 (m, 2H), 4.01-3.89 (m, 6H), 3.85-3.74 (m, 6H), 3.71 (m, 1H), 3.63 (s, $CO_2CH_3$, 3H), 3.49 (br, 6H), 2.84 (s, $N(CH_3)_2$ 6H), 2.42 (m, 4H), 2.37-0.83 (series of m, 184H), 2.05 (d, 2×$SCH_3$, 6H), 0.79-0.58 (m, 18H). $^{13}$C NMR (100 MHz, $CDCl_3/CD_3OD$=1:1, δ): 175.56, 175.05, 174.99, 174.98, 174.39, 174.30, 173.68, 171.02, 151.82, 136.46, 130.10, 129.97, 129.82, 129.06, 128.04, 123.37, 119.47, 115.28, 73.09, 71.96, 70.49, 68.30, 68.21, 68.14, 57.72, 54.16, 52.73, 51.71, 50.06, 49.76, 49.62, 49.49, 47.17, 47.03, 46.84, 46.56, 45.51, 42.23, 42.01, 41.89, 41.81, 39.57, 39.48, 37.63, 36.84, 36.36, 35.99, 35.78, 35.56, 34.86, 34.69, 33.67, 33.35, 32.43, 31.91, 31.40, 31.31, 30.21, 28.24, 27.70, 27.46, 26.63, 26.46, 23.34, 22.71, 22.54, 17.95, 17.35, 17.28, 15.29, 12.55, 12.46. 12.55. MALDI-TOFMS (m/z): $[M+Na]^+$ calcd for $C_{167}H_{267}N_9NaO_{23}S_3$, 2888.15; found, 2889.08. $[M-H_2O+Na]^+$ calcd for $C_{167}H_{265}N_9NaO_{22}S_3$, 2870.15; found, 2872.93.

Synthesis of Compound 40. Compound 40 was prepared by the coupling between hydrolyzed compound 10 and 1-aminonaphthalene (General procedures A and C), and was purified by preparative TLC using $CHCl_3/MeOH$ (10:1) as the developing solvent (52% yield). $^1$H NMR (400 MHz, $CDCl_3/CD_3OD$=1:1, δ): 8.52 (d, J=8.4 Hz, 2H), 8.40 (d, J=8.8 Hz, 2H), 8.25 (d, J=6.4 Hz, 2H), 7.97 (d, J=8.0 Hz, 2H), 7.89 (m, 2H), 7.76 (d, J=8.0 Hz, 2H), 7.61-7.46 (m, 6H), 7.32 (d, J=7.6 Hz, 2H), 4.42-4.41 (m, 2H), 4.04-3.91 (m, 6H), 3.88-3.76 (m, 6H), 3.58-3.46 (m, 5H), 3.18 (br, 1H), 2.98 (s, $N(CH_3)_2$, 6H), 2.52-2.44 (m, 4H), 2.37-0.83 (series of m, 184H), 2.05 (d, 2×$SCH_3$, 6H), 0.79-0.64 (m, 18H). $^{13}$C NMR (100 MHz, $CDCl_3/CD_3OD$=1:1, δ): 178.6, 174.7, 174.0, 173.7, 171.1, 151.82, 129.5, 129.3, 129.2, 128.4, 127.4, 125.5, 125.3, 124.9, 122.76, 119.1, 119.0, 114.7, 77.4, 72.5, 67.6, 67.5, 65.9, 56.5, 55.1, 53.7, 52.1, 50.7, 46.5, 46.3, 44.8, 44.7, 41.8, 41.6, 41.3, 39.1, 39.0, 38.9, 38.2, 37.0, 35.7, 35.5, 35.2, 34.4, 34.3, 34.1, 33.0, 32.7, 31.7, 31.5, 30.6, 29.9, 29.6, 29.2, 27.8, 27.2, 26.9, 26.1, 26.0, 22.7, 22.0, 21.8, 20.5, 18.9, 16.6, 16.5, 15.7, 14.4, 12.8, 11.8, 11.7, 11.4. MALDI-TOFMS (m/z): [M+Na] calcd for $C_{176}H_{272}N_{10}NaO_{22}S_3$, 2999.29; found, 2999.58.

Fluorescence Quenching of Compound 1. Typical procedures for the quenching experiment are as follows. A stock solution ($2.0 \times 11^{-4}$ M) of compound 10 in anhydrous THF was prepared. For the fluorescence titrations, an aliquot (20.0 μL) of the stock solution was added to 2.00 mL of the given solvent mixture in a quartz cuvet. Fresh stock solutions ($2.0 \times 10^{-3}$ M) of $Hg(OAc)_2$ in MeOH were prepared and used in the same day for all the titrations. Aliquots of $Hg(OAc)_2$ stock solutions were added with a Hamilton Gastight syringe. After each addition, the sample was vortexed for 1 minute before the fluorescence spectrum was recorded. The excitation wavelength was set at 336 nm and the average emission intensity from 457 nm to 557 nm was used to determine the association constant $K_a$.

Job plot for binding between compound 10 and $Hg^{++}$: Stock solutions ($2.0 \times 10^{-4}$ M) of foldamer 10 in THF and $Hg(OAc)_2$ in methanol were prepared. Portions of the two solutions were added to 2.00 mL of 5% MeOH in ethyl acetate/hexane (2/1 v/v) in a quartz cuvet such that their ratios changed from 0 to 1 while maintaining a total concentration of 10 and $Hg^{++}$ of 2.0 μM. The excitation wavelength was set at 336 nm and the emission intensity at 502 nm was monitored. Maximum at 0.5 molar fraction indicated a 1:1 binding stoichiometry.

Results

Natural amino acids were incorporated into cholate foldamers to provide reactive groups that could bind the metal ions upon foldamer folding. Because the present foldamers are oligoamides, the amino acids were easily incorporated into the foldamer sequence using standard peptide synthesis procedures. Moreover, the presence of amino acids on the foldamers of the invention did not perturb their folding properties—likely because nonspecific, solvophobic interactions have high tolerance for structural perturbation. See, Schneider & Yatsimirsky, A. *Principles and Methods in Supramolecular Chemistry*; Wiley: Chichester, 2000; pp 102-110, and references therein.

To equip the cholate foldamer with mercury-binding ligands, two L-methionine residues were inserted into the foldamer primary structure to generate a hybrid foldamer (10) that also included a dansyl moiety as a fluorescent dye.

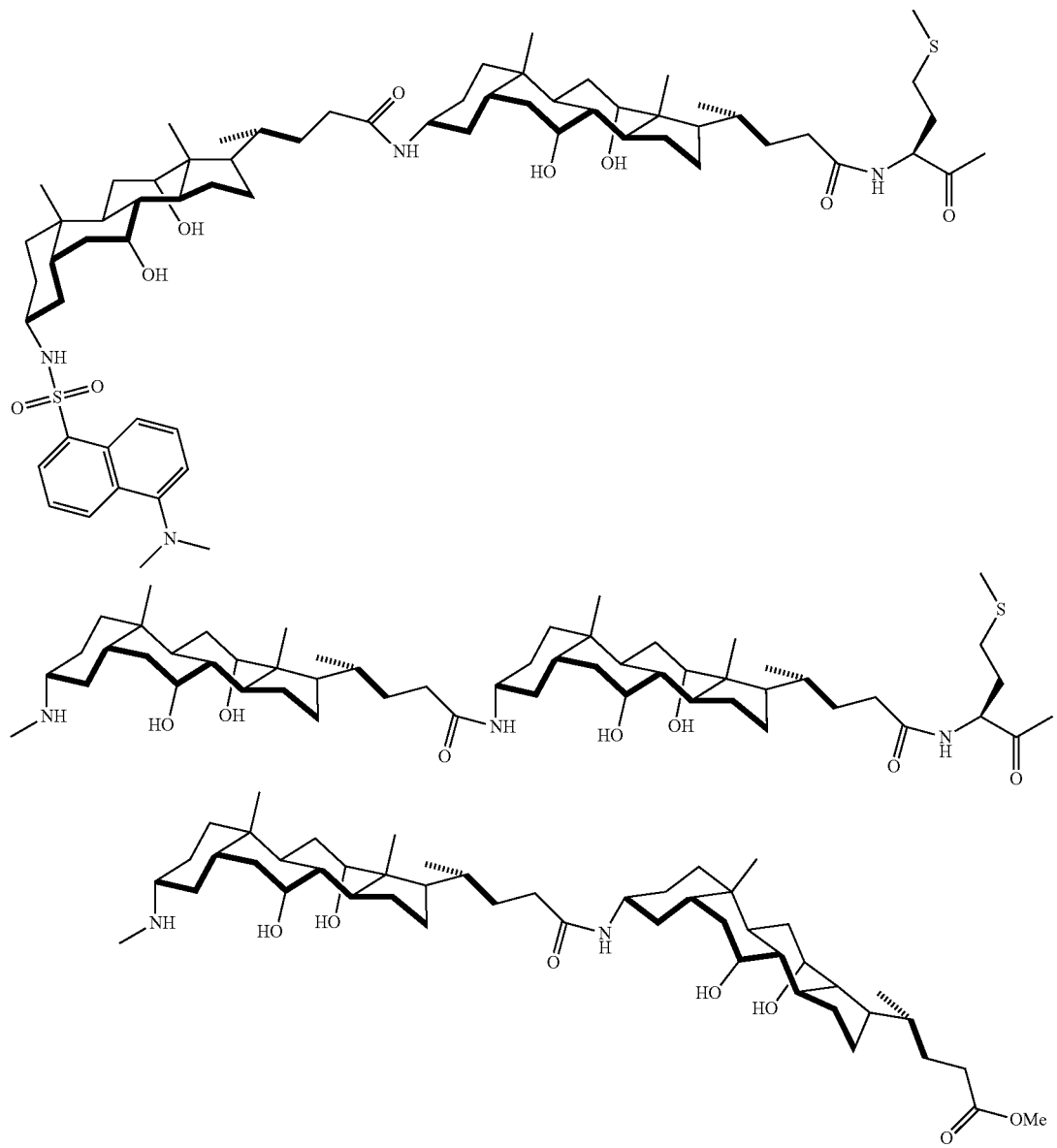

Dansyl was selected as a reporter moiety because it is strongly fluorescent and easily linked to the amino terminus of the foldamer.

The folded oligocholates resembled a unimolecular reversed micelle with a hydrophobic exterior and hydrophilic interior. Therefore, the most "folding-friendly" solvents were nonpolar ones with a small amount of polar solvent such as methanol or methyl sulfoxide (Ryu, E.-H.; Zhao, Y. Org. Lett. 2004, 6, 3187-3189). The effect of $Hg^{2+}$ on the fluorescence of foldamer 10 was first studied in such a solvent mixture-5% methanol in hexane/ethyl acetate (2/1).

Figure 15A:
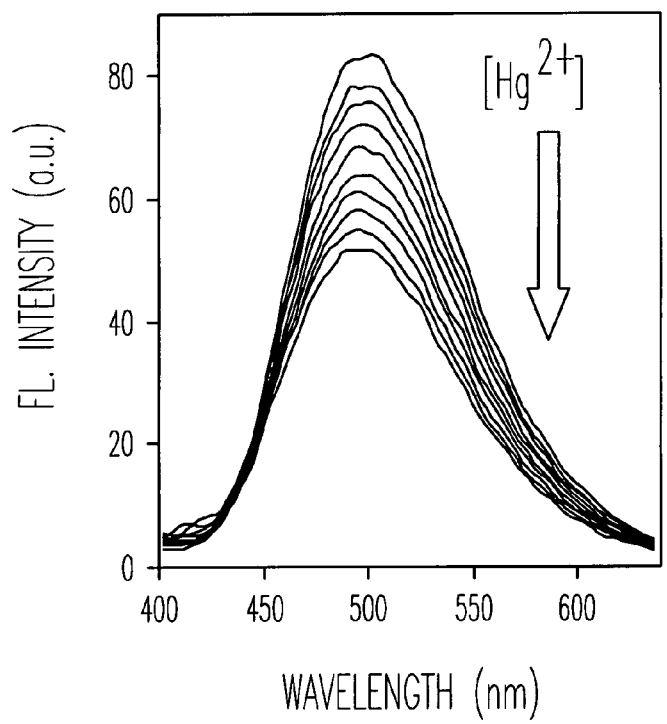
FIG. 15A shows fluorescence spectra of foldamer 10 in the presence of different concentrations of mercury ions, where the [Hg$^{2+}$] for the different spectra varied from 0, 0.02, 0.04, 0.08, 0.12, 0.16, 0.2, 0.26, 0.32, and 0.4 µM from top to bottom, using as solvent 5% MeOH in hexane/ethyl acetate (2/1). The concentration of foldamer 10 was held constant at 0.2 µM.

As shown in FIG. 15A, the fluorescence of foldamer 10 was extremely sensitive to mercury ions—20 nM of $[Hg^{2+}]$ could be easily detected not only by a change in fluorescence intensity but also because the emission band of the mercury-containing foldamer blue-shifted by about 10 nm. The results are consistent with an electron-transfer quenching mechanism found also in other Dansyl-based mercury sensors (Metivier, R.; Leray, I.; Valeur, B. Chem. Eur. J. 2004, 10, 4480-4490).

Figure 15B:
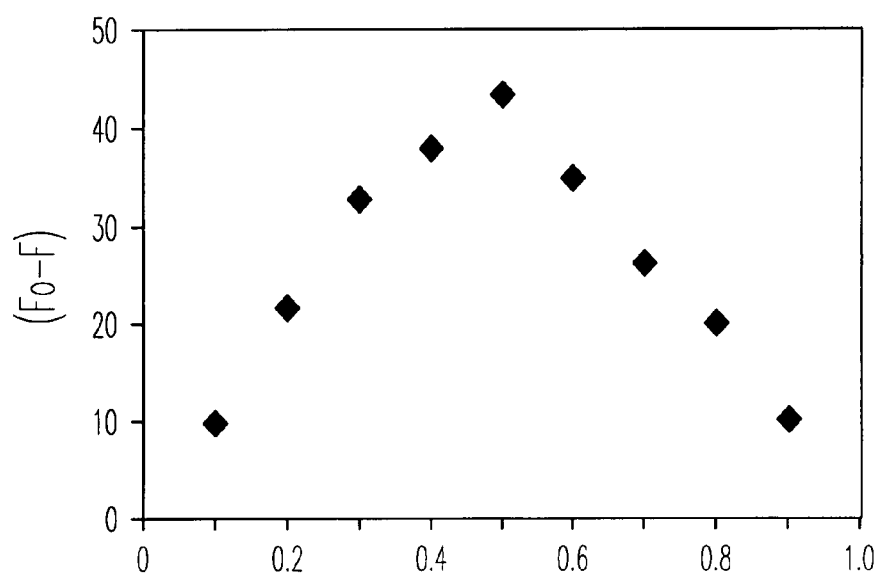
FIG. 15B is a Job plot illustrating the binding between foldamer 10 and Hg$^{++}$, in which χ is the molar fraction of foldamer 10. The concentrations of foldamer 10 and Hg$^{++}$ were adjusted so that [10]+[Hg$^{++}$]=2.0 µM in 5% MeOH: ethyl acetate/hexane (2/1 v/v).

The binding stoichiometry of foldamer 10 for mercury was 1:1 as confirmed by a Job plot (FIG. 15B). Nonlinear least-squares fitting gave an association constant ($K_a$) of $1.5 \times 10^7$ $M^{-1}$, which translates to a binding free energy of $-\Delta G=9.8$ kcal/mol.

As shown in Example 1, dimethyl sulfoxide (DMSO) was found to be better at promoting folding of the cholate foldamers than methanol. When 5% DMSO was used in place of methanol in the above mixture, however, a very similar affinity ($K_a=1.2 \times 10^7$ $M^{-1}$) was obtained.

Similar mercury titrations were then performed in a number of solvent mixtures and the results are summarized in Table 3.

TABLE 3

Thermodynamic data for binding between 10 and $Hg^{2+}$, at 25° C. as determined by fluorescence titration.

| Entry | Solvent Composition[a] | $K_a$ $(M^{-1})$[b] | $-\Delta G$ (kcal/mol) |
|---|---|---|---|
| 1 | 5% MeOH in HX/EA (2/1) | $(1.5 \pm 0.3) \times 10^7$ | 9.8 |
| 2 | 5% DMSO in HX/EA (2/1) | $(1.2 \pm 0.4) \times 10^7$ | 9.7 |
| 3 | 5% MeOH in EA | $(7.3 \pm 1.7) \times 10^6$ | 9.4 |
| 4 | 10% MeOH in EA | $(3.8 \pm 0.8) \times 10^6$ | 9.0 |
| 5 | 20% MeOH in EA | $(1.6 \pm 0.2) \times 10^6$ | 8.5 |
| 6 | 40% MeOH in EA | $(1.1 \pm 0.1) \times 10^6$ | 8.2 |
| 7 | 60% MeOH in EA | $(7.6 \pm 0.4) \times 10^5$ | 8.0 |
| 8 | 80% MeOH in EA | $(3.9 \pm 0.6) \times 10^5$ | 7.6 |
| 9 | 100% MeOH | $(2.6 \pm 0.2) \times 10^5$ | 7.4 |
| 10 | 5% $H_2O$ in THF | $(2.4 \pm 0.1) \times 10^4$ | 6.0 |
| 11 | 10% $H_2O$ in THF | $(1.9 \pm 0.2) \times 10^4$ | 5.9 |

[a]HX = hexane; EA = ethyl acetate.
[b]The association constants were determined by nonlinear least-squares fitting to a 1:1 binding isotherm.

If binding affinities did not change much in folding-friendly solvents, they could be tuned over broad ranges in folding-unfriendly ones. Table 3 summarizes binding data determined by fluorescence titrations. Several trends are immediately noticeable.

First, when hexane is removed from the ternary solvents (entries 1 & 3), $-\Delta G$ decreases by 0.4 kcal/mol. Weaker binding is consistent with earlier finding that folding is promoted by limited miscibility of solvents. The folded oligocholate resembles a unimolecular reversed micelle. The most "folding-friendly" solvents are nonpolar ones mixed with a small amount of a polar solvent. Since the interior of a folded conformer prefers polar molecules, microphase separation of solvents happens during folding. MeOH is completely miscible with EA but barely miscible with hexane. Therefore, demixing should be easier in MeOH/hexane/EA than in MeOH/EA.

Figure 15C:
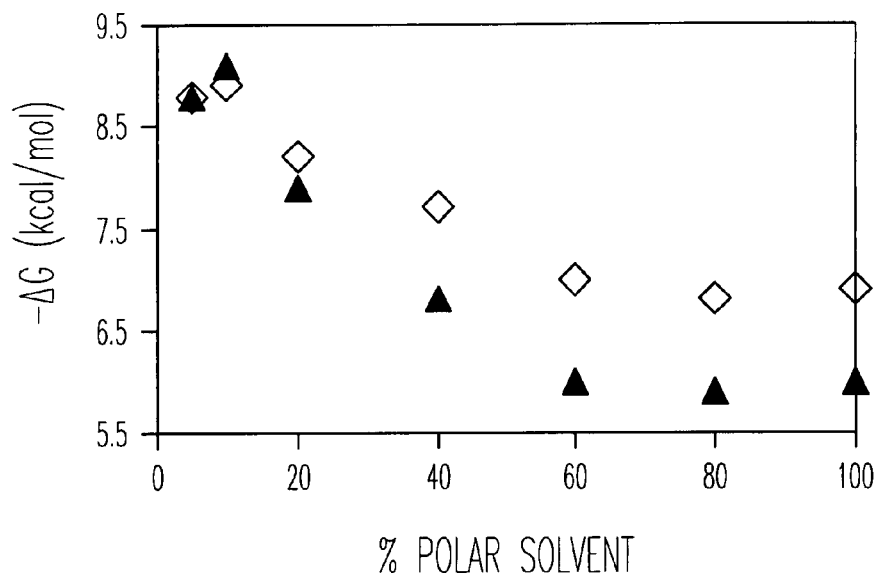
FIG. 15C shows a graph of the binding free energy of foldamer 10 with mercury as a function of volume percentages of methanol (◊) and DMSO (▲) in ethyl acetate.

Second, in the binary mixture of methanol and ethyl acetate (EA), $-\Delta G$ decreases further by 2 kcal/mol (entries 3-9) as methanol content increases from 5 to 100% (FIG. 15C). Each cholate is about 1.4 nm from head to tail. Separated by two cholate units, the sulfur groups probably cannot chelate mercury in the unfolded state. If the assumption is correct, the data can be easily explained because the folded, mercury-binding conformer has a hydrophobic exterior and is disfavored by highly polar solvents.

Third, $K_a$ in water/THF is several orders of magnitude lower than those in the folding-friendly solvents (compare entries 10-12 with 1), and even weaker ($K_a$ less than 100 $M^{-1}$) in some other mixtures such as water/butanol or water/2-methoxyethanol. Since water, THF, and butanol have very similar $D_s$ values (Lewis basicity toward $HgBr_2$, 14 for ethyl acetate, 17 for water and THF, 18 for methanol and butanol, and 28 for DMSO; see: Sandström, M; Persson, I.; Persson, P. Acta Chem. Scand. 1990, 44, 653-675; and Chen, T.; Hefter, G.; Marcus, Y. J. Sol. Chem. 2000, 29, 201-216), variation in binding cannot be caused by different Lewis basicity, but, instead, most likely by poor folding in these mixtures. The conclusion is in agreement with previous observation that the parent oligocholates remain unfolded in water/THF even when nonpolar solvents such as 2-methyl-THF (MTHF) was added to facilitate demixing of water.

Figure 15D:
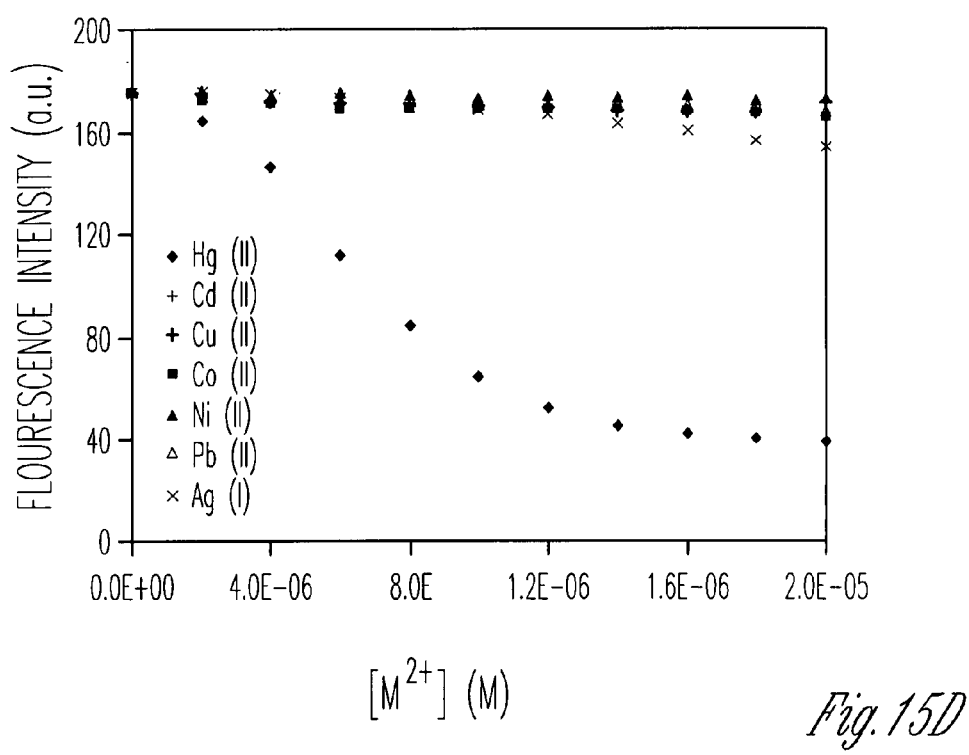
FIG. 15D is a graph of the fluorescence intensity of foldamer 10 as a function of metal ion concentration [M$^{++}$] in methanol.

Finally, foldamer 10 is highly selective as a mercury sensor. Under similar conditions, other commonly interfering divalent cations such as $Mg^{2+}$, $Zn^{2+}$, $Cu^{2+}$, $Co^{2+}$, $Ni^{2+}$, and even $Pb^{2+}$ showed almost no response (FIG. 15D). The only cation that showed slight (4%) response was $Ag^+$. The observed specificity is surprising for a foldamer with considerable flexibility in the structure. It is possible that specificity comes from both selectivity in binding and in quenching—$Hg^{2+}$ is known to quench the fluorescence of Dansyl much more efficiently than many other metal ions (Metivier, R.; Leray, I.; Valeur, B. Chem. Eur. J. 2004, 10, 4480-4490.).

Solvent Effects in the Mercury-Binding Foldamers

Foldamer 10 was found to bind $Hg^{2+}$ particularly weakly in water/THF mixtures, suggesting poor folding in this mixture. This observation, together with the unexpected, poor folding of the oligocholates in water/THF/MTHF, suggested that there was something special about aqueous THF. To understand the role played by each solvent in aqueous THF, the THF was replaced with propanol and the binding constant ($K_a$) between foldamer 10 and $Hg^{2+}$ was measured in several water/propanol mixtures. THF and propanol differ in at least two important aspects. First, water is completely miscible with propanol but only partially miscible with THF. Second, propanol, similar to water, can participate as both a donor and an acceptor in hydrogen-bonding, whereas THF can only act as an acceptor. Therefore, if any of these properties are important to the folding of the oligocholates, they should be reflected in the binding data. As shown in Table 4, however, binding of $Hg^{2+}$ is nearly identical in both series (entries 1-6 vs. 7-12). The binding free energy ($-\Delta G$) not only starts at a similar value but follows a similar trend, a gradual decrease with increasing water percentages.

TABLE 4

Binding Constants ($K_a$) for foldamer 10 and $Hg(OAc)_2$ at 25° C. in aqueous solutions.

| Entry | Solvent Composition | $K_a$ $(M^{-1})$[b] | $-\Delta G$ (kcal/mol) |
|---|---|---|---|
| 1 | 5% $H_2O$ in THF | $(2.4 \pm 0.1) \times 10^4$ | 6.0 |
| 2 | 10% $H_2O$ in THF | $(1.9 \pm 0.2) \times 10^4$ | 5.9 |
| 3 | 20% $H_2O$ in THF | $(5.5 \pm 0.6) \times 10^3$ | 5.1 |
| 4 | 30% $H_2O$ in THF | $(4.0 \pm 0.3) \times 10^3$ | 4.9 |
| 5 | 40% $H_2O$ in THF | $(2.6 \pm 0.1) \times 10^3$ | 4.7 |
| 6 | 50% $H_2O$ in THF | $(1.3 \pm 0.1) \times 10^3$ | 4.3 |
| 7 | 5% $H_2O$ in PrOH | $(3.4 \pm 0.4) \times 10^4$ | 6.2 |
| 8 | 10% $H_2O$ in PrOH | $(1.5 \pm 0.2) \times 10^4$ | 5.9 |
| 9 | 20% $H_2O$ in PrOH | $(1.0 \pm 0.1) \times 10^4$ | 5.5 |
| 10 | 30% $H_2O$ in PrOH | $(3.2 \pm 0.2) \times 10^3$ | 4.8 |
| 11 | 40% $H_2O$ in PrOH | $(2.8 \pm 0.2) \times 10^3$ | 4.7 |
| 12 | 50% $H_2O$ in PrOH | $(2.4 \pm 0.1) \times 10^3$ | 4.6 |

[a]The association constants were determined by nonlinear least-squares fitting to a 1:1 binding isotherm. The stoichiometry of binding was previously confirmed to be 1:1 by the job plot.

Therefore, the culprit for the poor folding is not THF but water. Water is certainly a unique solvent, and experiments were performed to ascertain which property (or properties) of water make it difficult for the oligocholate to fold. To understand this better, mercury binding was studied in a series of alcohols, both in the neat form and as a mixture with 10 vol % water. The advantage of using an alcohol instead of THF as the co-solvent is that its size, hydrophobicity, and miscibility may be systematically tuned by its alkyl group. As the alkyl group increases, the size and hydrophobicity of the alcohol increase but the miscibility with water decreases.

Figure 15E:
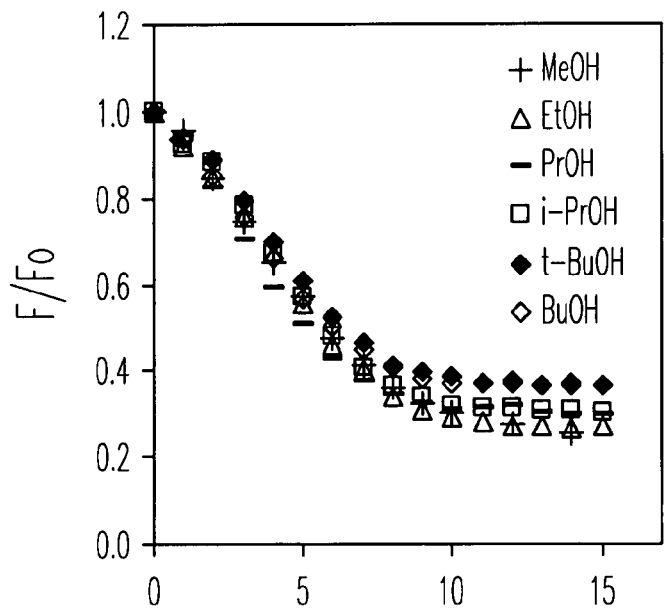
FIG. 15E illustrates the normalized maximum emission intensity of the Dansyl group of foldamer 10 as a function of Hg$^{++}$ concentration [Hg$^{++}$] in different alcohols, where the concentration of foldamer 10 [10] was 2.0 µM.
Figure 15F:
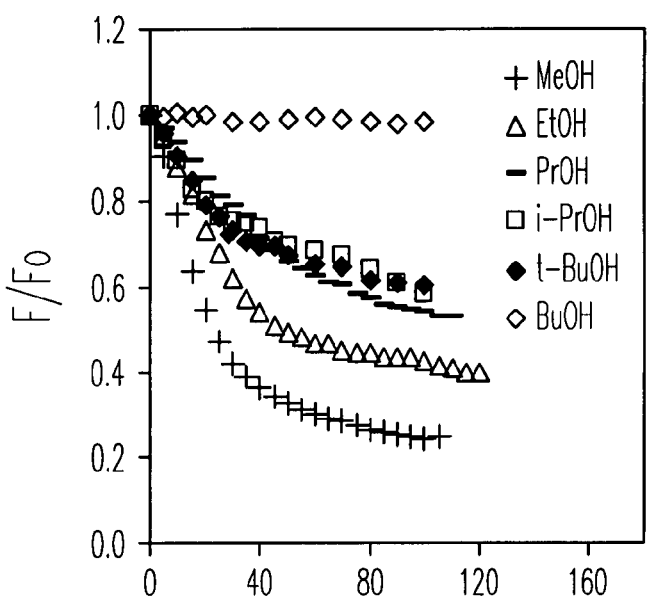
FIG. 15F shows the normalized maximum emission intensity of the Dansyl group of foldamer 10 in 10% water in different alcohols as a function of mercury ion concentration [Hg$^{2+}$], where the concentration of foldamer 10 [10] was 2.0 µM.

FIG. 15E shows the normalized titration curves for the binding of 10 in neat alcohols. Clearly, mercury binding (and thus folding of the oligocholate chain) is independent of the alcohol when there is only one solvent present. Binding in the 10% aqueous mixtures, on the other hand, is highly sensitive to the nature of the alcohol (FIG. 15F). Two trends are immediately noticeable by comparing the two solvent series. First, binding is weaker in aqueous mixtures than in neat alcohols. Note that the range of [$Hg^{2+}$] was about 120 μM in experiments providing data for FIG. 15F but only 15 μM in experiments providing data for FIG. 15E. Second, binding/folding clearly depends on the size or hydrophobicity of the alcohol in the aqueous mixture. Whereas binding in aqueous methanol (+) is reasonably strong, it cannot even be detected in aqueous butanol (◊). FIG. 15F shows that binding/folding is strongest in methanol and fall off as follows: methanol>ethanol>propanol≈isopropanol≈t-butanol>butanol in the corresponding aqueous mixture. These trends are also reflected in $K_a$ obtained from the titration curves (Table 5). Whereas $K_a$ ($=2-3\times10^5$ M$^{-1}$) remains nearly constant in neat alcohols, it decreases from $5.4\times10^4$ M$^{-1}$ in 10% water/methanol (entry 7) to <300 M$^{-1}$ in 10% water/butanol (entry 12). Aqueous butanol, however, is not a unique mixture because the binding in 10% water in 2-methoxylethanol (entry 13) is equally weak (if not weaker).

TABLE 5

Binding Constants ($K_a$) for foldamer 10 and Hg(OAc)$_2$ at 25° C. in pure and mixed alcohols.

| Entry | Solvent Composition | $K_a$ (M$^{-1}$)$^a$ | $-\Delta G$ (kcal/mol) |
|---|---|---|---|
| 1 | MeOH | (2.6 ± 0.2) × 10$^5$ | 7.4 |
| 2 | EtOH | (2.7 ± 0.3) × 10$^5$ | 7.4 |
| 3 | PrOH | (2.5 ± 0.2) × 10$^5$ | 7.4 |
| 4 | i-PrOH | (2.3 ± 0.2) × 10$^5$ | 7.3 |
| 5 | t-BuOH | (1.9 ± 0.2) × 10$^5$ | 7.2 |
| 6 | BuOH | (2.6 ± 0.2) × 10$^5$ | 7.4 |
| 7 | 10% H$_2$O/MeOH | (5.4 ± 0.6) × 10$^4$ | 6.5 |
| 8 | 10% H$_2$O/EtOH | (3.7 ± 0.5) × 10$^4$ | 6.2 |
| 9 | 10% H$_2$O/PrOH | (1.5 ± 0.2) × 10$^4$ | 5.7 |
| 10 | 10% H$_2$O/i-PrOH | (1.8 ± 0.2) × 10$^4$ | 5.8 |
| 11 | 10% H$_2$O/t-BuOH | (1.5 ± 0.1) × 10$^4$ | 5.7 |
| 12 | 10% H$_2$O/BuOH | <300$^b$ | — |
| 13 | 10% H$_2$O/MeOCH$_2$CH$_2$OH | <100$^b$ | — |
| 14 | 10% MeOH/BuOH | (1.3 ± 0.2) × 10$^5$ | 7.0 |
| 15 | 10% EtOH/BuOH | (1.8 ± 0.5) × 10$^5$ | 7.2 |
| 16 | 10% PrOH/BuOH | (2.3 ± 0.7) × 10$^5$ | 7.3 |

$^a$The association constants were determined by nonlinear least-squares fitting to a 1:1 binding isotherm.
$^b$Binding was too weak to be measured by fluorescence titration. $K_a$ was estimated from the titration curves.

Figure 14A:
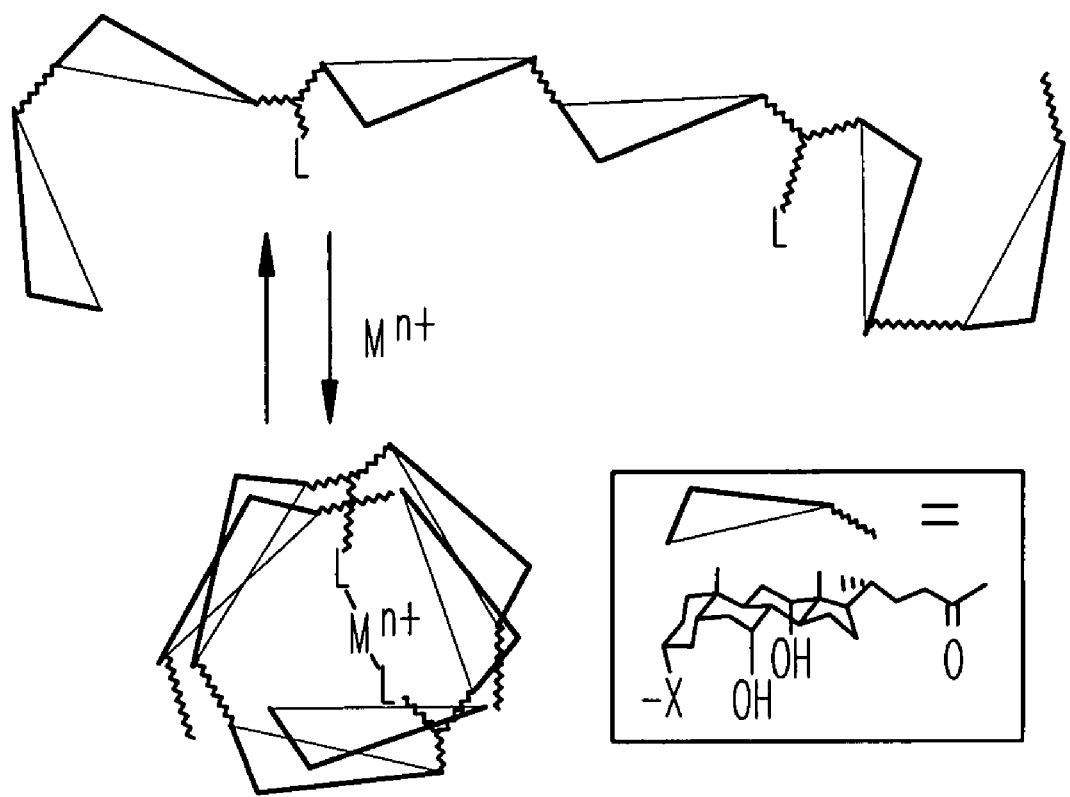
FIG. 14A is a schematic representation of a metal ion-binding foldamer with the metal ion assisting the folding.
Figure 14B:
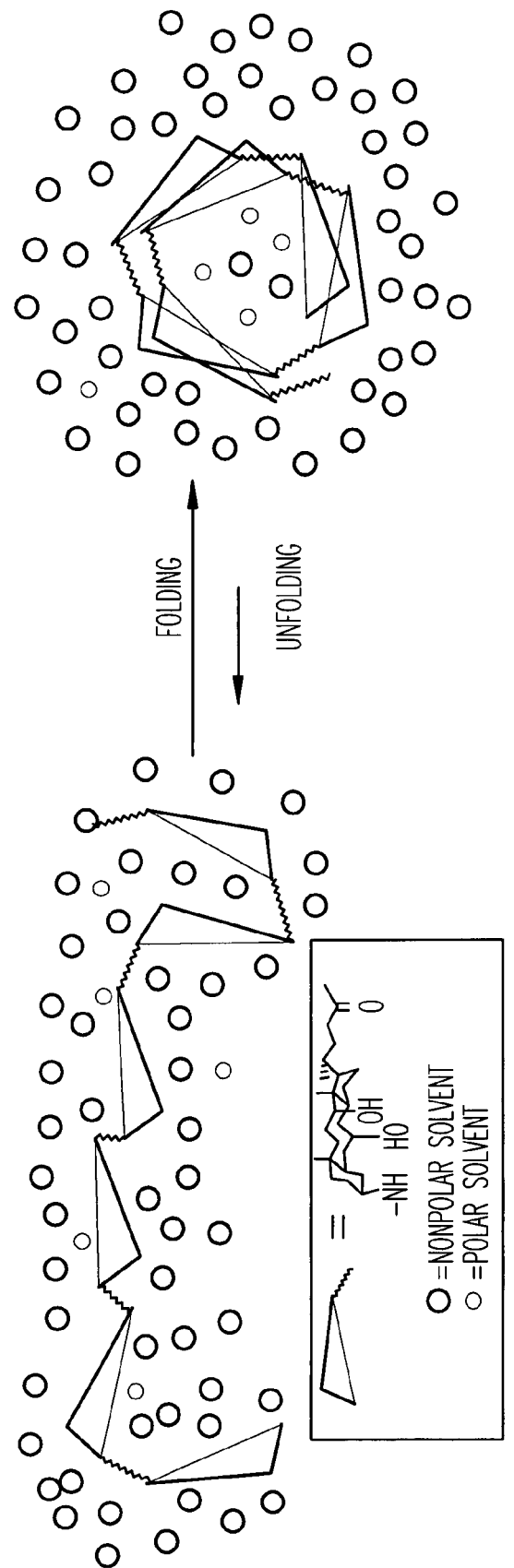
FIG. 14B is schematic representation of how a foldamer folds in solvent mixture containing both polar (small circles) and nonpolar (large circles) solvents. This solvent system is represented as a "folding-friendly" solvent mixture containing five polar solvent molecules and fifty nonpolar ones. The cholate foldamer is depicted as triangles with two blue (nonpolar) sides and one red (polar) side. By forming the structure on the right, not only the polar solvent molecules (at least some of them) are relocated from a nonpolar medium, a less preferred environment, to a more preferred polar microenvironment, but the oligocholate itself is able to minimize unfavorable exposure of its hydrophilic faces to the nonpolar solvent.

Foldamer 10 by itself obviously cannot fold in neat alcohol, as no solvophobic driving force depicted in FIG. 14B. The only reason for its folding is the strong Hg—S complexation. Therefore, the observed binding energy for 10-Hg$^{2+}$ in a given solvent can be viewed roughly as the binding energy for a hypothetical, perfectly folded 10 minus the energy needed to fold 10 in the same solvent. This treatment assumes other factors such as the change in solvent composition has a negligible effect on the Hg—S interaction. It is reasonable because the $D_s$ value (indicating the Lewis basicity toward soft metal ions measured with HgBr$_2$) of water, THF, and the alcohols are very similar (Sandström et al., *Acta Chem. Scand.* 1990, 44, 653-675; Chen et al., *J. Sol. Chem.* 2000, 29, 201-216).

When only one solvent is present, both the hydrophilic and hydrophobic faces of the oligocholates are exposed to the same solvent, regardless of the folded state. As long as the internal cavity of the folded conformer is sufficiently large to be easily accessed by the solvent, the solvent can solvate the folded state to the same extent as it does to the unfolded state. Different alcohols do differently solvate the foldamer. However, as long as they solvate the mercury-free (unfolded) and mercury-bound (folded) host similarly, the difference in solvation cancels out when the mercury binding is considered. This is probably the reason for the insensitivity of binding/folding toward the alcohol when neat alcohol is used. Note also that the size of all the alcohols studied is quite small compared to the nanometer-sized hydrophilic cavity.

In aqueous alcohol, water is the more hydrophilic component. It is reasonable to assume that water is preferred over the alcohol by the hydrophilic (i.e., water-loving) nanocavity formed during folding, especially if the alcohol is fairly hydrophobic. In other words, folding, made possible by mercury complexation, will force microphase separation of water from alcohol when both solvents are present. This phase separation, however, costs energy and certainly will not happen spontaneously in the absence of the cholate foldamer. Therefore, the energy paid to phase-separate water from the bulk into the interior of the foldamer is a necessary cost for the folding. Other costs, such as those associated with the loss of conformational entropy during formation of an ordered, compact structure, do exist, but may be more of the property of the foldamer chain itself and may not depend as much on the solvent composition as the phase separation. This is probably why binding is weaker in the aqueous mixture than in the neat alcohol, as no such penalty will occur during folding when there is only one solvent present.

As indicated, the type of alcohol used in the aqueous mixtures affects the binding reaction. The preference for water over alcohol—where it is assumed that water is preferred by the hydrophilic cavity—is small in aqueous methanol, as both solvents are polar and can effectively solvate the hydrophilic wall of the cavity. As a result, minimal microphase separation is needed and the penalty for folding is small. Hence, $-\Delta G$ for 10-Hg$^{2+}$ only decreases by 0.9 kcal/mol going from pure methanol to 10% water/methanol (Table 5, entries 1 and 7).

In aqueous butanol, the situation is different. As a result of the higher hydrophobicity of butanol, the preference for water over alcohol by the hydrophilic nanocavity is much higher. Even though phase separation of water from butanol is easier than from methanol, a larger extent of phase separation is involved in the folding in aqueous butanol as a result of this higher selectivity, meaning that more water molecules need to be phase separated from the bulk to the nanocavity during folding.

There may also be a size effect. When a large alcohol is disfavored or "rejected" by the cavity, more water molecules need to come in to take its place. This effect is particularly significant because water is the smallest of common solvents. Even if the selectivity (the preference for water over alcohol caused by different hydrophilicity/hydrophobicity of the solvent) is the same, a larger alcohol still requires a larger extent of phase separation. Therefore, an increase in size for the alcohol or, more accurately, an increase in the size difference between the more polar and the less polar solvents always translates to a higher cost for the folding.

Unfortunately, the size and the hydrophobicity of the alcohol cannot be varied independently. It is interesting to compare the binding/folding of 10 in 2-methoxyethanol vs. butanol. 2-Methoxyethanol is comparable in size and more hydrophilic than butanol. Yet, the binding of 10 is similar in both aqueous mixtures (Table 5, entries 12 and 13). Therefore, at least for these two mixtures, the size effect seems to dominate.

For the branched alcohols, mercury-binding by foldamer 10 is essentially the same in aqueous propanol, isopropanol, and t-butanol (Table 5, entries 9-11, also FIG. 15F). Similar behavior in the cases of propanol and isopropanol is not surprising, given the similarity in their structures and properties, such as solubility in water. The behavior of t-butanol is quite strange but, one has to remember, among all the (isomeric) butanols, it is the only one that is completely miscible with water (Marcus, Y. *The Properties of Solvents*; Wiley:

New York, 1999; p 176). This unusual miscibility at least is directionally consistent with the folding model. Better miscibility of t-butanol suggests a lower selectivity for water by the hydrophilic nanocavity, which is equivalent to a smaller extent of phase separation during folding. Of course, this effect is counterbalanced by the higher energetic cost (per water molecule) to separate water from t-butanol than from butanol. With two opposing effects present, one cannot predict a priori which solvent mixture if better for the folding of 10. The data suggest that the extent of phase separation plays the dominant role in the t-butanol/butanol comparison. Other factors may be also important here but are unclear to us at the moment. For example, if better miscibility is the only reason for the better folding in aqueous t-butanol than in aqueous butanol, good folding should also be expected for aqueous 2-methoxyethanol but was clearly not the case (Table 5, entry 13).

Therefore, the system is rather complex, partly because multiple solvent effects are involved and some of them are opposing one another, maybe partly because folding is inferred from the binding data—a reasonable but approximate treatment. At this point, the extent of phase separation seems to be the controlling factor, e.g., in water/methanol and water/butanol case. This conclusion should not be generalized, however. It is certainly conceivable that miscibility can play a more important role in other mixtures. For example, the partly miscible DMSO/(hexane/EA=2/1) mixture was better for the folding than the completely miscible DMSO/(hexane/EA=1/1).

The above information also applies to non-aqueous mixtures. Indeed, when butanol is used as the larger solvent and methanol, ethanol, or propanol as the smaller solvent, a similar, albeit weaker, effect is observed (Table 5, compare entries 14-16 with entries 6 and 12). The weaker effect is anticipated because the size difference between methanol/ethanol/propanol and butanol is smaller than that between water and butanol. In addition, because water is far more hydrophilic than any of the alcohols, the selectivity for the smaller alcohol over butanol by the nanocavity is lower than that for water over butanol. Lower selectivity also means that the observed effect resulted from microphase separation of solvents will be weaker in the mixed alcohol series.

Solvent Effects in A Foldamer Stabilized by Internal Salt Bridge. The folding of 10 occurs upon binding metal (e.g., mercury) ions. The strong Hg—S complexation may permit folding to be studied in solvents that may not be used for accessing folding of the parent oligocholates. Studying folding in water-containing solvents was not possible with the parent oligocholates because they can only fold in the most folding-friendly solvent mixtures (e.g., 1-5% DMSO in hexane/EA=2/1). To further explore the folding reaction independent of Hg—S interactions, foldamers containing a salt bridge, as in 102, which has an arginine and a glutamate in the sequence.

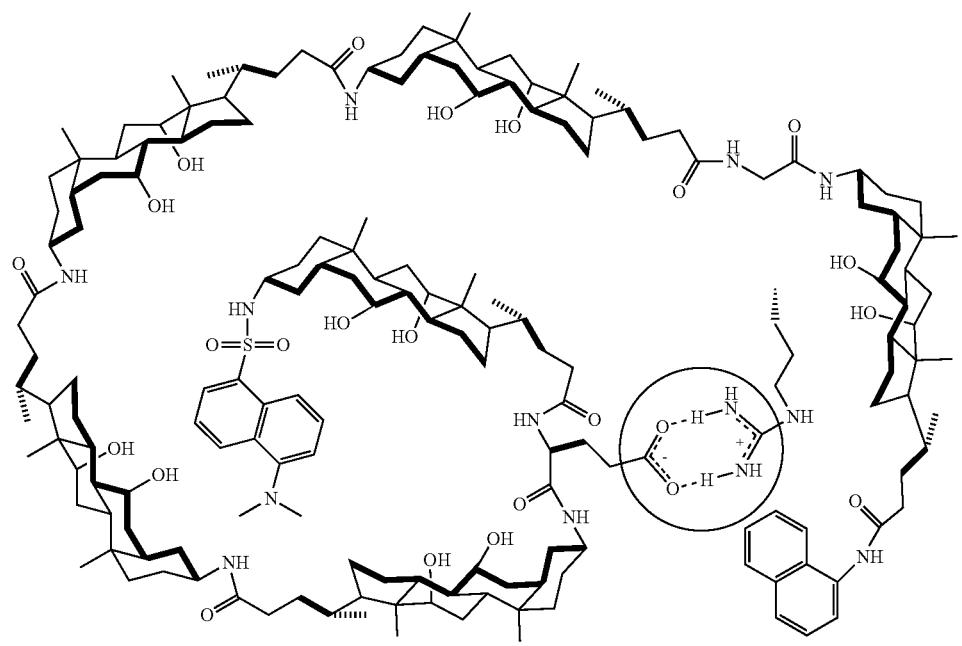

102

Studying folding in water-containing solvents is not possible with the parent oligocholates because they can only fold in the most folding-friendly solvent mixtures (e.g., 1-5% DMSO in hexane/EA=2/1). One strategy to stabilize the folded state is through incorporation of a salt bridge, as in 102, which has an arginine and a glutamate in the sequence. As described herein, when the folding of 10 was studied in the absence of $Hg^{2+}$, insertion of the amino acids was found to enhance the folding slightly. Such amino acid insertion may introduce flexibility to the chain. Foldamer 102 was synthesized via procedures like those described herein and labeled with the naphthyl-Dansyl, the same FRET donor-acceptor pair used to characterize the parent oligocholates (e.g. 6).

Figure 15G:
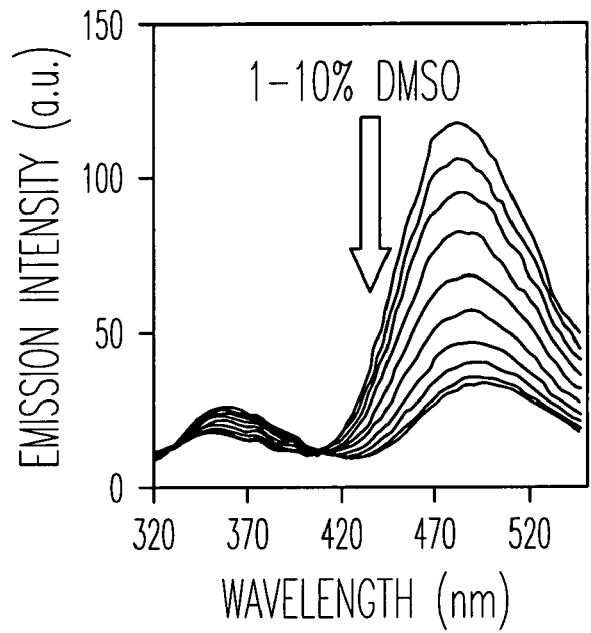
FIG. 15G shows fluorescence spectra of foldamers 102 in EA with different percentage of DMSO. The concentration of foldamer [102] was 2.0 µM.
Figure 15H:
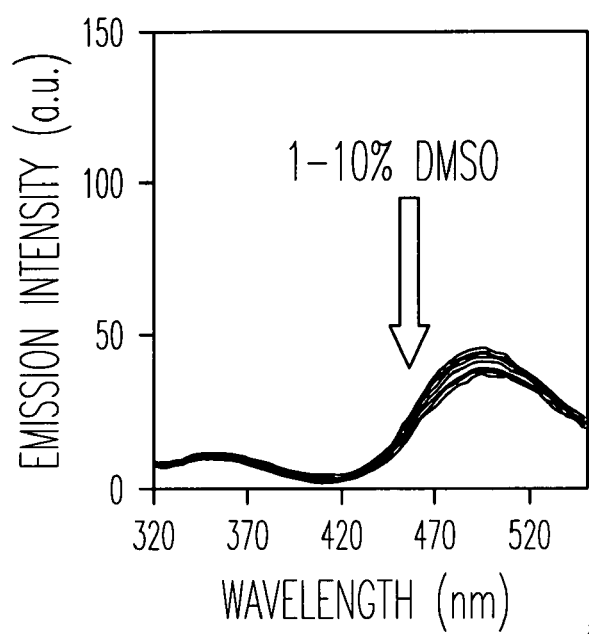
FIG. 15H shows fluorescence spectra of foldamer 6 in EA with different percentage of DMSO. The concentration of foldamer [6] was 2.0

The salt bridge is beneficial to the folding. When the naphthyl donor of 102 is excited in 1% DMSO/EA, the donor emission near 350 nm is weak but the acceptor emission from the Dansyl near 490 nm is extremely strong (FIG. 15G), indicating efficient FRET. With more DMSO added, the donor emission becomes stronger while the acceptor emission gets weaker. The change corresponds to a transition from a folded, more compact structure to an unfolded, less compact structure. Over 1-10% DMSO, the parent foldamer 6, on the other hand, shows a weak emission band for the acceptor and remains nearly constant, indicating a mostly unfolded structure throughout the solvent titration (FIG. 15H).

Folding was indeed observed using this solvent mixture (data not shown). In these solvent-titration experiments, the acceptor emission as a function of the solvent composition can be used to judge the folding ability of the foldamers. Provided the conformational change follows a two-state tran-

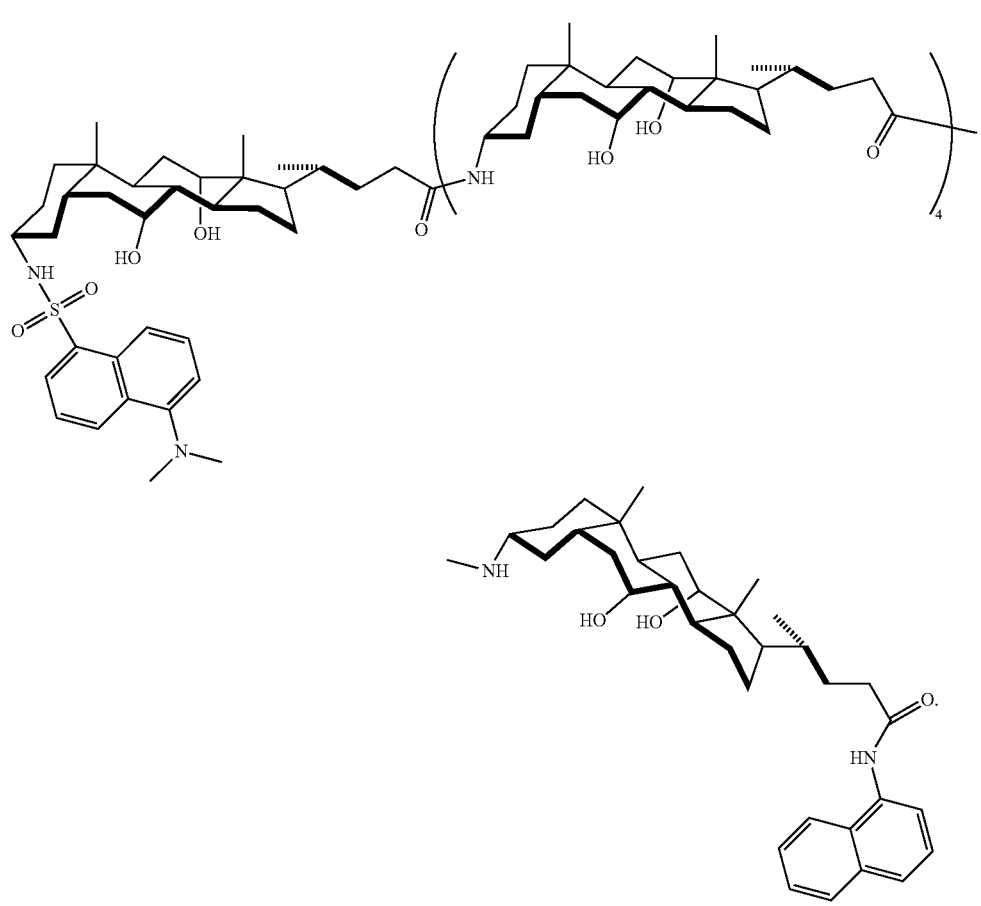

6

The fluorescence resonance energy transfer (FRET) of 102 was then studies in THF/MTHF (1/2) with 1-8% water. This ratio of THF/MTHF was chosen to minimize the energetic cost to phase separate water. Surprisingly, the salt bridge did not help binding at all and FRET is completely absent in both foldamers 102 and 6 (data not shown). Apparently, the penalty for folding is so large in H₂O/THF/MTHF that the salt bridge makes no difference. However, the data also show that foldamer 10 seems to fold particularly poorly in aqueous THF—a change of solvent from 5% MeOH/EA to 5% H₂O/THF reduces the $Hg^{2+}$ binding energy of 10 by 3.4 kcal/mol (where the $K_{eq}$=19, the $-\Delta G_{folding}$=1.7 kcal/mol and the 95% unfolded $-\Delta G_{folding}$=1.7 kcal/mol). This energy is enough to shift a system from 95% folded to 95% unfolded.

Hence, the data indicate that folding depends not only on the size/structure of the polar solvent, but also on that of the less polar solvent (otherwise, folding in water/butanol and water/t-butanol would not be so different). Folding experiments were then conducted in water in acetonitrile/EA (1/2) because cyclic solvents such as THF/MTHF are not good for folding. EA was selected because it worked many times as the nonpolar component in the folding-friendly solvents (e.g., DMSO in hexane/EA=2/1 for 6 and DMSO/EA for 102). Acetonitrile was added simply to assist dissolution of water.

sition, a stronger acceptor band at the beginning of the titration (i.e., in low-polarity region) corresponds to a higher population of the folded conformer, as efficient FRET is only possible in the folded state. Upon addition of polar solvent, the acceptor emission will decrease when the unfolded state (with weak acceptor emission) becomes increasingly populated. The curve eventually reaches a low plateau when all the foldamers become fully unfolded with sufficient amount of the polar solvent added.

On the basis of solvent-denaturation studies, 102 is nearly completely unfolded with 5% water in acetonitrile/EA=1/2. Since the size of the polar solvent makes a large difference, studies were also performed on folding in acetonitrile/EA (1/2) with MeOH or EtOH as the polar additive. All of the denaturation curves start out with similar initial acceptor emission, which is reasonable because the initial solvents differ by only 1% in composition. Upon addition of the polar solvents, the folded conformer begins to unfold. The steeper the solvent-titration curves, the more susceptible the folded conformer is to the polar solvent and the lower its stability in that solvent mixture. The data therefore indicate that the stability of the folded conformer increases as follows: water<methanol<ethanol. Therefore, the oligocholate folds better as the polar solvent gets larger. This trend has nothing to do with acetonitrile because it is also observed in other mixtures, including in ROH/EA and in ROH/hexane/EA. Note that water cannot be employed in the latter two solvent systems because of its immiscibility with EA and/or hexane.

There could be two reasons for the increased folding ability of 102 in the order of water<methanol<ethanol. First, the salt bridge becomes more stable as the hydrogen-bonding ability of the solvent decreases. In other words, a more stable salt bridge in the ethanol mixture should make folding easier than in the aqueous mixture. The second possible reason is from the microphase separation model shown in FIG. 14B. As the polar additive becomes larger and less hydrophilic, a smaller extent of phase separation is needed in the nanocavity, and should impose a less costly burden to the folding process.

In order to determine which of the above two effects is more important, the conformation of 102 in methanol/MTHF was compared with that in methanol/EA. Methanol is completely miscible with either MTHF or EA and both MTHF and EA are nonpolar. Neither has appreciable solubility in water. Their $E_T30$ values, which are indicators for their polarity, are 36.5 for MTHF and 38.1 for EA (Marcus, Y. *The Properties of Solvents*; Wiley: New York, 1999; pp 142-154). Hence, if the strength of the salt bridge is the controlling factor in the folding process, MeOH/MTHF should be slightly better than the somewhat more polar MeOH/EA mixture.

Foldamer 102 folded well in MeOH/EA, but was completely unfolded in all MeOH/THF mixtures (data not shown). Since good folding was also obtained in MeOH/Et$_2$O, the difference in EA and MTHF could not be caused by the ester/ether difference. The data therefore indicate that microphase separation is the major factor controlling folding.

Solvent Effects in The Parent Cholate Hexamer. The data indicate that oligocholate folding is facilitated by a small amount of polar solvent that strongly solvates the cholate a faces. That was why DMSO/CCl$_4$ and DMSO/hexane/EA were successfully used as folding solvent systems, where DMSO is a strong hydrogen-bond acceptor and interacts strongly with the OH groups on the cholate a faces. Data described in the previous two sections reveals that the size and the structure of the polar and the nonpolar solvents also affects the folding reaction. These conclusions were drawn from the externally stabilized (e.g., 10, stabilized by the Hg—S complexation) or internally stabilized (e.g., 102) foldamers.

The folding of the D-A-labeled hexamer 6 was studied further to ascertain whether similar factors can modulate non-stabilized foldamers. Previously, this foldamer was found to fold reasonably well in 1-5% DMSO in hexane/EA (2/1). To verify the size effect of the polar solvent, solvent titrations in hexane/EA (2/1) were performed with methanol, ethanol, propanol, isopropanol, t-butanol, and butanol, as the polar solvent. The titration curves obtained (not shown) indicate that the folding ability roughly increased as follows: methanol<ethanol≈propanol<isopropanol<t-butanol, if butanol is ignored for the moment.

These results are almost the opposite to what is observed previously, i.e., methanol>ethanol>propanol≈isopropanol≈t-butanol>butanol when using the mercury-binding foldamer 10. There is, however, no contradiction here, because the alcohol is the most polar component in ROH/hexane/EA for the folding of 6, but is the less polar component in H$_2$O/ROH for the folding of 10. Once this difference is clarified, it is clear that the two orders are quite consistent with each other. In the ROH/hexane/EA mixture, as the alcohol gets larger, a smaller extent of phase separation (from hexane/EA into the hydrophilic nanocavity) is needed and is less costly—this is exactly the same size effect observed in both 10 and 102. The fact that butanol was so much worse than t-butanol for the folding of 6 is probably due to the increased hydrophobicity, which makes it less able to solvate the cholate a faces than t-butanol. The result is weaker preferential solvation and lower driving force for the folding.

Another conclusion from the study of 10 and 102 is that the size/structure of the nonpolar solvents is also critical. To verify this in the parent oligocholates, foldamer 6 was studied in three additional pairs of nonpolar solvents-hexane/MTHF (2/1), cyclohexane/EA (2/1), and cyclohexane/MTHF (2/1), with methanol as the common polar solvent. These comparisons were selected in part because hexane (M.W. 86, d=0.65 g/mL, $E_T30$=31.0) and cyclohexane (M.W. 84, d=0.77 g/mL, $E_T30$=30.9) are comparable in molecular weight, density, and polarity, as are EA (M.W. 88, d=0.89 g/mL, $E_T30$=38.1) and MTHF (M.W. 86, d=0.85 g/mL, $E_T30$=36.5) (Marcus, Y. *The Properties of Solvents*; Wiley: New York, 1999; pp 142-154). Therefore, when the four pairs of solvents, including hexane/EA, are compared, the main difference should come from the size and/or the (cyclic/acyclic) structure of the nonpolar solvent.

Folding once again was strongly disfavored in cyclic solvents. When either EA or hexane is replaced by the cyclic counterpart—namely, by MTHF or cyclohexane—folding was weakened. In the mixture of methanol in cyclohexane/MTHF, when both nonpolar solvents are changed to cyclic ones, 6 is unable to fold at all, as shown by the weak acceptor fluorescence throughout the solvent titration. This dramatic effect of cyclic solvents is totally in line with the inability of 6 to fold in MeOH/MTHF, despite a potentially strong intramolecular salt bridge.

One reason for the poor folding of the cholate foldamers in cyclic nonpolar solvents may be that cyclic solvents have difficulty entering the nanocavity formed during folding. Recently, Sansom and co-workers, by molecular simulations, showed that water is unable to enter a hydrophobic pore of 4.5 Å in diameter, despite the fact that the pore is apparently large enough to accommodate three water molecules (Beckstein et al. *J. Phys. Chem. B* 2001, 105, 12902-12905; Beckstein et al. *FEBS Lett.* 2003, 555, 85-90). Cyclohexane is about 6-7 Å in diameter. It is unclear how, if at all, it will enter the hydrophilic nanocavity formed by folding. However, if its behavior in a hydrophilic nanocavity can be mirrored at all by how water behaves in a hydrophobic one, one would expect cyclohexane (or MTHF) will have difficulty entering the 1 nm cavity of the folded oligocholate. On the other hand, a linear molecule such as hexane (or EA) should enter the hydrophilic nanocavity much more easily, as it can better avoid unfavorable hydrophilic/hydrophobic contact with the wall. In this sense, poor folding in cyclic nonpolar solvents is in total agreement with the folding model. When the nonpolar solvent is rejected by the nanocavity, a larger extent of phase separation of the polar solvent is needed and represents a larger cost for the folding, just as in the case of small polar solvent.

Therefore, the data indicate that folding is at least partially driven by microphase separation of solvents within a nanometer-sized hydrophilic cavity.

Use of Detergent Micelles

Because foldamers 10 is mostly nonpolar, it is insoluble in water and thus, unless modified, it may not be employed to detect mercury ions in aqueous solutions. Experiments were therefore conducted to ascertain whether incorporation of foldamer 10 into surfactant micelles would overcome such insolubility problems. The surfactant micelles not only provide a hydrophobic local environment to solubilize the foldamer sensor, but also permit modulation of its sensitivity by the ionic characteristics of the surfactant.

The three surfactants chosen in this study were CTAB (cetyltrimethylammonium bromide), SDS (sodium dodecylsulfate), and Triton X-100. They are representative examples of cationic, anionic, and nonionic surfactants. Their CMCs are 1, 8, and about 0.3 mM in water, respectively (Kano, K.; Ueno, Y.; Hashimoto, S. *J. Phys. Chem.* 1985, 89, 3161-3166; Rosen, M. J. *Surfactants and Interfacial Phenomena*, $2^{nd}$ Ed.; Wiley: New York, 1989; Chapter 3).

The first indication for internalization of 10 within the micelles came from its fluorescence intensity. In general, Dansyl derivatives emit fluorescence more strongly in organic solvents and are nearly nonfluorescent in water. However, the present studies indicated that the emission intensity of 10 was stronger in less polar solvents, such as 5% MeOH/ethyl acetate, THF, and t-BuOH, than in more polar solvents, such as MeOH and EtOH. In water/THF mixtures, the emission of 10 clearly decreased with a higher percentage of water. Because the intensity of 10 in the three surfactant solutions above the CMC was comparable to those in organic solvents, it is reasonable to assume that the Dansyl group of 10 was in a relatively hydrophobic environment. Among the three surfactants, Triton X-100 gave the strongest fluorescence for 10, suggesting that its micelle is the most hydrophobic.

Figure 15I:
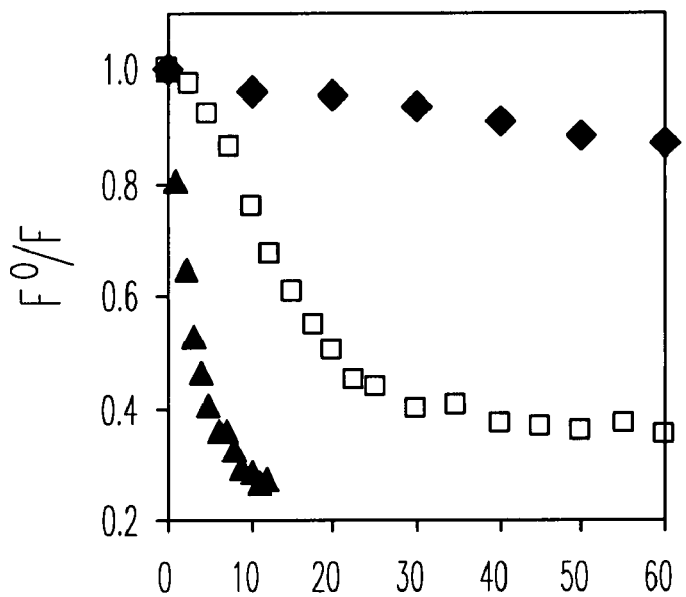
FIG. 15I shows the normalized maximum fluorescence intensity of 10 in 5 mM CTAB (◆), 1 mM Triton X-100 (□), and 8 mM SDS (▲) as a function of [Hg$^{2+}$].

The maximum emission wavelength ($\lambda_{max}$) of Dansyl is sensitive to the polarity of its local environment, and typically shifts to down (towards blue) as the environment becomes less polar (Li, Y.-H.; Chan, L.-M.; Tyer, L; Moody, R. T.; Himel, C. M.; Hercules, D. M. *J. Am. Chem. Soc.* 1975, 97, 3118-3126). Among the solvents studied, 5% MeOH/ethyl acetate and THF give the lowest $\lambda_{max}$ at 497 and 487 nm, respectively, whereas polar solvents afford higher $\lambda_{max}$, up to 522 nm for 30% $H_2O$ in THF. With surfactants, the $\lambda_{max}$ of 10 ranges from 487 to 497 nm, also suggesting that 10 is in a fairly nonpolar environment. Among the three surfactants, Triton X-100 affords the lowest $\lambda_{max}$ (487 nm) for the Dansyl group, consistent with a most hydrophobic micelle. Being confident of micellar incorporation of 10, titration with $Hg(NO_3)_2$ in the presence of surfactants at or above their CMC. The type of surfactant caused a large effect on foldamer 10 binding with $Hg^{2+}$. In particular, the fluorescence of foldamer 10 was nearly unquenched by $Hg^{2+}$ in CTAB solutions, but quenched easily in Triton X-100 and most efficiently in SDS micelles (FIG. 15I). The binding strength clearly followed the order of cationic micelle<<nonionic micelle<anionic micelle. This may occur because $Hg^{2+}$ is positively charged and should be repelled by CTAB headgroups but attracted by those of SDS. Nonionic micelles give intermediate affinity because neither favorable nor unfavorable electrostatic interactions are involved. In the most "folding-friendly" solvents, such as 5% MeOH in hexane/ethyl acetate (2/1), 10 was shown to detect 20 nM concentrations of $Hg^{2+}$. Binding was noticeably weaker when 10 is in surfactant micelles, but the micelles still allowed easy detection of $Hg^{2+}$ at 1 µM (FIG. 15I, A).

As described above, the 1:1 binding of $Hg^{2+}$ with foldamers 10 occurred as assessed using a Job plot. The association constants determined by nonlinear least-squares fitting are summarized in Table 6.

TABLE 6

Binding data for 10 and $Hg(NO_3)_2$ at 25° C.

| Entry | surfactant[a] | $K_a$ ($M^{-1}$) | $-\Delta G$ (kcal/mol) |
|---|---|---|---|
| 1 | Triton X-100 (10 mM) | $(6.3 \pm 0.9) \times 10^4$ | 6.5 |
| 2 | Triton X-100 (5 mM) | $(7.6 \pm 1.4) \times 10^4$ | 6.7 |
| 3 | Triton X-100 (2 mM) | $(6.6 \pm 1.6) \times 10^4$ | 6.6 |
| 4 | Triton X-100 (1 mM) | $(6.4 \pm 1.3) \times 10^4$ | 6.5 |
| 5 | SDS (40 mM) | $(1.1 \pm 0.2) \times 10^5$ | 6.9 |
| 6 | SDS (16 mM) | $(2.0 \pm 0.3) \times 10^5$ | 7.2 |
| 7 | SDS (8 mM) | $(6.5 \pm 0.5) \times 10^5$ | 7.9 |
| 8 | SDS (4 mM) | $(4.8 \pm 1.0) \times 10^5$ | 7.7 |
| 9 | SDS (2 mM) | $(4.3 \pm 0.4) \times 10^5$ | 7.7 |
| 10 | SDS (1 mM) | $(3.3 \pm 0.6) \times 10^5$ | 7.5 |
| 11 | SDS (0.2 mM) | $(1.7 \pm 0.3) \times 10^5$ | 7.1 |
| 12 | SDS (0.1 mM) | $(1.2 \pm 0.1) \times 10^5$ | 6.9 |

[a]$K_a$ (<400 $M^{-1}$) could not be determined accurately in 5 mM CTAB. The solution turned cloudy with >90 µM $Hg^{+2}$, probably due to the low solubility of the $HgBr_2$ formed from $Hg(NO_3)_2$ and CTAB.

Examination of the data quickly reveals that the type of surfactant not only has a direct impact on $K_a$, but also influences how $K_a$ responds to the concentration of the surfactant. For example, $K_a$ is nearly the same when the concentration of Triton X-100 is varied between 1 and 10 mM. This insensitivity was also observed from nearly identical titration curves generated using Triton solutions with different concentrations (data not shown). On the other hand, $K_a$ is clearly dependent upon the concentration of SDS (entries 5-12, Table 6). Furthermore, fluorescence titrations could be obtained with SDS well below its CMC of 8 mM, even down to 0.1 mM. However, when the concentration of Triton X-100 dropped below the CMC, the fluorescence of 10 became unstable. Thus, pre-micellization is not required for the solubilization of 10 by SDS, but seems to be important with the nonionic Triton X-100.

In order to aggregate, SDS molecules have to overcome substantial electrostatic repulsion that is not present during the aggregation of Triton. Due to the neutrality of 10, co-aggregation of SDS and 10 should be more favorable than aggregation of SDS with other SDS molecules. In contrast, co-aggregation of Triton and 10 does not have any particular advantage over the homoaggregation of Triton. In essence, a hydrophobic molecule such as 10 can induce the aggregation of SDS, but cannot do so (at least not as effectively) for the nonionic Triton. This is probably one reason why pre-micellization is needed for Triton to solubilize 10, but is unnecessary for SDS.

Figure 15J:
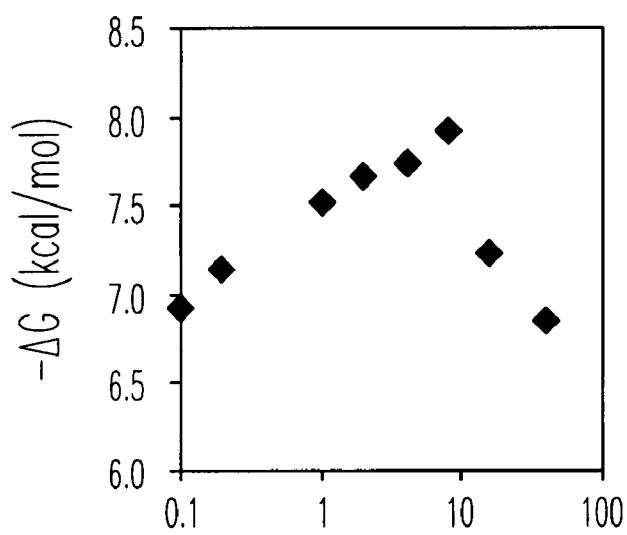
FIG. 15J shows the binding energy (−ΔG) between 10 and Hg$^{2+}$ as a function of SDS concentration [SDS].

Interestingly, the binding energy ($-\Delta G$) in SDS solutions shows a distinctive maximum at the CMC of the surfactant (FIG. 15J). Negatively charged surfactants undoubtedly can enhance the effective concentration of positively charged $Hg^{2+}$ on the surface of the micelles. This "mercury-concentrating" effect is very likely to be most effective at the CMC, at which the surfactants start to work cooperatively to attract the metal ion. With a further increase in the concentration of SDS, more micelles are created that are sensor-free. (Note that in these experiments the surfactant is used at a much higher concentration than the sensor.) These additional micelles are expected to compete with the sensor-containing micelles for $Hg^{2+}$ and thus reduce the binding strength.

This Example therefore describes a fluorescent mercury sensor of the invention. The general scheme for employing foldamers as sensors for metal ions is illustrated in FIG. 14A. Moreover, the binding affinity of the foldamer to the metal (and thus its sensitivity as a sensor) can be regulated by modulating the solvent conditions. The sensitivity of the foldamer for metal ions was highly tunable—the same foldamer sensor could detect mercury ions at concentrations as low as tens of nanomolars or as high as hundreds of micromolars.

Thus, one aspect of the invention is a highly tunable, selective fluorescent sensor for metal (e.g., mercury and zinc) ions based on a hybrid foldamer that includes methionine residues. Such tunability in binding affinity and the exquisite sensitivity of the foldamer is a general result of a cooperatively folded structure of the hybrid foldamer. This concept, therefore, is not limited to a particular system and such foldamers can be used for molecular recognition of metals and as environmentally responsive sensors.

Example 4

Zinc-Binding Foldamers

This Example describes foldamers that can bind metal ions such as zinc.

Materials and Methods

A hybrid foldamer (101) was made whose folding is particularly sensitive to $Zn^{2+}$. Other divalent cations behaved quite differently from zinc, either due to weaker binding or their different interactions with the pyrene labels on the foldamer. Hence, foldamers binding to zinc could be distinguished from foldamers binding to other metal ions.

Oligomer 101 was designed so that folding would promote formation of an excimer by the two pyrenyl groups at the ends of the oligomer chain. To facilitate the excimer formation, the pyrenes were linked to the foldamers through relatively flexible tethers. As described above, there appear to be three repeat units per one turn of an oligocholate. Oligomer 101 has six cholate units and thus should make two full turns, assuming the incorporated glutamic acids cause no significant change in the periodicity of the foldamers. The end-to-end distance, according to the CPK model of a folded cholate hexamer, is about 1 nm, but can reach several nanometers for the unfolded conformer. Therefore, the pyrene excimer should be easily formed in the folded state but largely absent in the unfolded state. A structure of foldamer 101 is provided below.

MeOH to less than 0.3 when the solvent mixture contained greater than 14% MeOH. This change corresponded to a transition from a compact, folded conformation to an extended, unfolded one. The conformational change was highly cooperative, with most of the change taking place within a narrow range (10-14% MeOH/EA) of change in solvent ratio.

Figure 16A:
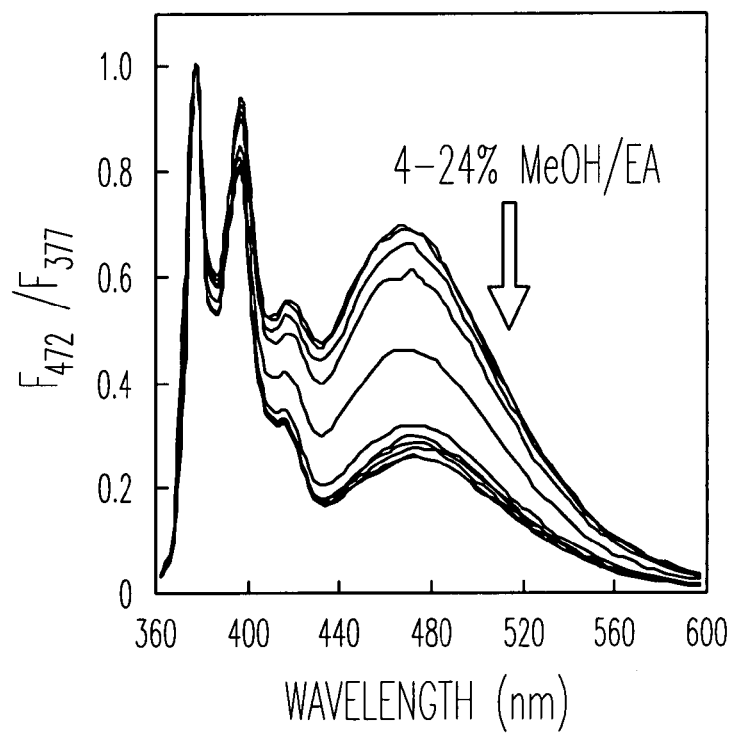
FIG. 16A shows the normalized fluorescence spectra of oligomer 101 in different mixtures of methanol and ethyl acetate.

The data in FIG. 16A can be fitted into a two-state transition model (eq 1), from which the folding/unfolding equilibrium in every solvent composition can be determined.

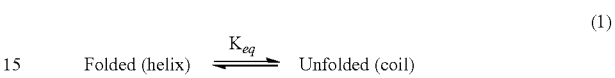

(1)

Figure 16B:
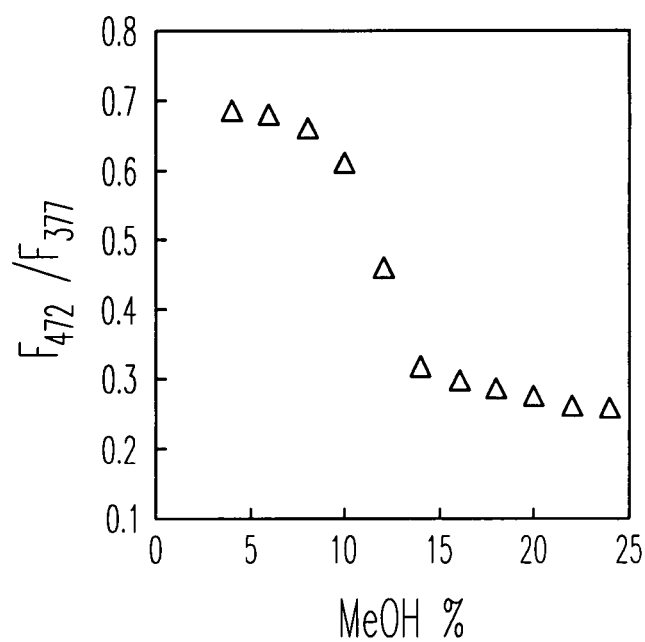
FIG. 16B shows the excimer/monomer ratio ($F_{472}/F_{377}$) for foldamers 101 as a function of solvent composition.
Figure 16C:
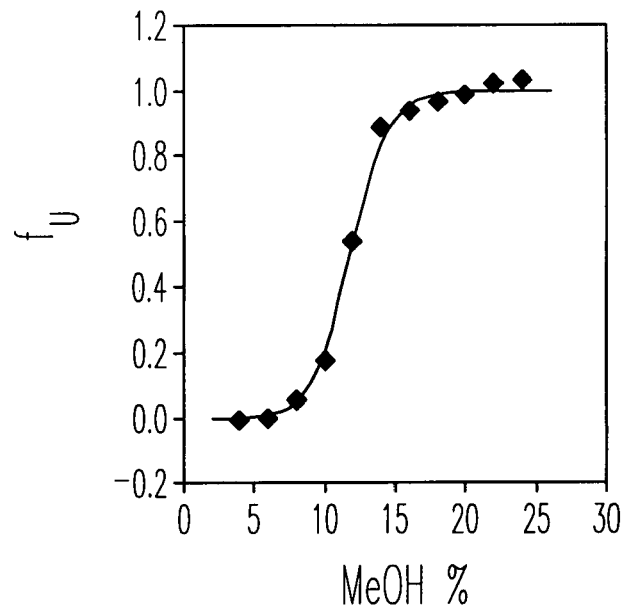
FIG. 16C illustrates the fraction of the unfolded oligomer 101 as a function of the volume percentage of MeOH in ethyl acetate. The theoretical curve is a nonlinear least-squares fitting to a two-state transition model.
Figure 16D:
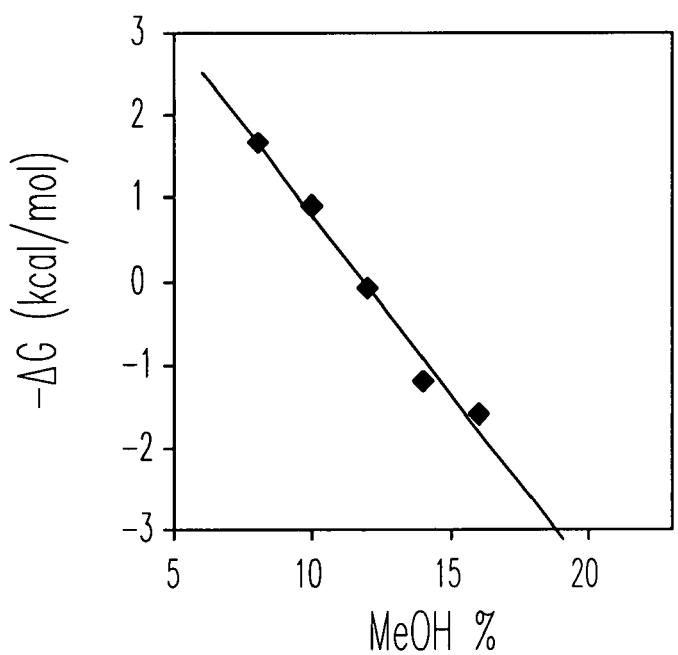
FIG. 16D shows the unfolding free energies for oligomer 101 as a function of solvent composition.

As shown in FIG. 16C, greater than 90% of the oligomer was folded in 4-8% MeOH/EA. Addition of another few percent of methanol quickly unfolded the oligomer. When somewhat greater than 14% MeOH was present, over 90% of oligomer 101 became unfolded.

Oligomer 101 folded better than the parent foldamer that had no amino acids in the backbone. For example, the parent cholate hexamer could only fold when the nonpolar solvents were hexane/EA, instead of EA alone. The folded oligocholate has a hydrophobic exterior and a hydrophilic interior so that a small amount of the polar solvent is microphase-separated from the bulk to the interior. Such phase separation of methanol from EA becomes easier when the completely nonpolar hexane is added to EA. Even in hexane/EA (2/1), a nonpolar mixture proving the best for the folding of the oligocholates, the parent cholate hexamer could fold only when less than 5% MeOH was present. As shown in the previous Example, insertion of two methionines into the cholate hexamer helped folding somewhat, possibly because the amino acids introduced some degree of flexibility into the backbone. Certain levels of flexibility are beneficial so that the folded state will not be overly strained. However, too much flexibility is detrimental to the folded conformer because the loss of

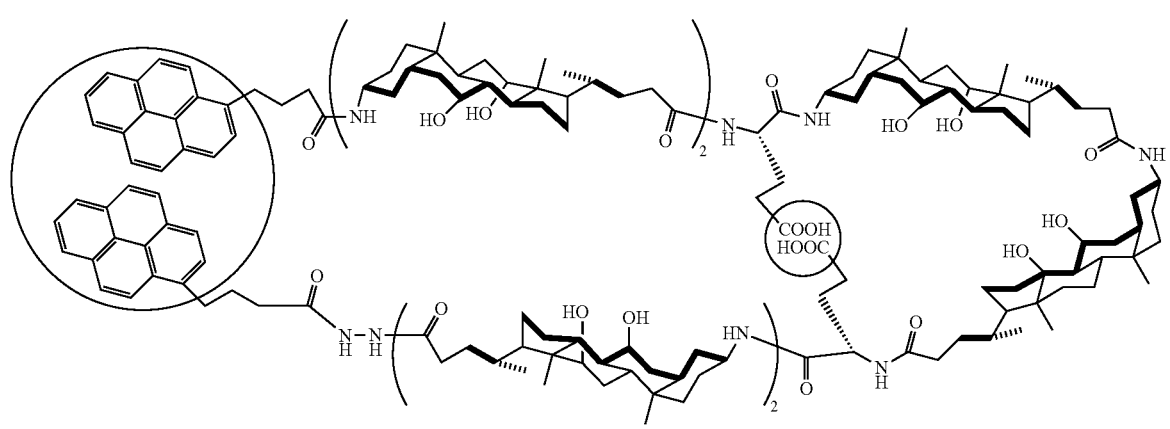

101

The pyrene excimer was indeed a good indicator for folding of foldamer 101. As shown by FIGS. 16A and 16B, when the fluorescence of hexamer 101 was examined in different mixtures of methanol and ethyl acetate (EA), the excimer/monomer ratio (i.e., $F_{472}/F_{377}$, the emission intensity at 472 nm over that at 377 nm) decreased from about 0.7 in 4-8% entropy will be too large during folding. Because the only structural difference between methionine and glutamic acid lies in the side chain, the much more significant enhancement in the folding in oligomer 101 comes from the carboxylic acid side chains. Most likely, the carboxyl groups were involved in intramolecular hydrogen bonds either with each other or with other amide/hydroxyl groups in the molecule. However, there is no need to form specific, fixed hydrogen bonds in order to stabilize the folded conformer. Even if the carboxyl group jumps from one hydrogen-bond partner to another, folding is facilitated.

Foldamer 101 exhibits highly cooperative folding/unfolding reactions and is therefore very useful as a sensor. For example, a divalent metal ion such as calcium should crosslink the two carboxylic acids and stabilize the folded state. Indeed, screens quickly revealed that several divalent cations promoted folding, where zinc(II) turned out particularly effective.

Figure 16E:
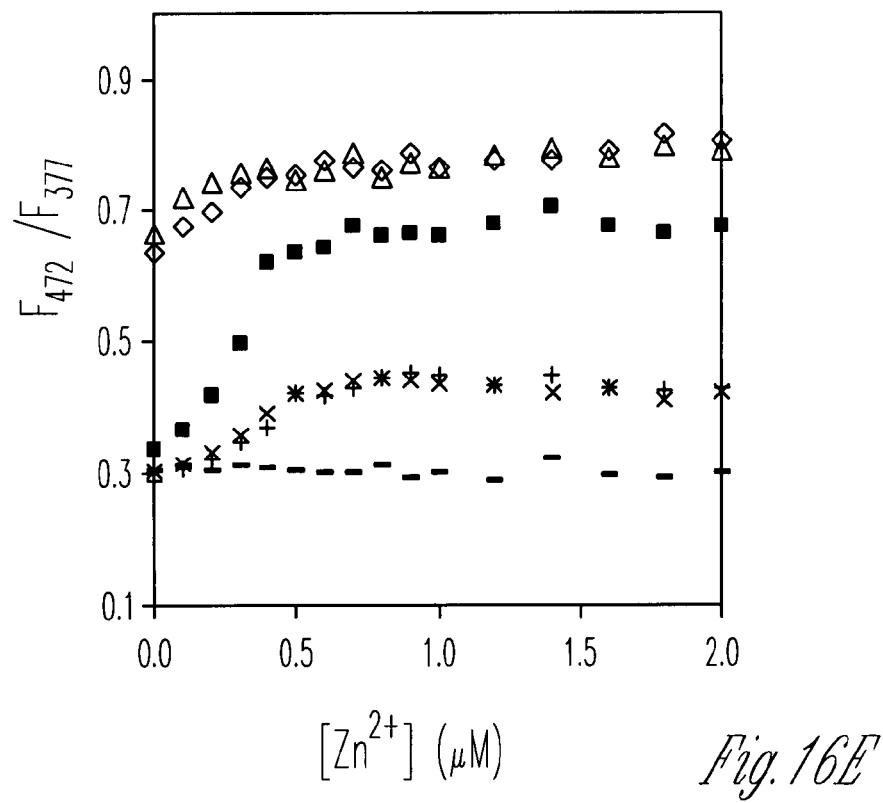
FIG. 16E shows the excimer/monomer ratio ($F_{472}/F_{377}$) as a function of [Zn(OAc)$_2$] in 5% (Δ), 10% (◊), 15% (■), 20% (×) 25% (+), and 100% (−) MeOH in EA. [101]=0.5 µM.
Figure 16F:
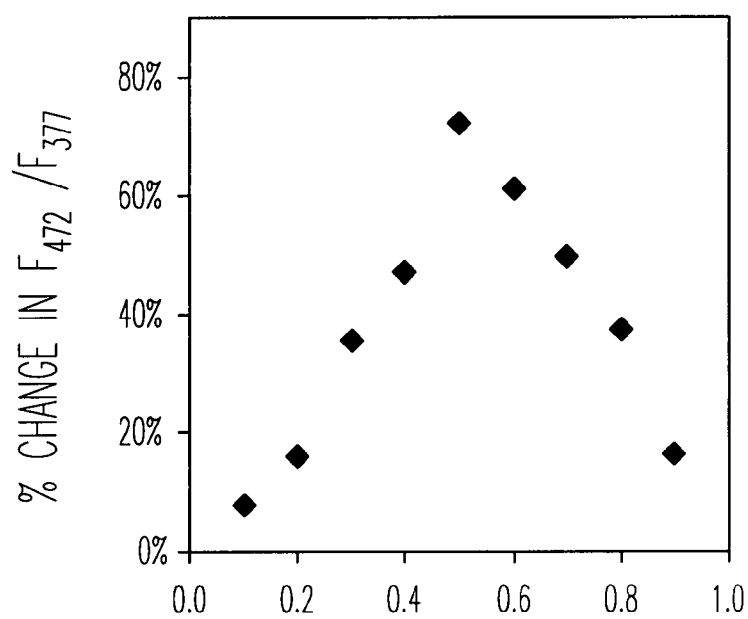
FIG. 16F shows a Job plot for the binding between foldamer 101 and Zn(OAc)$_2$ in 15% MeOH/EtOAc. The total concentration of 101 and Zn(OAc)$_2$ was kept at 1.0 µM. χ=[Zn(OAc)$_2$]/{[101]+[Zn(OAc)$_2$]}.

FIG. 16E shows the pyrene excimer/monomer ratio as a function of $Zn^{2+}$ concentration in six different MeOH/EA mixtures. In 5 and 10% MeOH, oligomer 101 was largely folded (as seen in FIGS. 16B and 16C). As expected, adding $Zn^{2+}$ only slightly increased the excimer/monomer ratio (FIG. 16E, Δ and ◊). The most significant enhancement of pyrene excimer by $Zn^{2+}$ happened in 15% MeOH (■). The binding must be extremely strong, as seen by the sharp transition of the $F_{472}/F_{377}$ curve at 0.5 μM of zinc ions, or at 1:1 ratio. To further confirm the binding stoichiometry, the Job analysis was carried out, in which the total concentration of foldamer 1 and $Zn^{2+}$ was kept at 1.0 μM while the ratio between the two was varied from 1:9 to 9:1. The largest change in $F_{472}/F_{377}$ clearly occurred at 1:1. Once again, the Job plot was extremely sharp, indicating the tightness of binding. A nonlinear least-squares fitting of data in FIG. 16E showed the binding constant was at least $10^8 M^{-1}$.

Binding between foldamer 101 and $Zn^{2+}$ was still detectable in 20 and 25% MeOH (FIG. 16E, × and +, respectively), but the extent of change in the excimer/monomer ratio was much smaller. Note that in 15, 20, and 25% MeOH/EA, even after the binding between 101 and $Zn^{2+}$ was saturated, the excimer/monomer ratio never reached the value for the fully folded, uncomplexed foldamer (i.e., ca. 0.7 according to FIG. 16b). The most reasonable explanation for the lower $F_{472}/F_{377}$ ratio for the $Zn^{2+}$-complexed foldamer is that pyrene fluorescence was quenched by the metal ion (vide infra). A lower $F_{472}/F_{377}$, for example, could be easily obtained if the emission at 472 nm was quenched more strongly by $Zn^{2+}$ than that at 377 nm. In these experiments, most metal ions quenched the fluorescence of the pyrene (both that of the monomer and of the excimer). However, it was difficult to fit the quenching data directly to a 1:1 binding isotherm. The apparent binding constants were quite different depending on the wavelength at which the quenching was monitored. This was probably due to multiple quenching mechanisms involved. The bound metal ion, the formation of the pyrene excimer, the change in local solvent composition during folding could all affect the emission of both the monomer and the excimer, most likely to different extents.

Folding was made possible by both the curvature of the cholate (toward the hydrophilic face) and the entrapped polar solvents (as a result of microphase separation), which simultaneously solvate multiple inward-facing NH/OH groups on the hydrophilic faces of the cholates.

$Zn^{2+}$ was not able to promote the formation of pyrene excimer in neat methanol (FIG. 16E, -). Given the 1.4 nm heat-to-tail length of a single cholate unit, it is unlikely that oligomer 101 binds $Zn^{2+}$ in the unfolded state. When the folded conformer becomes disfavored by the solvent, binding has to overcome the unfavorable folding reaction and was shown to become significantly weaker. Phase separation in MeOH/EA may help with folding when the mixed solvent is used, but such phase separation no longer exists in neat methanol. Methanol itself also represents a poor medium for a folded oligocholate, which has a hydrophobic exterior, and accordingly, poor binding of $Zn^{2+}$ in 100% methanol is observed.

Figure 16G:
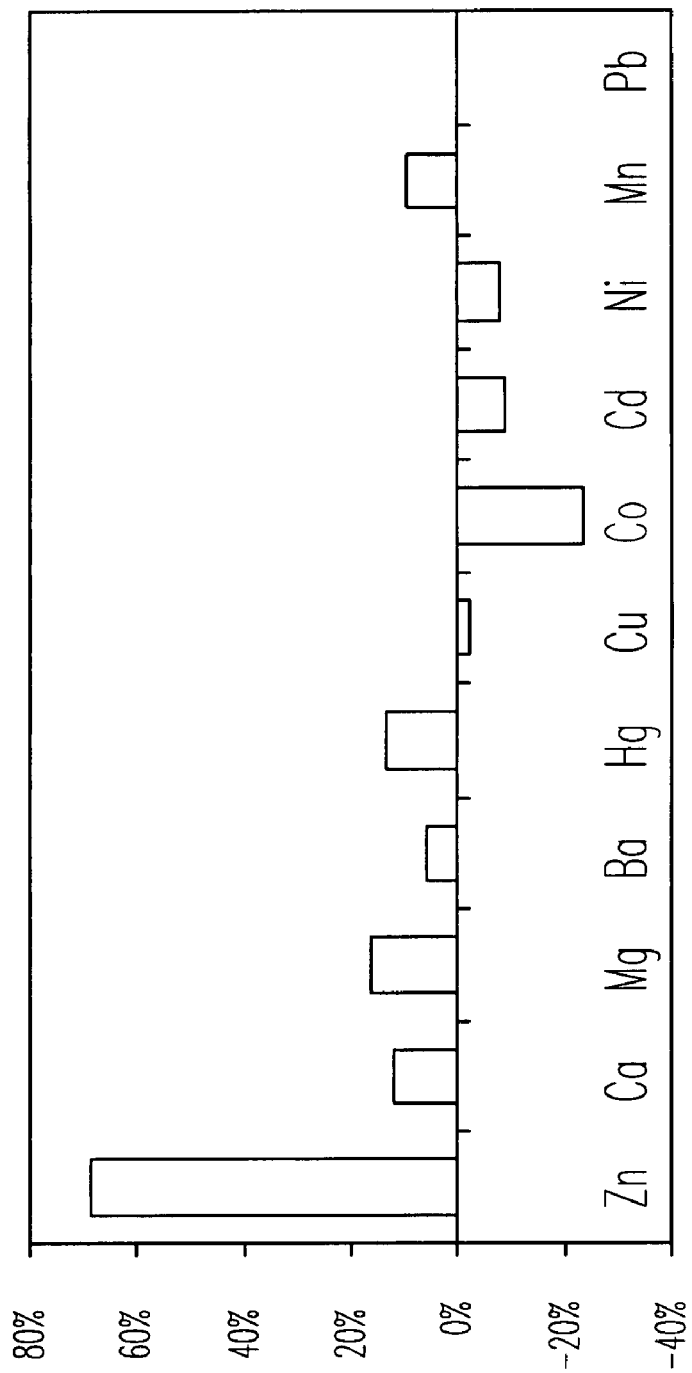
FIG. 16G is a bar graph showing the change in the excimer/monomer ratio of foldamer 101 (0.5 µM) in 15% MeOH/EtOAc upon addition of various divalent metal ions (0.4 µM).

The effects of other cations on the folding of oligomer 101 were also observed, including divalent cations $Ca^{2+}$, $Mg^{2+}$, $Ba^{2+}$, $Hg^{2+}$, $Cu^{2+}$, $Co^{2+}$, $Cd^{2+}$, $Ni^{2+}$, $Mn^{2+}$, and $Pb^{2+}$, as well as some monovalent cations, such as $Na^+$, $K^+$, and $NH_4^+$. Some of them (e.g., $Ca^{2+}$, $Mg^{2+}$, and $Ba^{2+}$) behaved like $Zn^{2+}$ toward the foldamer—i.e., their presence promoted the excimer formation (data not shown). The binding was considerably weaker, however. The monovalent cations (data not shown) had substantially no effect on the excimer/monomer ratio. The rest of the divalent cations all exhibited different behaviors, sometimes giving an overall decrease in $F_{472}/F_{377}$ throughout the titration (e.g., $Co^{2+}$, data not shown), other times showing an increase initially followed by a decrease (e.g., $Mn^{2+}$, data not shown). It seems that the monomer and the excimer of pyrene were quenched differently when different metal ions were bound by the foldamer. FIG. 16G shows the percent change of $F_{472}/F_{377}$ for these metal ions in 15% MeOH/EtOAc after addition of 0.4 μM divalent metal ion. The excimer/monomer ratio responded quite differently to the same concentration (0.4 μM) of divalent cations, however $Zn^{2+}$ exhibited the strongest ability to enhance the excimer formation.

In summary, a foldamer has been designed that relied on the formation of pyrene excimer as a signature for its folding and two internal carboxylic acids to detect $Zn^{2+}$. The most sensitive detection of $Zn^{2+}$ happened near the transition region on the "solvent denaturation" curve. The sensitivity was the highest when most (ca. 90%) of the foldamer was just unfolded by the methanol.

Example 5

Foldamer Thermosensors

This Example describes thermally sensitive foldamers.

Temperature-sensing in the present invention is based on the thermal unfolding of foldamers. This concept includes both "on-off" and "off-on" switching mechanisms.

For the FRET-based temperature sensors, the amino acid tryptophan will be used as the donor because it can transfer energy to a large number of acceptors. Six acceptors are chosen for these studies (Table 6). All the $R_0$ values are comparable to that of naphthalene-Dansyl ($R_0$=2.2 nm) and should work well for the cholate pentamer through heptamer. For simplicity, tryptoamine (which has the same fluorophore as tryptophan) will be attached to the carboxyl terminal of the foldamers. All the fluorophores listed in Table 7 have commercially available reactive forms (e.g., succinimidyl ester, isothiocyanate, tetrafluorophenyl ester, sulfonyl chloride, etc.) that can react with the amino terminal of the foldamers.

TABLE 7

FRET data for tryptoamide as the donor.

| Acceptor (Derivative of) | $R_0$ (nm) | Emission Wavelength (nm) |
|---|---|---|
| 2,5-Dimethoxy-stilbenene | 2.8 | 420 |
| Anthracene | 2.0 | 442 |
| 7-Dimethyl-aminocoumarin | 3.1 | 471 |
| Fluorescein | 2.7 | 515 |
| Dansyl | 2.2 | 520 |
| Eosin | 2.5 | 545 |

As shown in Table 7, the emission wavelength of the acceptors ranges from 420 to 550 nm. Therefore, the color of their fluorescence can be easily tuned from violet (ca. 400 nm) to indigo (ca. 445 nm) to blue (ca. 475 nm) to green (ca. 510 nm) to almost yellow (ca. 570 nm). Off-On transitions can also be designed with a non-fluorescent acceptor such as 4-dimethylamino-azobenzene (Van Der Meer, B. W.; Coker, G., III; Chen, S.-Y. S. *Resonance Energy Transfer: Theory and Data*. VCH: Weinheim, 1994; Chapter 7).

The general formula of the foldamer thermosensor is:

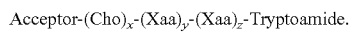

Acceptor-(Cho)$_x$-(Xaa)$_y$-(Xaa)$_z$-Tryptoamide.

wherein Cho and Xaa amino acids as described herein, and y and z are each integers independently selected from 0, 1, 2, 3, 4 or 5.

To create thermosensors with different colors, several (e.g. six) foldamer sequences with increasing conformational stabilities will be selected based. As discussed before, the number/nature of cholate monomers (Cho) and amino acids (Xaa) would be used to modulate the stability. The acceptors will be attached to the foldamers to give thermosensors that show different colors as the temperature changes. In general, the (acceptor) fluorescence decreases with higher temperatures. The temperature ranges for the different thermosensors are also expected to be different because the foldamers have different stabilities.

For "Off-On" thermosensors, the acceptor emission is strong at low temperature (with FRET) but weak/absent at high temperatures (without FRET). Hence, the above thermosensors give on-off transitions at the unfolding temperature. Basically, the acceptor quenches the emission of tryptophan (at about 340 nm) or 1-anilinonaphthalen-8-sulfonic acid (at about 480 nm) in the folded state at low temperatures, the distance between the acceptor and donor is too far to do so in the unfolded state at high temperatures. Therefore, the donor emission will be weak/absent below the unfolding temperature but strong above this temperature.

Another approach to the off-on thermosensors is to couple a fluorophore and a broad-selectivity quencher such as TEMPO (Lakowicz, J. R. Energy Transfer. in *Principles of Fluorescence Spectroscopy*, 2nd Ed.; Kluwer: New York, 1999; Chap. 13) to the two ends of the foldamer. Using this method, there is very little restriction on the fluorophore type.

The hexamer foldamer may be the best platform for the thermosensor because its amino and carboxyl termini are about 1 nm apart based on CPK models. (FRET suggests <1.5 nm D-A distance.) The commercially available 4-amino-TEMPO may need to be derivatized with a spacer like that shown below to ensure efficient quenching of the fluorescence in the folded state.

41

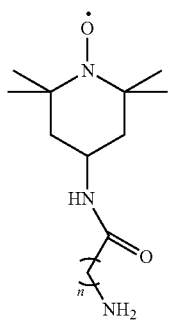

This strategy is extremely versatile because there are very few restraints on the type of fluorophore employed.

Moreover, because all of the thermosensors rely on intramolecular processes they can be used as a mixture or as a series of separate sensors. This may be useful in displays where more than one color is desired. For example, if several "off-on" sensors are mixed together, little or no fluorescence would be observed at low temperature. As the temperature increases, the thermosensors will be turned on one after another in the order of increasing conformational stability. Such a feature may be particularly attractive for easy visual distinction, because color change is much easier to detect than change of fluorescence intensity.

Example 5

Detecting Small Molecules

This Example describes foldamers that can bind small molecules, indicating that the foldamers of the invention can be used for detecting small molecules such as Like metal ions, small molecules may bind to the foldamer and influence the conformational equilibrium of that foldamer. In this way, the foldamer may be used as a molecular sensor, and report the binding event by either FRET or intramolecular charge-transfer complexation as described above.

This Example focuses on the sensing of polyanionic guests, which include many natural products such as citrate, malate, and ATP. Foldamer sensors can be developed that can recognize different anionic guests based on their size and number/distribution of their negative charges. Thus, an appropriately sized polyanionic guest can induce the folding of a polycationic foldamer with matching number of charged groups.

A general challenge in fluorescent sensing lies in the mechanism by which a binding event is converted to a readable fluorescent signal. Commonly used strategies include photoinduced electron transfer (PET), exciplex or excimer formation, and rigidization/preorganization (to change degree of delocation of π systems). See *New Trends in Fluorescence Spectroscopy: Applications to Chemical and Life Sciences*, Valeur, B. and Brochon, J.-C. Eds. (Springer: Berlin, 2001); de Silva et al. Signaling Recognition Events with Fluorescent Sensors and Switches. *Chem. Rev.* 97, 1515-1566 (1997); Rurack, K.; Resch-Genger, U. Rigidization, Preorganization and Electronic Decoupling—the "Magic Triangle" for the Design of Highly Efficient Fluorescent Sensors and Switches. *Chem. Soc. Rev.* 31, 116-127 (2002).

One benefit provided by the present foldamer sensors is their simple signal generation and transduction—binding of the analytes brings conformational changes to the foldamers that are easily detected by fluorescent or UV changes. Moreover, the foldamers offer the unique opportunity to tune the color of the output signals to almost any desired color.

The strategy employed for molecular sensors is similar to that is used for the thermosensors described above.

Basic Design Principles. The primary functional group used in the literature to bind carboxylates or phosphates is guanidinium. This group can readily be incorporated into the present foldamers by simply incorporating arginine subunits into the foldamer sequence. The amidinium-carboxylate salt bridge is reinforced by hydrogen bonds and is even quite stable in moderately polar solvents.

Target analytes (42-51) were selected to test foldamer binding to carboxylates, because these analytes have a different number (2-4) and orientation of acid groups.

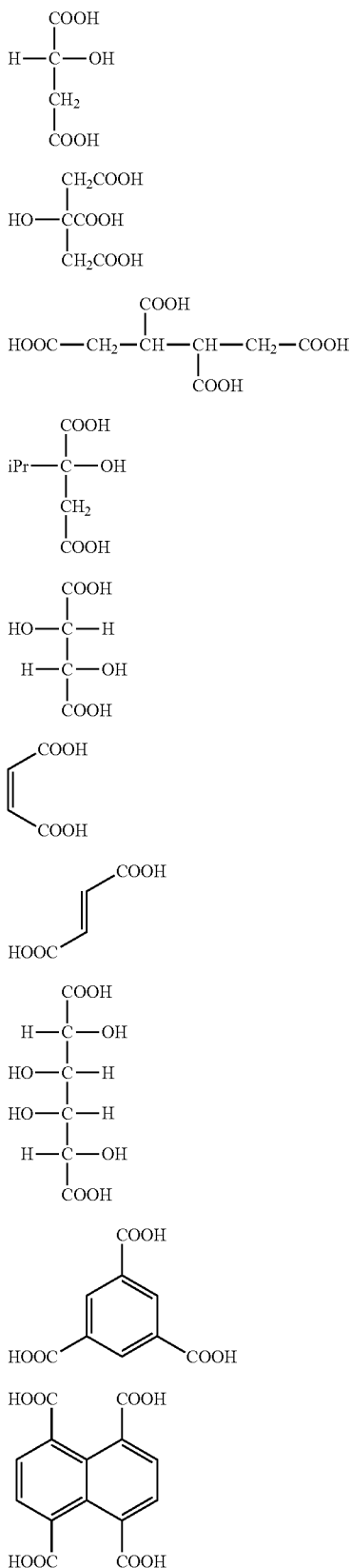

The analytes are chosen to probe different aspects of the sensor selectivity. Molecules 42, 43, and 44 have two, three, and four carboxylate groups. Molecules 45 and 46 have the same number of carboxylates as 42 but different hydrophobicity/size and hydrogen-bonding functionalities. Molecules 47-51 (in comparison to 42, 43, or 44) are different mainly in size and the orientation of the carboxylates.

It is expected that optimal binding will occur if the sensor and the analyte are complementary in size and in the number/distribution of the charged groups. Because introduction of the guanidinium groups reduces the size of the potential hydrophilic cavity, the guanidinium groups can be placed near the oligomer chain ends and/or used in the extended monomers to create sufficient internal volume. CPK/molecular modeling building and certain amount of experimental optimization will be done to guide the exact design of the sensors.

During the synthesis of the foldamers, different acceptors can be used to "color-code" the number and the locations of the guanidinium groups (represented by foldamers such as 52a-f). Also, several of these foldamer sensors can be mixed to ascertain the degree to which the foldamers, as a group, can discriminate between different carboxylic acid-bearing compound with respect to the number and distribution of the acid groups.

2,4-Dimethoxystilbene-Cho-Arg-Cho-Cho-Arg-Cho-Cho-Cho-Tryp (52a)

Anthracene-Cho-Arg-Cho-Cho-Cho-Cho-Arg-Cho-Tryp (52b)

7-Dimethylaminocoumarine-Cho-Arg-Cho-Cho-Cho-Cho-Cho-Cho-Arg-Tryp (52c)

Fluorescein-Cho-Cho-Arg-Cho-Cho-Arg-Cho-Cho-Arg-Tryp (52d)

Dansyl-Cho-Arg-Cho-Arg-Cho-Arg-Cho-Cho-Cho-Tryp (52e)

Eosin-Cho-Arg-Cho-Arg-Cho-Arg-Cho-Arg-Cho-Cho-Tryp (52t)

Foldamers 52d/52e, and 52f have three and four arginine units, and are expected to bind tri- and tetracarboxylic acids. For example, it is possible for a tetracarboxylic acid to bind foldamer 52f and emit a distinguishable acceptor signal. Other carboxylic acid containing compounds may differentially bind to different foldamers. By correlating the type of signal emitted with the structure of the carboxylic acid containing compound, the binding patterns of the foldamers are determined. Thus, molecular sensors are developed that can quickly signal the presence of an analyte (e.g. a carboxylic acid containing compound) of known structure.

Colorimetric sensors. Fluorescent sensors have the advantage of high sensitivity. Colorimetric detection, on the other hand, can be easily visualized, needs no special equipment and can be particularly useful in certain applications (e.g., field tests or in-home tests administered by patients). The present foldamers sense the analytes through their reversible conformational changes. When such conformational changes are reported by changes in absorption within the visible spectrum, the foldamer sensors of the invention are colorimetric sensors.

One mechanism that is compatible with the above foldamer sensors is intramolecular charge-transfer (CT) complexation. Instead of using a FRET donor/acceptor pair, a CT donor/acceptor can be attached to the two ends of the foldamer. The overall mechanism is fairly similar to what is used in the FRET-based sensors, except that CT complexes can only form when using a very short Donor-Acceptor distance (ca. 3-4 Å) but FRET can occur over several nanometers. Thus, shorter foldamer oligomers should be used (e.g. a hexamer) when CT is employed.

The acceptors (53a-c) and donors (54a-f) are common CT components with different electron donating and accepting abilities (Foster, R. *Organic Charge-Transfer Complexes*; Academic Press: London, 1969) which permit tuning of the color of the CT band.

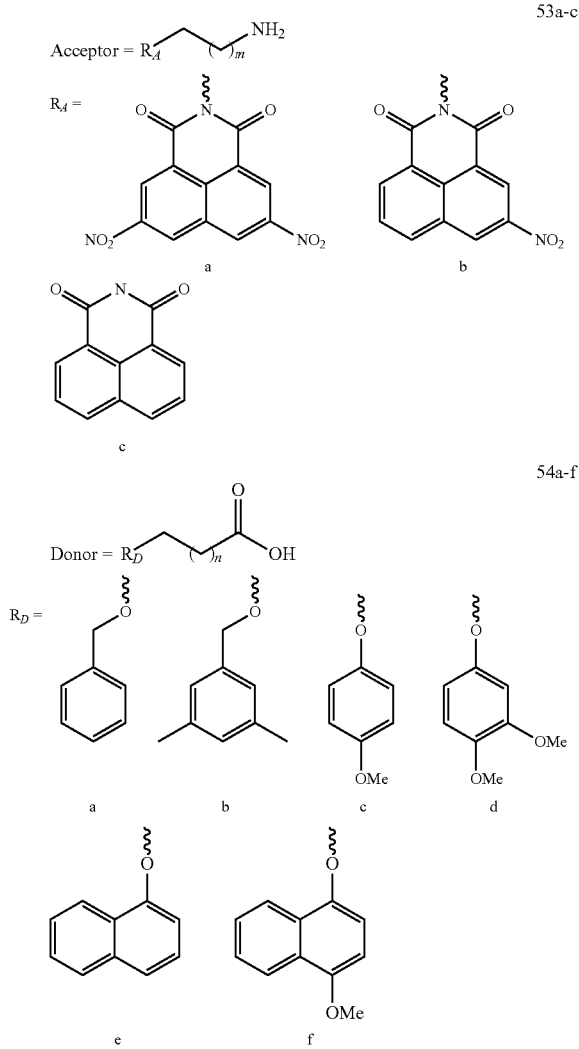

To initially evaluate CT complexation with the present foldamers, intermolecular CT complexes formed between these donors and acceptors are studied. Selected donor-acceptor pairs that give different-colored CT bands in the visible spectrum are initially studied. The number of methylene units (m or n) will be adjusted to provide optimal intramolecular CT complexation. Inspection of the CPK models indicates that sufficient flexibility can be obtained with m or n<4. One potential concern is that most CT complexes including the ones illustrated herein are fairly weak with $K_a$<10 M$^{-1}$. This is not a problem for the present foldamers, because a donor-acceptor distance of 1 nm translates to an effective concentration of nearly 1M for the donor and the acceptor. At 1 M, the degree of complexation is calculated to be about 40% for $K_a$=1 M$^{-1}$ and about 80% for $K_a$=10 M$^{-1}$.

The assays potentially can, for example, be performed in two ways. First, a one-phase assay can be used where the foldamers will be dissolved in a miscible solvent mixture that favors folding—e.g. water/THF, methanol/EA or methanol/ (EA-hexane). As shown by the mercury sensor described above, mixed solvents may not be necessary if strong interactions exist between the foldamer and the substrate. Such strong interactions may occur here because of the strength of aminidnium-carboxylate salt bridge. Orner, B. P.; Hamilton, Andrew D. The Guanidinium Group in Molecular Recognition: Design and Synthetic Approaches. *J. Inclusion Phenom. Macrocyc. Chem.* 41, 141-147 (2001); Hannon, C. L.; Anslyn, E. V. The Guanidinium Group: Its Biological Role; Synthetic Analogs. In *Bioorganic Chemistry Frontiers*; Dugas, H., Schmidtchen, F. P., Eds.; Springer: Heidelberg, pp 193-255 (1993); Yamamoto, Y.; Kojima, S. In Synthesis and Chemistry of Guanidine Derivatives; Patai, S., Rappoport, Z. Eds. John Wiley & Sons: New York, Vol. 2, pp 485-526 (1991); Schmidtchen, F. P.; Berger, M. Artificial Organic Host Molecules for Anions. *Chem. Rev.* 97, 1609-1646 (1997); Schmidtchen, F. P. Artificial Anion Hosts. Concepts for Structure and Guest Binding. In *Supramolecular Chemistry of Anions*; Bianchi, A.; Bowman-James, K., Garcia-Espana, E. Eds. Wiley-VCH: New York, pp 79-146 (1997). Binding can be reported as an increase in the acceptor emission (in FRET) or appearance of the CT band.

Second, a two phase assay can be used where a known amount of the foldamer sensor will be added to an immiscible mixture such as water/CHCl$_3$, methanol/hexane, or DMSO/ hexane. Both the cationic foldamer and the anionic analyte will initially stay in the polar phase, but are expected to migrate to the nonpolar phase upon complexation and charge-neutralization. Binding is again detected by fluorescence or colorimetry in the nonpolar phase.

A large body of evidence indicates that guanidinium-rich oligomers, including those made from cholates (Janout et al. *J. Am. Chem. Soc.* 125, 4436-4437 (2003); Baragaña et al. *Chem.-Eur. J.* 8, 2931-2936 (2002)), can translocate polar molecules and particularly anionic ones across cell membranes. Polyarginine in fact has been shown to migrate from aqueous to organic phase upon anion-complexation. Sakai, N.; Matile, S. Anion-Mediated Transfer of Polyarginine Membranes. *J. Am. Chem. Soc.* 125, 14348-14356 (2003). Thus, the oligoguanidinium cholate foldamers, which have large hydrophobic surface areas, are expected to have no difficulty going into the nonpolar phase upon charge neutralization and folding.

REFERENCES

Koshland, D. E., Jr. *Proc. Natl. Acad. Sci. U.S.A.* 1958, 44, 98-104.
Koshland, D. E., Jr. Nature Med. 1998, 4, 1112-1114.
Hervé, G., Ed. *Allosteric Enzymes*; CRC Press: Boca Raton, Fla., 1989.
Perutz, M. F. *Mechanisms of CooperatiVity and Allosteric Regulation in Proteins*; Cambridge University Press: Cambridge, 1990.
Hervé, G., Ed. *Allosteric Enzymes*; CRC Press: Boca Raton, Fla., 1989.
Kvamme, E., Pihl, A., Eds. *Regulation of Enzyme ActiVity and Allosteric Interactions*; Academic Press: New York, 1968.
Gellman, S. H. *Acc. Chem. Res.* 1998, 31, 173-180.
Kirschenbaum, K.; Zuckerman, R. N.; Dill, D. A. *Curr. Opin. Struct. Biol.* 1999, 9, 530-535.
Hill, D. J.; Mio, M. J.; Prince, R. B.; Hughes, T. S.; Moore, J. S. *Chem. ReV.* 2001, 101, 3893-4011.
Cubberley, M. S.; Iverson, B. L. *Curr. Opin. Chem. Biol.* 2001, 5, 650-653.

Sanford, A. R.; Gong, B. Curr. Org. Chem. 2003, 7, 1649-1659.
Ryu, E.-H.; Zhao, Y. Org. Lett. 2004, 6, 3187-3189.
Zhong, Z.; Yan, J.; Zhao, Y. Langmuir 2005, 21, 6235-6239.
Zhao, Y.; Ryu, E.-H. J. Org. Chem. 2005, 70, 7585-7591.
Stein, T. M.; Gellman, S. H. J. Am. Chem. Soc. 1992, 114, 3943-3950.
Cheng, Y.; Ho, D. M.; Gottlieb, C. R.; Kahne, D.; Bruck M. A. J. Am. Chem. Soc. 1992, 114, 7319-7320.
Venkatesan, P.; Cheng, Y.; Kahne, D. J. Am. Chem. Soc. 1994, 116, 6955-6956.
McQuade, D. T.; Barrett, D. G.; Desper, J. M.; Hayashi, R. K.; Gellman, S. H. J. Am. Chem. Soc. 1995, 117, 4862-4869.
Broderick, S.; Davis, A. P.; Williams, R. P. Tetrahedron Lett. 1998, 39, 6083-6086.
Isaacs, L.; Witt, D.; Fettinger, J. C. Chem. Commun. 1999, 2549-2550.
Taotafa, U.; McMullin, D. B.; Lee, S. C.; Hansen, L. D.; Savage, P. B. Org. Lett. 2000, 2, 4117-4120.
Arnt, L.; Tew, G. N. J. Am. Chem. Soc. 2002, 124, 7664-7665.
Zhong, Z.; Yan, J.; Zhao, Y. Langmuir 2005, 21, 6235-6239.
Davis, A. P.; Bonar-Law, R. P.; Sanders, J. K. M. In Comprehensive Supramolecular Chemistry; Atwood, J. L., Davis, J. E. D., MacNicol, D. D., Vogtle, F., Eds.; Elsevier: Oxford, 1996; Vol. 4, Chapter 7.
Li, Y.; Dias, J. R. Chem. Rev. 1997, 97, 283-304.
Maitra, U. Curr. Sci. 1996, 71, 617-624.
Smith, B. D.; Lambert, T. N. Chem. Commun. 2003, 2261-2268.
Davis, A. P.; Joos, J.-B. Coord. Chem. Rev. 2003, 240, 143-156.
Burrows, C. J.; Sauter, R. A. J. Inclusion. Phenom. 1987, 5, 117-121.
Janout, V.; Lanier, M.; Regen, S. L. J. Am. Chem. Soc. 1996, 118, 1573-1574.
Ariga, K.; Terasaka, Y.; Sakai, D.; Tsuji, H.; Kikuchi, J.-I. J. Am. Chem. Soc. 2000, 122, 7835-7836.
Werner, F.; Schneider, H.-J. J. Inclusion Phenom. Macro. Chem. 2001, 41, 37-40.
Yoshino, N.; Satake, A.; Kobuke, Y. Angew. Chem., Int. Ed. 2001, 40, 457-459.
Tanford, C. The Hydrophobic Effect: Formation of Micelles and Biological Membranes, 2nd ed.; Wiley: New York, 1980.
Ben-Naim, A. Hydrophobic Interactions; Plenum Press: New York, 1980.
Blokzijl, W.; Engberts, J. B. F. N. Hydrophobic Effects: Opinions and Facts. Angew. Chem., Int. Ed. Engl. 1993, 32, 1545-1579.
Gong, B., et al. Proc. Natl. Acad. Sci. U.S.A. 2002, 99, 11583-11588.
Davis, A. P.; Dresen, S.; Lawless, L. J. Tetrahedron Lett. 1997, 38, 4305-4308.
Fery-Forgues, S.; Fayet, J.-P.; Lopez, A. J. Photochem. Photobiol. A 1993, 70, 229-2463.
Chan, H. S.; Bromberg, S.; Dill, K. A. Philos. Trans. R. Soc. London, Ser. B 1995, 348, 61-70.
Schellman, J. A. J. Phys. Chem. 1958, 62, 1485-1494.
Zimm, B. H.; Bragg, J. K. J. Chem. Phys. 1959, 31, 526-535.
Lifson, S.; Roig, A. J. Chem. Phys. 1961, 34, 1963-1974.
Poland, D. C.; Scheraga, H. A. Theory of the Helix-Coil Transition; Academic Press: New York, 1970.
Abraham, M. H. J. Am. Chem. Soc. 1982, 104, 2085-2094.
Abraham, M. H.; Grellier, P. L.; McGill, R. A. J. Chem. Soc., Perkin Trans. 2 1988, 339-345.
Schneider, H.-J.; Kramer, R.; Simova, S.; Schneider, U. J. Am. Chem. Soc. 1988, 110, 6442-6448.
Stryer, L. Annu. Rev. Biochem. 1978, 47, 819-846.
Selvin, P. R. Methods Enzymol. 1995, 246, 300-334.
Lakowicz, J. R. Principles of Fluorescence Spectroscopy, 2nd ed.; Kluwer: New York, 1999; Chapter 13.
Matsuda, K.; Stone, M. T.; Moore, J. S. J. Am. Chem. Soc. 2002, 124, 11836-11837.
Stryer, L.; Haugland, R. P. Proc. Natl. Acad. Sci. U.S.A. 1967, 58, 719-726.
Brady, P. A.; Bonar-Law, Ri. P.; Rowan, S. J.; Suckling, C. J.; Sanders, J. K. M. Chem. Commun. 1996, 319-320.
Pace, C. N. Methods in Enzymology; Hirs, C. H. W., Timasheff, S, N., Eds.; Academic Press: New York, 1986; Vol. 131, pp 266-280.
Pace, C. N.; Shirley, B. A.; Thomson, J. A. Protein Structure: A Practical Approach;
Creighton, T. E., Ed.; IRL Press: New York, 1989; pp 311-330.
Prince, R. B.; Saven, J. G.; Wolynes, P. G.; Moore, J. S. J. Am. Chem. Soc. 1999, 121, 3114-3121.
Gellman, S. H. Acc. Chem. Res. 1998, 31, 173-180.
Kirshenbaum, K.; Zuckermann, R. N.; Dill, K. A. Curr. Opin. Struct. Biol. 1999, 9, 530-535.
Stigers, K. D.; Soth, M. J.; Nowick, J. S. Curr. Opin. Chem. Biol. 1999, 3, 714-723.
Hill, D. J.; Mio, M. J.; Prince, R. B.; Hughes, T. S.; Moore, J. S. Chem. Rev. 2001, 101, 3893-4012.
Cubberley, M. S.; Iverson, B. L. Curr. Opin. Chem. Biol. 2001, 5, 650-653.
Sanford, A. R.; Gong, B. Curr. Org. Chem. 2003, 7, 1649-1659.
Martinek, T. A.; Fulop, F. Eur. J. Biochem. 2003, 270, 3657-3666.
Cheng, R. P. Curr. Opin. Struc. Biol. 2004, 14, 512-520.
Huc, I. Eur. J. Org. Chem. 2004, 17-29.
Licini, G.; Prins, L. J.; Scrimin, P. Eur. J. Org. Chem. 2005, 969-977.
Lokey, R. S.; Iverson, B. L. Nature 1995, 375, 303-305.
Stone, M. T.; Heemstra, J. M.; Moore, J. S. Acc. Chem. Res. 2006, 39, 11-20.
Ryu, E.-H.; Zhao, Y. Org. Lett. 2004, 6, 3187-3189.
Zhao, Y.; Ryu, E.-H. J. Org. Chem. 2005, 70, 7585-7591.
E.-H. Ryu, Y. Jie, Z. Zhong, Y. Zhao, J. Org. Chem. 2006, 71, 7205-7213.
Zhao, Y.; Zhong, Z. J. Am. Chem. Soc. 2005, 127, 17894-17901.
Zhao, Y.; Zhong, Z. J. Am. Chem. Soc. 2006, 128, 9988-9989.
Zhao, Y.; Zhong, Z. Org. Lett. 2006, 8, 4715-4717.
Fendler, J. H. Membrane Mimetic Chemistry; Wiley: New York, 1982; Chapter 3.
Marcus, Y. Solvent Mixtures: Properties and Selective Solvation; Marcel Dekker: New York, 2002.
Reichardt, C. Solvents and Solvent Effects in Organic Chemistry; Wiley: Weinheim, 2003; pp 38-42.
Chapman, K. T.; Still, W. C. J. Am. Chem. Soc. 1989, 111, 3075-3077.
Hof, F.; Craig, S. L.; Nuckolls, C.; Rebek, J.; Jr. Angew. Chem. Int. Ed. 2002, 41, 1488-1508.
Roncucci, P.; Pirondini, L.; Paderni, G.; Massera, C.; Dalcanale, E.; Azov, V. A.; Diederich, F. Chem.—Eur. J. 2006, 12, 4775-4784.
Sandström, M; Persson, I.; Persson, P. Acta Chem. Scand. 1990, 44, 653-675.
Chen, T.; Hefter, G.; Marcus, Y. J. Sol. Chem. 2000, 29, 201-216.
Marcus, Y. The Properties of Solvents; Wiley: New York, 1999; p 176.
Stryer, L. Annu. Rev. Biochem. 1978, 47, 819-846.

Selvin, P. R. Methods Enzymol. 1995, 246, 300-334.
Lakowicz, J. R. Principles of Fluorescence Spectroscopy, 2nd Ed.; Kluwer: New York, 1999; Chap. 13.
Prince R. B.; Saven, J. G.; Wolynes, P. G.; Moore, J. S. J. Am. Chem. Soc. 1999, 121, 3114-3121.
Pace, C. N. Methods in Enzymology; Hirs, C. H. W.; Timasheff, S, N. Eds.; Academic Press: New York, 1986; Vol. 131, pp 266-280.
Pace, C. N. Shirley, B. A.; Thomson, J. A. Protein Structure: A Practical Approach; Creighton, T. E. Ed.; IRL Press: New York, 1989; pp 311-330.
Marcus, Y. The Properties of Solvents; Wiley: New York, 1999; pp 142-154.
Beckstein, O.; Biggin, P. C.; Sansom, M. S. P. J. Phys. Chem. B 2001, 105, 12902-12905.
Beckstein, O.; Biggin, P. C.; Bond, P.; Bright, J. N.; Domene, C.; Grottesi, A.; Holyoake, J.; Sansom, M. S. P. FEBS Lett. 2003, 555, 85-90.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An oligomer comprising CHO subunits of the following formula:

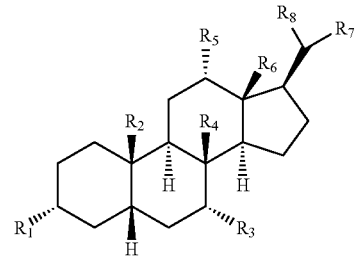

wherein:
$R_1$, $R_3$, and $R_5$ are independently hydrogen, hydroxy (OH), alkoxy, alkoxyalkyl, amine, azide, boronate, mercapto, sulfide, sulfone, sulfoxide, sulfoninium, phosphine, phosphate, phosphate, a heterocycle, a solid support, a linker or a label, wherein each alkoxy and/or alkoxyalkyl can independently be substituted with one or more hydroxy, alkyl, alkenyl, alkynyl, amine, ammonium, sulfate, phosphate, carboxy, mercapto, sulfide, sulfone, sulfoxide, sulfoninium, phosphine, heteroaromatic cycle, or epoxy groups;
$R_2$, $R_6$ and $R_8$ are independently lower alkyl;
$R_4$ is hydrogen or lower alkyl;
$R_7$ is carboxylate, alkylenecarboxylate, alkylenecarboxyl, lower alkyl alkylenecarboxylate ester, alkyleneamide, alkyleneamine, alkylenethiol, a solid support, a linker or a label;
wherein the CHO subunits are linked head-to-tail by covalent bonds formed between $R_1$ and $R_7$ groups, wherein at least a segment of the oligomer has a hydrophilic face and a hydrophobic face and wherein at least one segment of the oligomer can fold into a helix to enclose the hydrophilic face;
wherein the covalent bonds formed between $R_1$ and $R_7$ groups are amide, carbamate, urea, ether, sulfide, disulfide, amine, cyclic heteroaromatic ring, or combinations thereof, and wherein the oligomer has at least 4 subunits.

2. The oligomer of claim 1, wherein each $R_1$ is an amine, each $R_7$ is alkylenecarboxyl and the $R_1$ amine and $R_7$ alkylenecarboxyl groups each form an amide covalently linking each subunit in the oligomer.

3. The oligomer of claim 1, wherein the oligomer is attached to or inserted into a linear polymer, a branched polymer, a dendrimer, or combinations thereof.

4. The oligomer of claim 1, further comprising one or more amino acid subunits.

5. The oligomer of claim 1, selected from one of the following compounds:
Cho-Cho-Glu-Cho-Cho-Glu-Cho
Cho-Glu-Cho-Cho-Cho-Glu-Cho
Glu-Cho-Cho-Cho-Cho-Glu-Cho
Glu-Cho-Cho-Cho-Cho-Cho-Glu
Cho-Glu-Cho-Cho-Cho-Glu-Cho-Cho    Cho-Glu-Cho-Cho-Cho-Glu-Cho-Cho-Cho
Cho-Glu-Cho-Glu-Cho-Glu-Cho-Glu-Cho
Cho-Cho-Arg-Cho-Arg-Cho-Cho
Cho-Cho-Arg-Cho-Cho-Arg-Cho-Cho
Dansyl-Cho-Cho-Met-Cho-Cho-Met-Cho-Cho-CONHCH$_2$CH$_2$—(OCH$_2$CH$_2$)OH
2,4-Dimethoxystilbene-Cho-Arg-Cho-Cho-Arg-Cho-Cho-Cho-Trp
Anthracene-Cho-Arg-Cho-Cho-Cho-Cho-Arg-Cho-Trp
7-Dimethylaminocoumarine-Cho-Arg-Cho-Cho-Cho-Cho-Cho-Cho-Arg-Trp
Fluorescein-Cho-Cho-Arg-Cho-Cho-Arg-Cho-Cho-Arg-Trp
Dansyl-Cho-Arg-Cho-Arg-Cho-Arg-Cho-Cho-Cho-Trp
Eosin-Cho-Arg-Cho-Arg-Cho-Arg-Cho-Arg-Cho-Cho-Trp;
Dansyl-Cho-Cho-Met-Cho-Cho-Met-Cho-Cho-Methyl
2,4-Dimethoxystilbene-Cho-Arg-Cho-Cho-Arg-Cho-Cho-Cho-Tryp (51a)
Anthracene-Cho-Arg-Cho-Cho-Cho-Cho-Arg-Cho-Tryp (51b)
7-Dimethylaminocoumarine-Cho-Arg-Cho-Cho-Cho-Cho-Cho-Cho-Arg-Tryp (51c)
Fluorescein-Cho-Cho-Arg-Cho-Cho-Arg-Cho-Cho-Arg-Tryp (51d)
Dansyl-Cho-Arg-Cho-Arg-Cho-Arg-Cho-Cho-Cho-Tryp (51e)
Eosin-Cho-Arg-Cho-Arg-Cho-Arg-Cho-Arg-Cho-Cho-Tryp (51f)
wherein Cho is a subunit as defined in claim 1 and the Cho subunits are covalently linked to other Cho subunits or to amino acid subunits by an amide bond.

6. An oligomer selected from one of the following compounds:

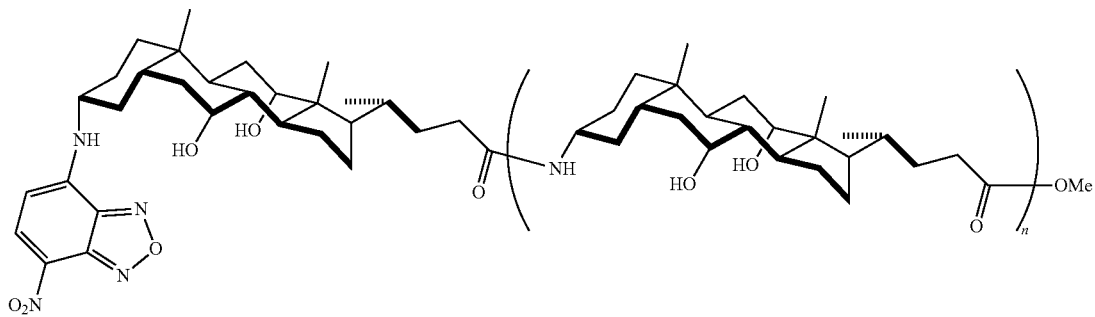

1, n = 0
2, n = 2
3, n = 4
4, n = 6

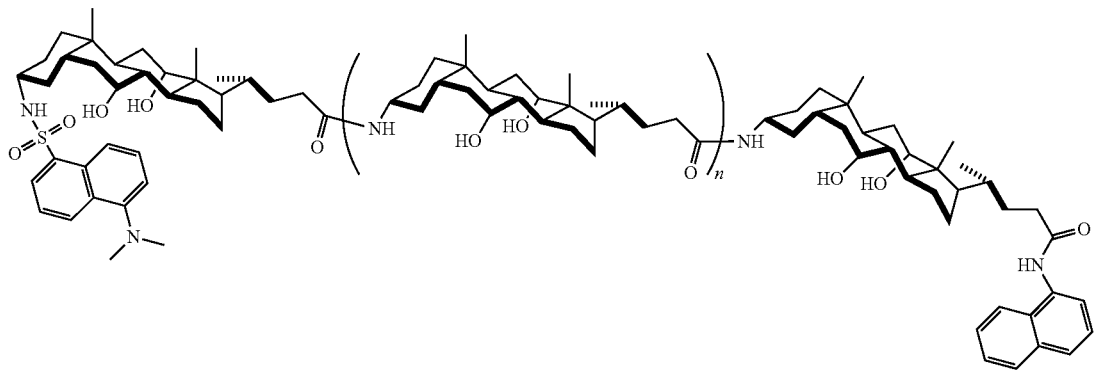

5, n = 3
6, n = 4
7, n = 5

-continued
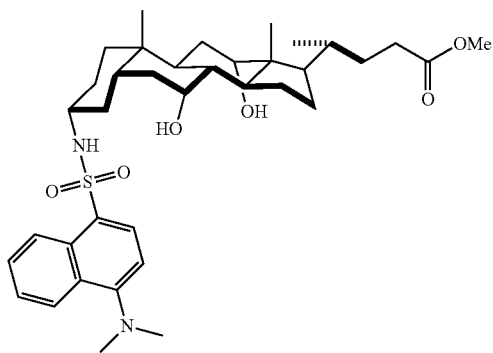
8
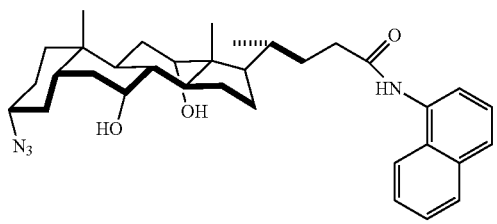
9
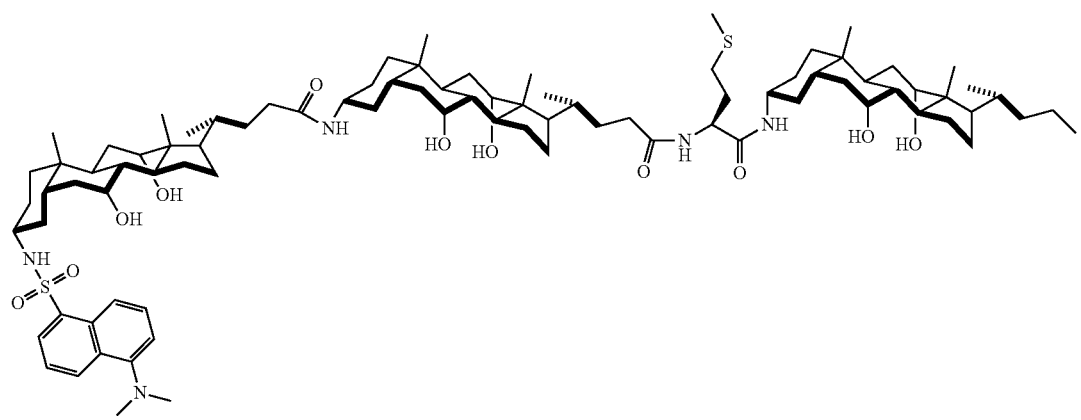
10
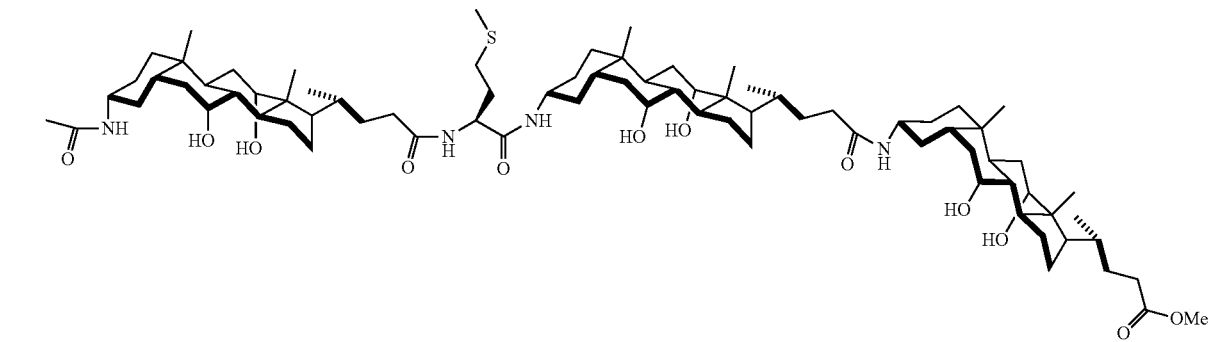
101
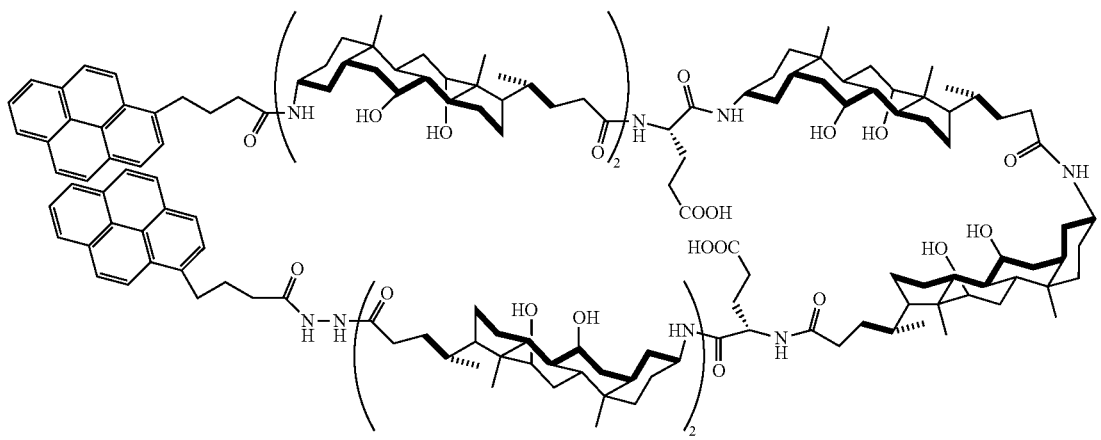

-continued

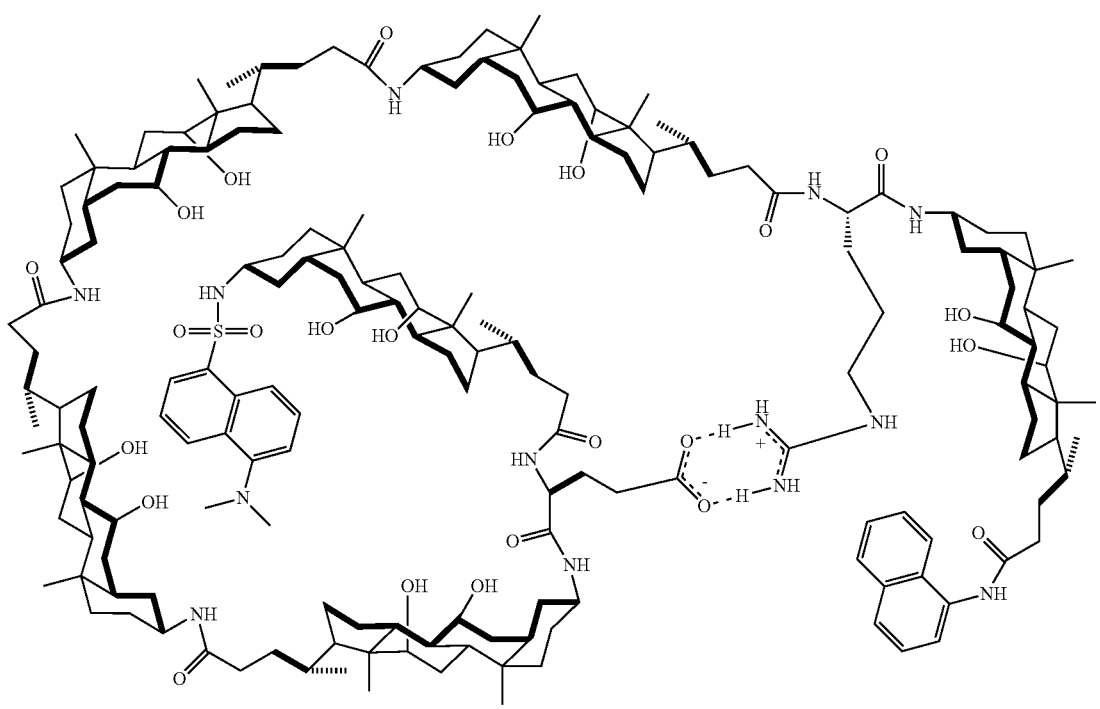

7. The oligomer of claim 1, wherein the oligomer is attached to a solid support.

8. The oligomer of claim 7, wherein the solid support comprises gold, titanium, palladium, chromium, quartz, aluminum, silicon or mixtures and/or layers thereof.

9. The oligomer of claim 7, wherein the solid support comprises a bead or a column matrix.

10. The oligomer of claim 1, further comprising a therapeutic agent.

11. The oligomer of claim 1, further comprising a liposome.

12. The oligomer of claim 4, wherein the oligomer is within the liposome's membrane.

13. The oligomer of claim 1, wherein the oligomer comprises the following formula:

Xaa-(Xaa)$_m$-Xaa wherein:
m is an integer of 2-1000; and
each Xaa is independently the CHO subunit as defined in claim 1 or an amino acid subunit.

14. The oligomer of claim 13, wherein each amino acid subunit is flanked by two CHO subunits unless the amino acid is at the terminus of the oligomer.

15. The oligomer of claim 13, wherein the oligomer comprises at least one Glu, Asp, Lys, Arg, Trp, Met, or Cys.

16. The oligomer of claim 13, wherein the oligomer comprises two amino acid subunits.

17. A pharmaceutical composition comprising a pharmaceutically acceptable carrier, a therapeutic agent and the oligomer of claim 1.

18. The composition of claim 17, wherein the oligomer binds the therapeutic agent.

19. The composition of claim 17, further comprising a liposome.

20. The composition of claim 17, wherein the oligomer iscan be within the liposome's membrane.

21. A method of detecting a change in a solution comprising contacting the solution with the oligomer of claim 1, observing whether the oligomer undergoes a conformational change to thereby detect the change in the solution; wherein the change in solution comprises a change in the solution's temperature or a change in metal ion or small molecule concentration.

22. The method of claim 21, wherein the conformational change comprises folding to expose or envelop charged moieties on or within the oligomer.

23. The method of claim 21, wherein the conformational change comprises the oligomer folding into a helix.

24. The method of claim 21, wherein the conformational change comprises unfolding of the oligomer.

25. The method of claim 21, wherein the solution comprises a patient's fluid sample, a soil sample, a water sample, a waste fluid sample, or a test sample.

26. The method of claim 21, wherein the metal ion is lead, cadmium, zinc, cobalt, nickel, silver or iron.

27. The method of claim 21, wherein the metal ion is mercury or zinc.

28. The method of claim 21, wherein the small molecule is a drug, a polyanion, a metabolite, a sugar, ATP, GTP, an acid, a base or a hydrocarbon.

29. A method of sustained delivery of a therapeutic agent to a patient, comprising administering the composition of claim 17 to the patient.

30. The method of claim 29, wherein the composition is locally administered to a selected site of the patient's body.

31. The method of claim 30, wherein the site is a tumor, heart, kidney, brain, or internal organ of the patient.

* * * * *

UNITED STATES PATENT AND TRADEMARK OFFICE
CERTIFICATE OF CORRECTION

| | | |
|---|---|---|
| PATENT NO. | : 7,960,439 B1 | Page 1 of 3 |
| APPLICATION NO. | : 11/811905 | |
| DATED | : June 14, 2011 | |
| INVENTOR(S) | : Yan Zhao | |

It is certified that error appears in the above-identified patent and that said Letters Patent is hereby corrected as shown below:

In column 2, line 16, delete "sulfoninium," and insert -- sulfonium, --, therefor.

In column 2, line 21, delete "caroboxy," and insert -- carboxy, --, therefor.

In column 2, line 22, delete "sulfoninium," and insert -- sulfonium, --, therefor.

In column 3, line 3, delete "sulfoninium," and insert -- sulfonium, --, therefor.

In column 3, line 8, delete "caroboxy," and insert -- carboxy, --, therefor.

In column 3, line 9, delete "sulfoninium," and insert -- sulfonium, --, therefor.

In column 3, line 12, delete "$R_1$," and insert -- $R_{11}$ --, therefor.

In column 4, line 63, delete "tryptoamide" and insert -- tryptamide --, therefor.

In column 10, line 40, after "2.0" insert -- μM. --.

In column 10, line 41, delete "151" and insert -- -15I --, therefor.

In column 14, line 17, delete "sulfoninium," and insert -- sulfonium, --, therefor.

In column 14, line 22, delete "caroboxy," and insert -- carboxy, --, therefor.

In column 14, line 23, delete "sulfoninium," and insert -- sulfonium, --, therefor.

In column 14, line 35, delete "$R_1$," and insert -- $R_1$ --, therefor.

Signed and Sealed this
Sixth Day of September, 2011

David J. Kappos
*Director of the United States Patent and Trademark Office*

CERTIFICATE OF CORRECTION (continued)
U.S. Pat. No. 7,960,439 B1

In column 29, line 29, delete "$\Delta G = RT \ln K_{eq} = -RT \ln(f_U / f_F) = -RT \ln[f_U / (1 - f_U)]$ (3)" and insert -- $\Delta G = -RT \ln K_{eq} = -RT \ln(f_U/f_F) = -RT \ln[f_U/(1 - f_U)]$ (3) --, therefor.

In column 37, line 64, delete "8):" and insert -- $\delta$): --, therefor.

In column 37, line 67, delete "8):" and insert -- $\delta$): --, therefor.

In column 40, line 38, delete "[M+K]," and insert -- $[M+K]^+$, --, therefor.

In column 42, line 41, delete "$C_{130}H_2O_2N_8NaO_{15}$" and insert -- $C_{130}H_{202}N_8NaO_{15}$ --, therefor.

In column 42, line 65, delete "8):" and insert -- $\delta$): --, therefor.

In column 43, line 3, delete "8):" and insert -- $\delta$): --, therefor.

In column 52, line 48, delete "(+)" and insert -- (♦) --, therefor.

In column 68, line 33, delete "$K_a(M^{-1})^b$" and insert -- $K_a(M^{-1})^a$ --, therefor.

In column 73, line 56, delete "– $\Delta G_{folding}$ = 1.7 kcal/mol)." and insert -- – $\Delta G_{folding}$ = –1.7 kcal/mol). --, therefor.

In column 77, line 63, delete "(FIG. 151, A)." and insert -- (FIG. 15I, ▲). --, therefor.

In column 84, line 15, delete "Example 5" and insert -- Example 6 --, therefor.

In column 86, line 36, delete "(52t)" and insert -- (52f) --, therefor.

In column 88, line 6, delete "aminidnium" and insert -- amidinium --, therefor.

In column 92, line 37, in Claim 1, delete "sulfoninium," and insert -- sulfonium, --, therefor.

In column 92, line 38, in Claim 1, after "phosphine," delete "phosphate,".

In column 92, line 43, in Claim 1, delete "sulfoninium," and insert -- sulfonium, --, therefor.

CERTIFICATE OF CORRECTION (continued)
U.S. Pat. No. 7,960,439 B1

In column 97-98, line 1, in Claim 6, after

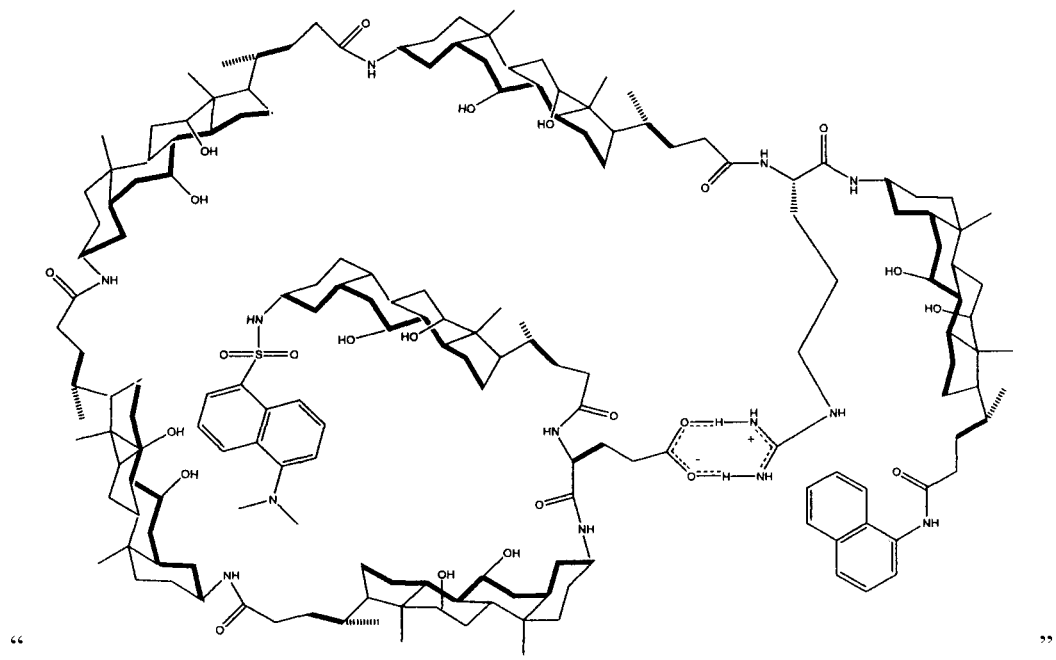

" "

insert -- . --.

In column 98, line 32, in Claim 20, delete "iscan be" and insert -- is --, therefor.